US010500176B2

(12) United States Patent
Hirvonen et al.

(10) Patent No.: US 10,500,176 B2
(45) Date of Patent: Dec. 10, 2019

(54) METHOD FOR ENHANCING ENERGY PRODUCTION AND METABOLISM IN CELLS

(71) Applicant: REPLICON HEALTH OY, Espoo (FI)

(72) Inventors: Petteri Hirvonen, Helsinki (FI); Peter Eriksson, Helsinki (FI); Risto Kaksonen, Espoo (FI)

(73) Assignee: REPLICON HEALTH OY, Espoo (FI)

( * ) Notice: Subject to any disclaimer, the term of this patent is extended or adjusted under 35 U.S.C. 154(b) by 0 days.

(21) Appl. No.: 14/917,764

(22) PCT Filed: Sep. 12, 2014

(86) PCT No.: PCT/FI2014/050698
§ 371 (c)(1),
(2) Date: Mar. 9, 2016

(87) PCT Pub. No.: WO2015/036656
PCT Pub. Date: Mar. 19, 2015

(65) Prior Publication Data
US 2016/0213629 A1 Jul. 28, 2016

(30) Foreign Application Priority Data
Sep. 13, 2013 (FI) .................................. 20135927

(51) Int. Cl.
*A61K 31/191* (2006.01)
*A61K 31/19* (2006.01)
*A23L 2/52* (2006.01)
*A23L 33/10* (2016.01)

(52) U.S. Cl.
CPC ............. *A61K 31/191* (2013.01); *A23L 2/52* (2013.01); *A23L 33/10* (2016.08); *A61K 31/19* (2013.01); *A23V 2002/00* (2013.01)

(58) Field of Classification Search
CPC ............................... A61K 31/191; A61K 31/22
See application file for complete search history.

(56) References Cited

U.S. PATENT DOCUMENTS

| 4,246,261 | A | * | 1/1981 | Van Scott | ............ | A61K 9/0014 514/171 |
| 7,666,909 | B2 | | 2/2010 | Heino | | |
| 2002/0019563 | A1 | * | 2/2002 | Webber | .................. | C07C 317/48 562/477 |
| 2003/0069232 | A1 | * | 4/2003 | Chiou | ................... | A61K 9/0048 514/224.8 |
| 2004/0220259 | A1 | * | 11/2004 | Yu | ......................... | A61K 8/365 514/460 |
| 2006/0024284 | A1 | | 2/2006 | Teichberg | | |
| 2006/0025476 | A1 | * | 2/2006 | Antosh | .................. | A61K 31/22 514/546 |
| 2006/0204551 | A1 | * | 9/2006 | Manley | .................... | A23G 3/34 424/439 |
| 2006/0217303 | A1 | * | 9/2006 | Kriegler | .................. | A61K 31/19 514/100 |
| 2007/0276037 | A1 | * | 11/2007 | Woo | ........................ | A61K 31/21 514/546 |
| 2011/0117210 | A1 | * | 5/2011 | Ugolkov | ............... | A61K 31/315 424/643 |

FOREIGN PATENT DOCUMENTS

| CN | 101991159 | A | * | 3/2011 |
| CN | 102038867 | A | | 5/2011 |
| JP | 61171418 | A | * | 8/1986 |
| JP | 2012/232902 | A | | 11/2012 |
| WO | 2004/093722 | A2 | | 11/2004 |
| WO | 2006/112961 | A2 | | 10/2006 |
| WO | 2012/019295 | A1 | | 2/2012 |

OTHER PUBLICATIONS

Definition of "parenteral," from the Oxford English Dictionary (retrieved from oed.com on Aug. 2, 2018). (Year: 2018).*
Hiroshi Habe et al., "Biotechnological production of d-glyceric acid and its application", Applied Microbiology and Biotechnology, Jul. 21, 2009, vol. 84, No. 3, pp. 445-452.
Hernandez-Aguilera et al., "Mitochondrial Dysfunction: A Basic Mechanism in Inflammation-Related Non-Communicable Diseases and Therapeutic Opportunities", Mediators of Inflammation, 2013, vol. 2013, pp. 1-13.
Anonymous, "Non-Communicable disease", Wikipedia, Jul. 15, 2013, http://en.wikipedia.org/w/index.php?title-Non-communicable_disease&oldid=564366376, 8 pages.
International Search Report dated Apr. 2, 2015 for International Application No. PCT/FI2014/050698, pp. 1-7.
International Preliminary Report on Patentablity dated Feb. 1, 2016 for International Application No. PCT/FI2014/050698, pp. 1-19.
Hiroshi Habe et al., "Use of a Gluconobacter frateurii Mutant to Prevent Dihydroxyacetone Accumulation during Glyceric Acid Production from Glycerol", Bioscience, Biotechnology and Biochemistry, Nov. 7, 2010, pp. 2330-2332.

(Continued)

*Primary Examiner* — Theodore R. West
(74) *Attorney, Agent, or Firm* — MH2 Technology Law Group, LLP

(57) ABSTRACT

The present invention relates to use of a composition comprising D-glyceric acid (DGA), DL-glyceric acid, L-glyceric acid, or hydroxypyruvatic acid and/or their salts or esters. Further, the invention relates to the use of said composition for enhancing direct and indirect mitochondrial metabolism, e.g. the ATP producing electron transport system (ETS), citric acid cycle or tricarboxylic acid cycle, (TCA), and beta oxidation, and also enhancing the shuttling of reducing equivalents from mitochondrial matrix into the cytosol and protein synthesis in the endoplasmic reticulum. Directly related to the above the use of DGA relates also to reducing the formation of reactive oxygen species (ROS). Alleviating, preventing and even healing effects towards extremely wide range of non-communicable diseases materializes.

13 Claims, 18 Drawing Sheets

(56) References Cited

OTHER PUBLICATIONS

Finnish Patent and Registration Office Search Report dated Jun. 23, 2014 from Finnish Application No. 20135927, 2 pages.

* cited by examiner

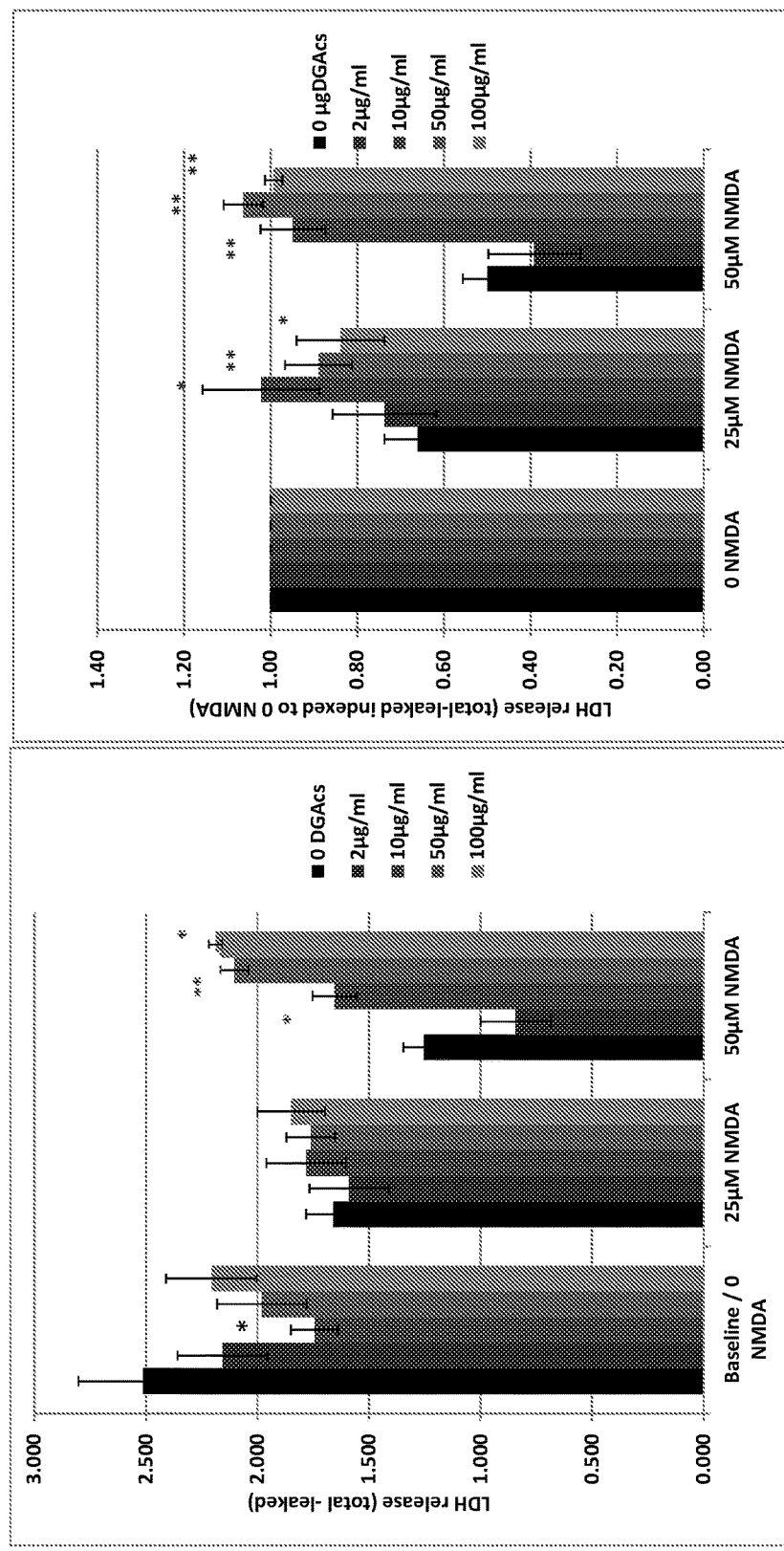
Fig. 14 a and 14 b

METHOD FOR ENHANCING ENERGY PRODUCTION AND METABOLISM IN CELLS

CROSS-REFERENCE TO RELATED APPLICATIONS

This application is a U.S. National Stage application of PCT/FI2014/050698 filed 12 Sep. 2014, which claims priority to Finland patent application 20135927 filed 13 Sep. 2013, the entire disclosures of which are hereby incorporated herein by reference in their entireties.

FIELD OF THE INVENTION

The present invention relates to use of a composition comprising D-glyceric acid (DGA), DL-glyceric acid, L-glyceric acid, or hydroxypyruvatic acid and/or their salts or esters. Further, the invention relates to the use of said composition for enhancing direct and indirect mitochondrial metabolism, e.g. the ATP producing electron transport system (ETS), citric acid cycle or tricarboxylic acid cycle, (TCA), and beta oxidation, and also enhancing the shuttling of reducing equivalents from mitochondrial matrix into the cytosol and protein synthesis in the endoplasmic reticulum. Directly related to the above the use of DGA relates also to reducing the formation of reactive oxygen species (ROS). Alleviating, preventing and even healing effects towards extremely wide range of non-communicable diseases materializes. Furthermore, the invention relates to a pharmaceutical substance, dietary supplement or nutritive substance comprising said compositions.

BACKGROUND OF THE INVENTION

Non-communicable mitochondrial diseases are becoming an increasing problem as population gets older and general life expectancy increases. Most often non-communicable mitochondrial diseases arise from some dysfunction of mitochondria itself or dysfunction in communication and cooperation of mitochondria and other cell organelles. These dysfunctions can lead to serious pathological conditions such as Alzheimer's disease, Parkinson's disease, cancer, cardiac disease, diabetes, epilepsy, Huntington's disease, and obesity. Mitochondrial matrix regulates through shuttle mechanisms cytosolic NAD+/NADH-ratio. Additionally in some physiological conditions it can also affect cytosolic NADPH/NADP$^+$ ratio. Increased mitochondrial biogenesis has been proposed as one solution in replacing dysfunctional (damaged) old mitochondria with new properly functioning mitochondria.

Reactive oxygen species (ROS) or free radicals are produced intracellularly through multiple mechanisms and depending on the cell and tissue types, the major sources being NAD(P)H oxidase complexes in cell membranes, mitochondria, peroxisomes and endoplasmic reticulum. (NADPH is nicotinamide adenine dinucleotide phosphate in reduced form.) Mitochondria convert energy for the cell into a usable ATP form. The process in which ATP is produced, called oxidative phosphorylation, involves the transport of protons (hydrogen ions) across the inner mitochondrial membrane by means of the electron transport chain or better described as electron transport system. Various complexes related to the ETS are scattered on the inner membrane relatively randomly not as a "chain". Complexes form a random system guided by greater reduction potential of next protein complex in the system, i.e. in the ETS electrons are passed through a series of proteins via oxidation-reduction reactions with each acceptor protein in the system having greater reduction potential than the previous. The last destination for an electron in this system is an oxygen molecule. Small part of electrons passing through the ETS escape, and oxygen is prematurely and incompletely reduced to give the superoxide radical. Superoxide is further converted e.g. to $H_2O_2$. ROS generation is most well documented for complex I and complex III.

ROSs are chemically reactive molecules containing oxygen. Examples include oxygen ions, peroxides and nitric oxide (NO). ROS form as a natural byproduct of the normal metabolism of oxygen and have important roles in cell signaling and homeostasis. However, during times of environmental stress (e.g., UV or heat exposure) or excessive metabolic stress, ROS levels can increase dramatically. This may result in significant damage to cell structures. Cumulatively, this is known as oxidative stress. ROS are also generated by exogenous sources such as ionizing radiation.

Normally, cells defend themselves against ROS damage with enzymes such as alpha-1-microglobulin, superoxide dismutases, catalases, lactoperoxidases, glutathione peroxidases and peroxiredoxins. Small molecule antioxidants such as ascorbic acid (vitamin C), tocopherol (vitamin E), uric acid, and glutathione also play important roles as cellular antioxidants. In a similar manner, polyphenol antioxidants assist in preventing ROS damage by scavenging free radicals. Antioxidant ability of the extracellular spaces, e.g. in plasma, is less efficient than intracellular ability. According to current knowledge the most important plasma antioxidant in humans is uric acid.

If too much damage is present in mitochondria, a cell undergoes apoptosis or programmed cell death. Bcl-2 proteins are layered on the surface of the mitochondria, detect damage, and activate a class of proteins called Bax, which punch holes in the mitochondrial outer membrane, causing cytochrome c to leak out. This cytochrome c binds to Apaf-1, or apoptotic protease activating factor-1, which is free-floating in the cell's cytoplasm. Using ATP as source of energy the Apaf-1 and cytochrome c bind together and form apoptosomes. The apoptosomes bind to and activate caspase-9, another free-floating protein. The caspase-9 then cleaves the proteins of the mitochondrial membrane, causing it to break down and start a chain reaction of protein denaturation and eventually phagocytosis of the cell.

Metabolic disorders are medical conditions characterized by problems with an organism's energy metabolism. Excessive nutrition and overweight are frequently related to a metabolic syndrome which has become a major health problem among humans. Metabolic syndrome is a combination of the medical disorders that, when occur together, increase the risk of developing cardiovascular disease and diabetes. Anabolic and catabolic reactions, regulatory hormones and proteins thereof are in a central position in the homeostasis of a human's metabolism. Fat and protein biosynthesis are examples of anabolic reactions. Aerobic degradation of carbohydrates, fats and carbon skeletons of amino acids represent a pathway, wherein oxygen is required in the last resort and which produces energy via the respiratory chain of the mitochondria. Coenzymes NAD$^+$ (nicotinamide adenine dinucleotide, oxidized) and NADH (nicotinamide adenine dinucleotide, reduced), which regulate the redox state of a cell are in a central role in these processes. An excessive reduction of NAD$^+$/NADH results in slow down of TCA, beta oxidation and glycolysis, and it can lead to cellular accumulation of AGEs (advanced glycation end-products). AGEs are proteins or lipids that become glycated after exposure to sugars and that cannot be used by normal metabolic pathways. AGEs are prevalent in the diabetic vasculature and contribute to the development of atherosclerosis.

In the transition to higher exercise intensity, the rate of adenosine triphosphate (ATP) hydrolysis is not matched by the transport of protons, inorganic phosphate and ADP into the mitochondria. Consequently, there is an increasing dependence on ATP supplied by glycolysis. Under these conditions, there is a greater rate of cytosolic proton release from glycolysis and ATP hydrolysis, the cell buffering capacity is eventually exceeded, and acidosis develops (Robergs, 2001). Increased capacity of cytosolic $NAD^+$ providing mitochondrial shuttles can alleviate, postpone, and/or in some cases prevent acidosis.

U.S. Pat. No. 7,666,909 relates to enhancement of alcohol metabolism using D-glyceric acid. Eriksson et al., 2007 reported that administration of ethanol and D-glyceric acid calcium salt to rats expedited the metabolism of alcohol. In that scientific paper it was hypothesized that the activation of enzymes related to the metabolism of alcohol and acetaldehyde, i.e. alcohol dehydrogenase and acetaldehyde dehydrogenase, and reaction from D-glyceric acid to glycerol and simultaneous oxidation of 2 $NAD^+$ molecules could possibly explain part of the acceleration in ethanol metabolism. Habe et al., 2011 showed in an in vitro study that D-glyceric acid can increase viability of ethanol-dosed gastric cells. Related to that article there seems to be also a patent that relates to alcohol induced gastrointestinal track mucous membrane damage and protection against it.

The existing solutions have been found to be ineffective in enhancing aerobic mitochondrial metabolism of carbohydrates, fats and amino acids as well as treating disorders related to metabolic disorders, especially outside of the gastrointestinal tract. Thus, there still exists a need to provide improved means and methods that are effective in the treatment and alleviation of metabolic.

SUMMARY OF THE INVENTION

The present invention relates to improved means and methods that are effective in the treatment and alleviation of metabolic disorders by enhancing mitochondrial aerobic metabolism.

The administration of calcium salt of D-glyceric acid generates an internal signaling process in cells, organs, and physiological systems, which increases mitochondrial aerobic metabolism and increases the energy production of cells. In consequence, for example the ability of mitochondrial shuttle mechanisms (e.g. MA and GP shuttles) to shuttle $NAD^+$ from the ETS to cytosol increases. Also beta oxidation of fats stored as triglycerides increases.

In the present invention the most probable candidate for the location dependent signaling that increases aerobic energy metabolism is the activation of GLYCTK1 and/or GLYCTK2 enzymes in the main direction of DGA and HPA metabolism (see FIG. 1b). High and prolonged ATP demand, like seen in e.g. endurance exercise, likely eventually also activates GLYCTK1 and/or GLYCTK2 genes (that can yield ATP). That is likely why also DGA and/or HPA administration is able to activate cellular mitochondrial aerobic energy metabolism, including beta oxidation. All processes presented in FIG. 2 are activated as a follow up.

The present inventors have directly by gene expression and mitochondrial biogenesis analyses shown that said signaling functions in hepatocytes, neurons and peripheral leukocytes. In addition, it has been shown by using blood tests that e.g. plasma lactate decreases more than 30%, which is a clear and strong indication that the activation of aerobic energy metabolism occurs also in skeletal muscles, heart and other vital inner organs. Mitochondrial structures of different cell types differ slightly from each other and therefore it is essential to prove directly that the activation of mitochondria occurs in all cell types. By activating Nrf2 pathway, the invention possesses beneficial effects even in matured red blood cells (RBC) that do not have mitochondria but possess active Nrf2 pathway.

The gist of the present invention is that mitochondria and mitochondrial energy metabolism is activated by administrating a composition comprising D-glyceric acid, DL-glyceric acid L-glyceric acid or hydroxypyruvatic acid or salt or ester thereof. This leads to activation of PGC-1a/NRF1 and Nrf2/ARE pathways and thus positive effects in the prevention of practically all non-communicative diseases, such as cardiovascular and neurodegenerative diseases, cancer, diabetes, hypertension, auto inflammatory and autoimmune diseases.

The indirect conversion of fats (energy from beta oxidation) to proteins of muscles tissues (from pyruvate and ammonia from decrease in urea cycle) is a central part of the present invention and this has been proved in Examples 2.1-2.3, 4 and 5.

An object of the present invention is to provide new means to alleviate the above mentioned problems.

An object of the invention is to provide a composition comprising one or more compounds selected from the group consisting of D-glyceric acid, DL-glyceric acid, L-glyceric acid, and hydroxypyruvatic acid and salts and esters thereof (later referred also as D-glycerate group) for use in a method of enhancing the direct and indirect mitochondrial metabolism and/or excretion of sugars (carbohydrates), fats (lipids) and/or amino acids. The enhancement is achieved by activating aerobic energy metabolism (the ETS), mitochondrial MA- and GP-shuttles, and by activating endogenous antioxidant defense mechanism and anti-inflammatory control of the cells (the Nrf2/ARE pathway). Biogenesis of new mitochondria is increased. By enhancing mitochondrial aerobic metabolism in cells and biogenesis of new mitochondria the use of DGA promotes alleviating effect towards non-communicable mitochondrial diseases in cells, tissues/organs and whole physiological systems, e.g. cardiovascular and/or central nervous systems.

An additional object of the use of DGA is to provide substrates for enhancing anaplerotic and anabolic processes like glyceroneogenesis, protein synthesis, and pentose phosphate pathway producing ribose-5-phosphate, the precursor of nucleobases adenine and guanine.

An advantage of the innovation is observed in fed and fasting state. Antioxidative state of the cells can be improved directly by: increasing the amount of reduced ubiquinol (from ubiquinone), and indirectly by increasing cytosolic NADPH generating capacity internally (PPP) and from the mitochondrial matrix. Enhanced energy metabolism and reduced oxidative stress of all cell types can improve whole physiological systems in all organisms. In prior art solutions there is no teaching that D-glyceric, DL-glyceric acid, L-glyceric acid, and hydroxypyruvatic acid and salts and esters thereof acid can improve antioxidant status of the cells.

Another object of the invention is to provide a composition comprising one or more compounds selected from the group consisting of D-glyceric acid, DL-glyceric acid, L-glyceric acid, and hydroxypyruvatic acid and salts and esters thereof for use in a method of treating or preventing a non-communicable disease or disorder. An object of the invention is also the use of said composition for improving general health of subjects in need.

Another object of the invention is the said composition for use in a method of reducing weight, in a method of treating or preventing a cardiovascular disease, in a method of treating or preventing a metabolic syndrome or a disorder associated with metabolism, in a method of treating or preventing the aging process of an organism, or in a method of treating or preventing cancer.

Another object of the present invention is to provide a composition for use in a method of influencing sugar, fat and/or amino acid metabolism and treating metabolic disorders which comprises a unit dosage form comprising a therapeutically effective unit dosage of D-glyceric acid, DL-glyceric acid, L-glyceric acid, hydroxypyruvatic acid and salts or esters thereof.

Another object of the invention is to provide a composition comprising one or more compounds selected from the group consisting of D-glyceric acid, DL-glyceric acid, L-glyceric acid, and hydroxypyruvatic acid and salts and esters thereof for use in a method of enhancing physical training, performance and recovery from exercise.

Another object of the invention is to provide a composition comprising one or more compounds selected from the group consisting of D-glyceric acid, DL-glyceric acid, L-glyceric acid, and hydroxypyruvatic acid and salts and esters thereof for use as an antioxidant.

Yet another object of the invention is a method of enhancing the metabolism of carbohydrates, and/or fats in a subject comprising administering a composition comprising an effective amount of one or more compounds selected from the group consisting of D-glyceric acid, DL-glyceric acid, L-glyceric acid, and hydroxypyruvatic acid and salts and esters thereof to a subject in need of preventing dysfunction in the catabolism of carbohydrates.

An additional object of the invention is an oral, topical, parenteral or inhalable composition for use in a method of prevention of dysfunction in catabolism of sugars, and enhancing the metabolism fat and/or amino acid comprising one or more compounds selected from the group consisting of D-glyceric acid, DL-glyceric acid, L-glyceric acid, and hydroxypyruvatic acid and salts and esters thereof. Said composition is e.g. a pharmaceutical preparation.

An additional object of the invention is a method of enhancing the biosynthesis of phospholipids and medium chain triglycerides enhanced by increased glyceroneogenesis. Furthermore an additional object of the innovation is to improve oxygen binding capacity of erythrocytes by improving their redox-state and enhancing glycolysis. Energy production and metabolism of erythrocytes increases overall viability and wellbeing of erythrocytes. Antioxidants help also by protecting their membrane integrity from radical species thus helping to keep their discoidal shape, and to increase oxygen releasing capacity of hemoglobin molecules by increasing 2,3-bisphosphoglycerate formation by increasing intracellular pH (=a follow up of enhanced conversion of $NAHD+H^+$ into $NAD^{30}$ and possibly of proton exporting capacity).

Innovation enhances wellbeing and viability of all cell types that use glycolysis and/or beta oxidation and citric acid cycle and the ETS in their metabolism and energy production, e.g. hepatocytes, myocytes, skeletal myotubes, erythrocytes, adipocytes, neurons and glial cells.

Organs and tissue types that benefit from the administration of the compounds of D-glycerate group are: liver, kidneys, pancreas, spleen, heart and skeletal muscles, cardiovascular system, brains and nervous system. An advantage of using the compounds of D-glycerate group comes from four main sources: 1) from improving the redox state of all cells, 2) increase in metabolic flux/diuretic effects (lower blood sugar, fats and sodium levels), 3) positive antioxidant effects, and 4) increase in mitochondrial biogenesis and energy metabolism.

An advantage of the present invention is the use of a composition comprising D-glyceric acid, DL-glyceric acid, L-glyceric acid, or hydroxypyruvatic acid and/or their salts or esters to enhance communication and cooperation of mitochondria and other cell organelles and the use of said composition to increase the biogenesis of new mitochondria. Such use has not been disclosed previously.

Another advantage of the invention is the use of a composition comprising D-glyceric acid, DL-glyceric acid, L-glyceric acid, or hydroxypyruvatic acid and/or their salts or esters to enhance endogenous cellular antioxidant defense.

Still another advantage of the invention is the incorporation of also hydroxypyruvatic acid. Reversible reduction and oxidation reactions between D-glyceric and hydroxypyruvatic are an important part in the long term efficacy of their use.

The present innovation does not relate to alcohol metabolism and/or gastrointestinal track.

BRIEF DESCRIPTION OF THE DRAWINGS

FIG. 1 furthermore depicts malate-aspartate (MA)-shuttle and glycerol phosphate-shuttle (GP-shuttle). These shuttle mechanisms are needed because IMM is impermeable for NADH and $NAD^+$. MA-shuttles transport $NAD^+$ from the matrix to the inter membrane space (IMS)/cytosol. Used graph is modified from a publicly available graph http://www.studyblue.com/notes/note/n/biologymetabolism/deck/801583. Abbreviations: MA-shuttle, malate-aspartate shuttle (MAL-ASP-shuttle); GP-shuttle, glycerol-phosphate shuttle; G-3-, glycerol phosphate; DHAP, dihydroxyacetone phosphate; TCA, tricarboxylic acid cycle; ETS, electron transport system; CI (or I), Complex I of the ETS; CII (or II), Complex II of the ETS, CIII (or III), Complex III of the ETS; CIV (or IV), Complex IV of the ETS; $NAD^+$, nicotinamide adenine dinucleotide, oxidized; NADH, nicotinamide adenine dinucleotide, reduced; FAD, flavin dinucleotide, oxidized; FADH2, flavin dinucleotide, reduced; Q, ubiquinone, oxidized; QH2, ubiquinol (fully) reduced.

FIG. 6a shows ROS in JGM (female donor), 20+20+1.5 h, equimolar comparisons to other best antioxidants in High Medium only. DGA 14 µM=2 µg/ml of DGA.

FIG. 6b shows ROS in JGM, 20+20+1.5 h, equimolar comparisons to best other antioxidants, High Medium and 0.75 mM of Palmitic acid. DGA 14 µM=2 µg/ml of DGA.

FIG. 9a: VIABILITY DOD, 24+24+1.5 h, High Medium only

FIG. 9b: VIABILITY YJM, 24+24+2 h, High Medium only

FIG. 9c: VIABILITY DOD, 24+24+1.5 h, High Medium+ sucrose

FIG. 9d: VIABILITY YJM, 24+24+2 h, High Medium+ sucrose

FIG. 10a: VIABILITY DOD, 48+1.5 h, Starving Diet

FIG. 10b: VIABILITY, YJM, 48 2 h, Starving Diet

FIG. 10c: Viability, CDP (male donor), 20+20+1.5 h, various diets with High Medium.

FIG. 11a: ROS, JGM, 20+20+1.5 h, High Medium+0.75 mM Palmitic Acid

FIG. 11b: ROS, CDP (male), 20+20+1.5 h, High Medium only

FIG. 11c: ROS, YJM, 20+20+1.5 h, High Medium+0.75 mM Palmitic acid. (LGA 14=2 µg/ml of LGA)

FIG. 11d: Viability, YJM, 20+20+1.5 h, High Medium+ 0.75 mM Palmitic acid. (LGA 14=2 µg/ml of LGA)

FIG. 12a: Hypertension, subject 5 (averages of three measurements. DGA dosing started on 26th of January and ended on 3rd of February. Dose 2×4 mg/kg/day).

FIG. 12b: Hypertension, subject 4 (averages of three measurements. Subject 4 received 1×4 mg/kg/day of DGA for 3 weeks).

In FIGS. 13 and 14a and 14b error bars are +/−SEM like in FIG. 5, i.e. not stds like in other graphs.

FIGS. 14a and 14b depict the protection by the use of DGA against NMDA stimulated excitotoxic injury in rat cortical neurons. FIG. 14a shows Viability at 7 DIV+24 h after 1 h NMDA stimulation at 7 DIV. FIG. 14b shows Viability after 24 hours with 1 h NMDA stimulation, indexed to 0 NMDA.

DGAcs treatment induces very clear and significant protection against NMDA-induced excitotoxity in both 25 µM NMDA and 50 µM NMDA group when cell death before and at the start of the test is taken into account (FIG. 14b). Even without correction for CR induced viability loss before the NMDA treatment, DGAcs administration induces very clear protection against NMDA-induced excitotoxity in 50 µM NMDA group (FIG. 14. a). In FIG. 14a "Baseline/NMDA 0" group is the same as in FIG. 13 Sign "*" indicates statistically significant difference compared to the control (p-value is clearly less than 5%), and "**" statistically very significant difference compared to the control (p-value clearly less than 1%).

DETAILED DESCRIPTION OF THE INVENTION

Figure 1A:
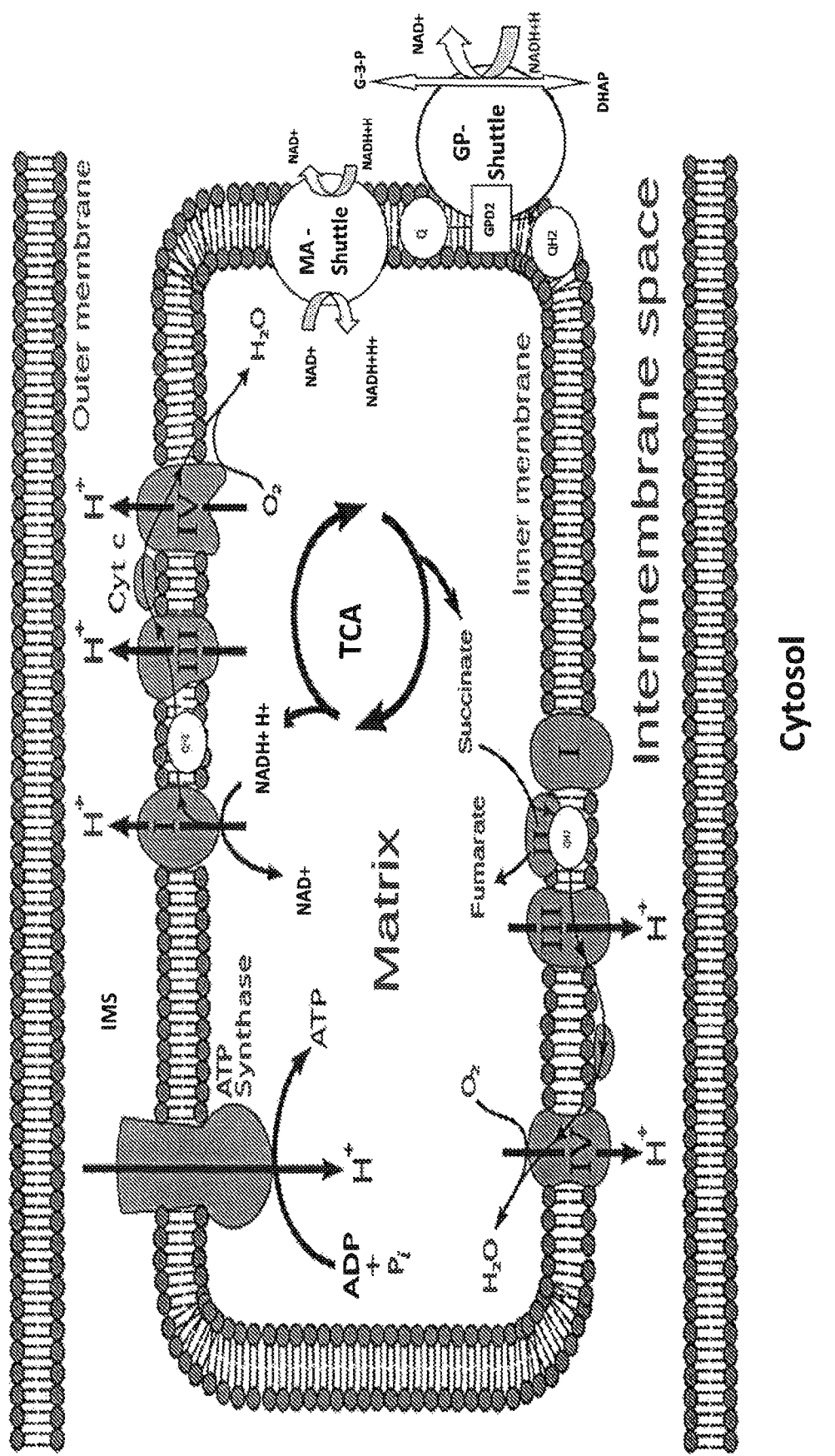
FIG. 1a depicts the structure of mitochondrial electron transport system (ETS) on the inner mitochondrial membrane (IMM) and the location of the citric acid cycle (TCA) and ATP synthase inside the mitochondrial matrix. Final catabolism of carbohydrates and fatty acids and carbohydrate parts of amino acids into carbon dioxide ($CO_2$) and water ($H_2O$) occur in the TCA and ETS.

The present invention is based on studies related to enhancing the energy production and the metabolism of fats (lipids) and/or amino acids in cells, and in preventing suboptimal level of carbohydrate catabolism. The improvements are achieved firstly by improving mitochondrial ATP production, and secondly by improving antioxidative state of the cells, e.g. by hindering excessive radical oxygen species (ROS) formation from oxidative phosphorylation (OXPHOS), and thirdly by improving the redox-state, i.e. by increasing cellular capacity to adjust cytosolic $NAD^+$/NADH-ratio in timely manner when needed and, fourthly by the increase of mitochondrial activity and enhanced IMM membrane potentials and their control.

The use of DGA enhances mitochondrial aerobic metabolism in cells and biogenesis of new mitochondria with alleviating effect towards non-communicable mitochondrial diseases. The invention also relates to the use of said compounds in mitochondrial coordination of optimal NAD(P)$^+$/NAD(P)H-ratios in cytosol, cells, tissues/organs and whole physiological systems, e.g. cardiovascular and/or central nervous systems. Further, the invention relates to the use of said compounds in enhancing anaplerotic and anabolic processes like glyceroneogenesis, protein synthesis, and pentose phosphate pathway producing ribose-5-phosphate, the precursor of nucleobases adenine and guanine. Directly related to the above the use of DGA relates also to reducing the formation of reactive oxygen species (ROS) with alleviating effect towards non-communicable diseases related to oxidative damage to DNA, e.g. slowly advancing degenerative diseases and cancer.

The invention is directed to giving cells tools to combat deteriorating redox state during metabolic stress and physical exercise. Simultaneously it enhances antioxidative state of the cells, enhances metabolic flux, and also balances ETS and ATP production. In some physiological states the invention also opens up temporarily a possibility for faster and more sustainable, but also somewhat less efficient, ATP/energy production by the ETS compared to "full" ETS starting from complex I, i.e. GP-shuttles.

Based on clinical gene expression and other studies (Examples 2.2, 2. and 2.4) it seems that the very short term and longer term effects of the use of DGA on aerobic metabolism differ slightly. This due to the fact that the use of DGA causes also structural improvements in energy metabolism that cannot be realized in acute administration because structural changes take time, even though they seem to be surprisingly fast also.

In the short run the biggest and almost immediate improvement achieved by the use of DGA is the increasing cellular capacity to adjust cytosolic NAD$^+$/NADH-ratio. This is due to signal effect (See FIG. 1b below) and by directly providing substrates through glyceroneogenesis to the GP-shuttles. Immediately thereafter and also due to improved cytosolic NAD$^+$/NADH-ratio also MA-shuttles are activated. Aerobic metabolism causes ROS production. The use of DGA can efficiently fight against excessive ROS amount by activating Nrf2/ARE pathways (see FIG. 2).

In the longer run (meaning from already 2-4 days onwards) the main energy metabolism related effect of the use of DGA is the increase in beta oxidation, i.e. enhancement of the metabolism (catabolism) of fats as the energy source. Triglyceride transport through blood circulation is increased, which is a sign that the heart, skeletal muscles and some other tissues have increased their use of fatty acids (FAs) as their energy source. It is also reasonable to expect that the de novo synthesis of FAs for the use of cellular energy metabolism is increased. Formed medium chain FAs might possess also other health effects besides on top increased aerobic metabolism and related enhanced ROS control.

It was now surprisingly found that the use of a compound from D-glycerate group i.e. D-glyceric acid, DL-glyceric acid (DLGA), L-glyceric acid (LGA) and/or hydroxypyruvate enhance mitochondrial ATP production, and simultaneously reduce excessive radical oxygen species (ROS) formation from oxidative phosphorylation (OXPHOS), and further more can increase cellular capacity to adjust cytosolic NAD$^+$/NADH-ratio in timely manner when needed. (see Example 2.3.2 for relevant gene expression changes, and Example 2.3.3 for significant changes in blood substrate concentrations due to the use of DGA, and FIG. 6-11 for decline in ROS and increase in ATP use)

Unless otherwise specified, the terms, which are used in the specification and in the claims, have the meanings commonly used in the field of biochemistry, particularly in the field of metabolic or exercise/sports related studies.

The term "D-glycerate group" includes the compounds D-glyceric acid, DL-glyceric acid, L-glyceric acid and hydroxypyruvate and their salts and esters and derivatives.

The term "subject in need" refers to humans and animals. The composition of the present invention is useful for enhancing metabolism in subjects in need. The composition is suitable for use in humans. The composition is also suitable for animals.

DGA is a weakly acid compound that is readily soluble in water and alcohol and can be prepared e.g. by oxidation of glycerol. DGA can be liberated from its commercially available calcium salt form by simple treatment with dilute hydrochloric acid. Being an organic acid, DGA is also capable of forming esters. DGA can be liberated from its esters, for instance, by esterase enzymes. In the human body, these enzymes are present in the wall of small intestine where they split esterified nutrients into a form that can be adsorbed from the digestive tract. DGA is typically not directly involved in the normal growth, development or reproduction of an adult organism. Unlike its phosphorylated forms (phosphoglycerates) DGA is not produced in bigger amounts during normal sugar catabolism in the human body. Only very small amounts of DGA have been found in the body (Hoffman et al. 1993). LGA is biologically relatively inactive enantiomer. Nevertheless it can be converted into HPA in the body and thus can possess beneficial properties of the innovation. DLGA is racemic form of DGA and LGA. HPA is oxidized form of DGA. HPA can also be formed from L-serine and pyruvate. In this reaction one alanine and one HPA molecule is formed.

The invention is described in detail below with reference to the Figures.

FIG. 1a describes mitochondrial metabolism. Final catabolism of carbohydrates and fatty acids (and carbohydrate parts of amino acids) into carbon dioxide ($CO_2$) and water ($H_2O$) occur in the mitochondrial TCA and ETS. FIG. 1 furthermore depicts malate-aspartate (MA)-shuttle and glycerol phosphate-shuttle (GP-shuttle). These shuttle mechanisms are needed because IMM is impermeable for NADH and NAD$^+$. MA-shuttles transport NAD$^+$ from the matrix to the inter membrane space (IMS)/cytosol. GP-shuttles are located on the outer side of IMM and donate electrons from cytosolic NADH directly to the ubiquinol (QH2) in the ETS and simultaneously increase cytosolic NAD$^+$-pool by one NAD$^+$. On top of being electron carrier in the ETS ubiquinol is a potent lipophilic antioxidant capable of regenerating other antioxidants such as alpha tocopherol (Vitamin E) and ascorbate (Vitamin C).

MA-shuttles are the predominant shuttle mechanism in mammalian cells. They work basically on continuous, demand driven basis to keep cytosolic NAD$^+$ at sufficient levels to allow e.g. normal flow of glycolysis. Mechanism of action of MA-shuttles is relatively slow due to complicated mechanism of action. By increasing pyruvate concentration in the cells the use of DGA can enhance functioning of MA-shuttles. The use of DGA activates also GP-shuttles that consist of membrane bound mitochondrial glycerol phosphate dehydrogenase (GPD2) and cytosolic glycerol phosphate dehydrogenase (GPD1). GDP2 oxidizes glycerol phosphate (G-3-P) into dihydroxyacetone phosphate (DHAP) and simultaneously reduces one flavin dinucleotide FAD into FADH2. GDP2 further oxidizes created FADH2 back to FAD by simultaneous reduction of ubiquinone (Q)

to ubiquinol (QH2) in a hydrophobic reaction. In IMS/cytosol GPD1 reduces DHAP back to GP3 and simultaneously oxidizes cytosolic NADH +H$^+$ into NAD$^+$.

Figure 3:
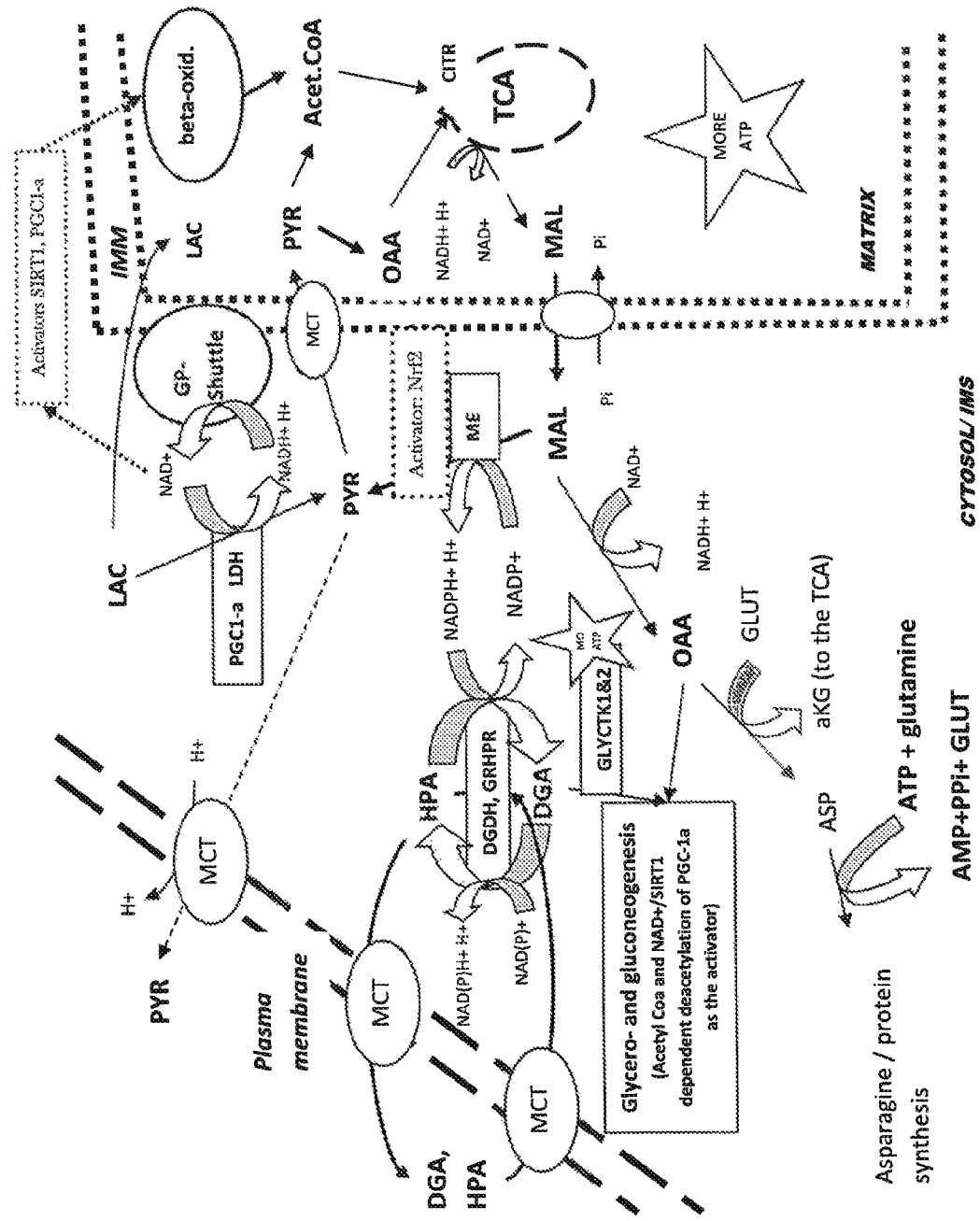
FIG. 3a is a schematic representation of some important reactions that the use of DGA facilitates during fasting. Abbreviations: Gene related to complex III (MT-CYB), MT-CYB=Ubiquinol Cytochrome c Reductase; Gene related to complex IV (COX1), COX1=mitochondrially encoded cytochrome c oxidase I; ME, malic enzyme; MCTs, monocarboxylate transporters; LAC, lactate; aKG, alfa-ketoglutarate; ASP, aspartate.
FIG. 3b is a schematic representation of some important reactions that the use of DGA facilitates during fed state. Abbreviations: CIC, mitochondrial citrate iso-citrate carrier; GLUC, glucose; GLUT4, glucose transporter 4; IR, insulin resistance; ROS, radical oxygen species; G-6-P, glucose-6-phosphate; GSH, glutathione; SOD2, superoxide dismutase.
FIG. 3c depicts the involvement of mitochondria in cell death caused by NMDA stimulation (excitotoxic insult) in neurons. Source of the graph: M. Flint Beal, *Energetics in the pathogenesis of neurodegenerative diseases*. Trends in Neuroscience, Volume 23, Issue 7 pp. 279-33, 2000. Abbreviations: NMDA receptor, N-Methyl-D-aspartic acid receptor; Cytc, cytochrome c; NOS, (neuronal) nitric oxide synthase; NO, nitric oxide; ONOO$^-$, Peroxynitrite.
FIG. 3d depicts one mechanism of action of the DGA and/or HPA use in red blood cells (RBC or erythrocytes). Abbreviations: 3-P-GA, glyceraldehydephosphate; 1,3-BPG, 1,3-bisphosphoglycerate; 2,3-BPG, 2,3-bisphosphoglycerate; BPM, bisphosphoglycerate mutase.
Figure 3:
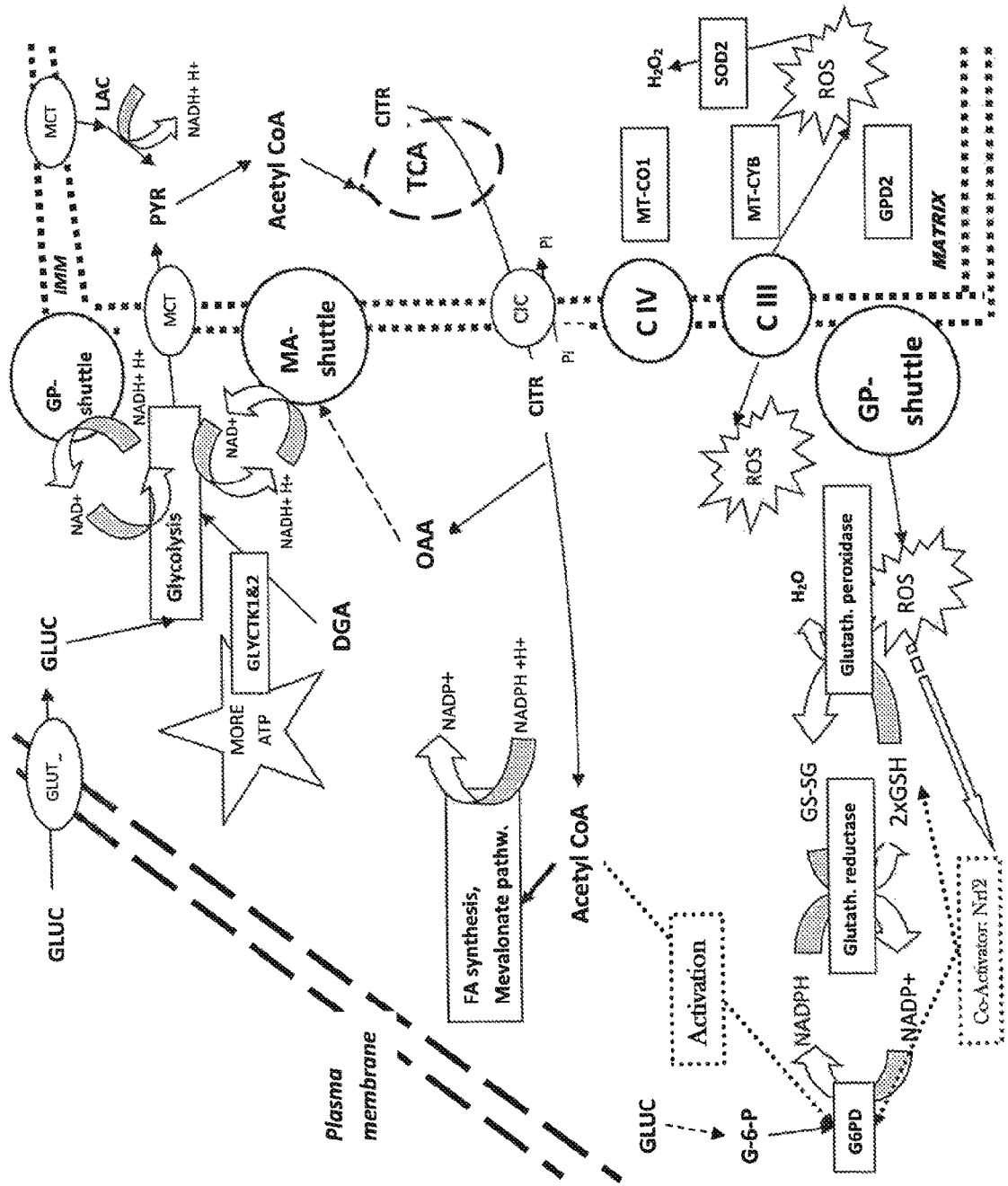
Figure 3:
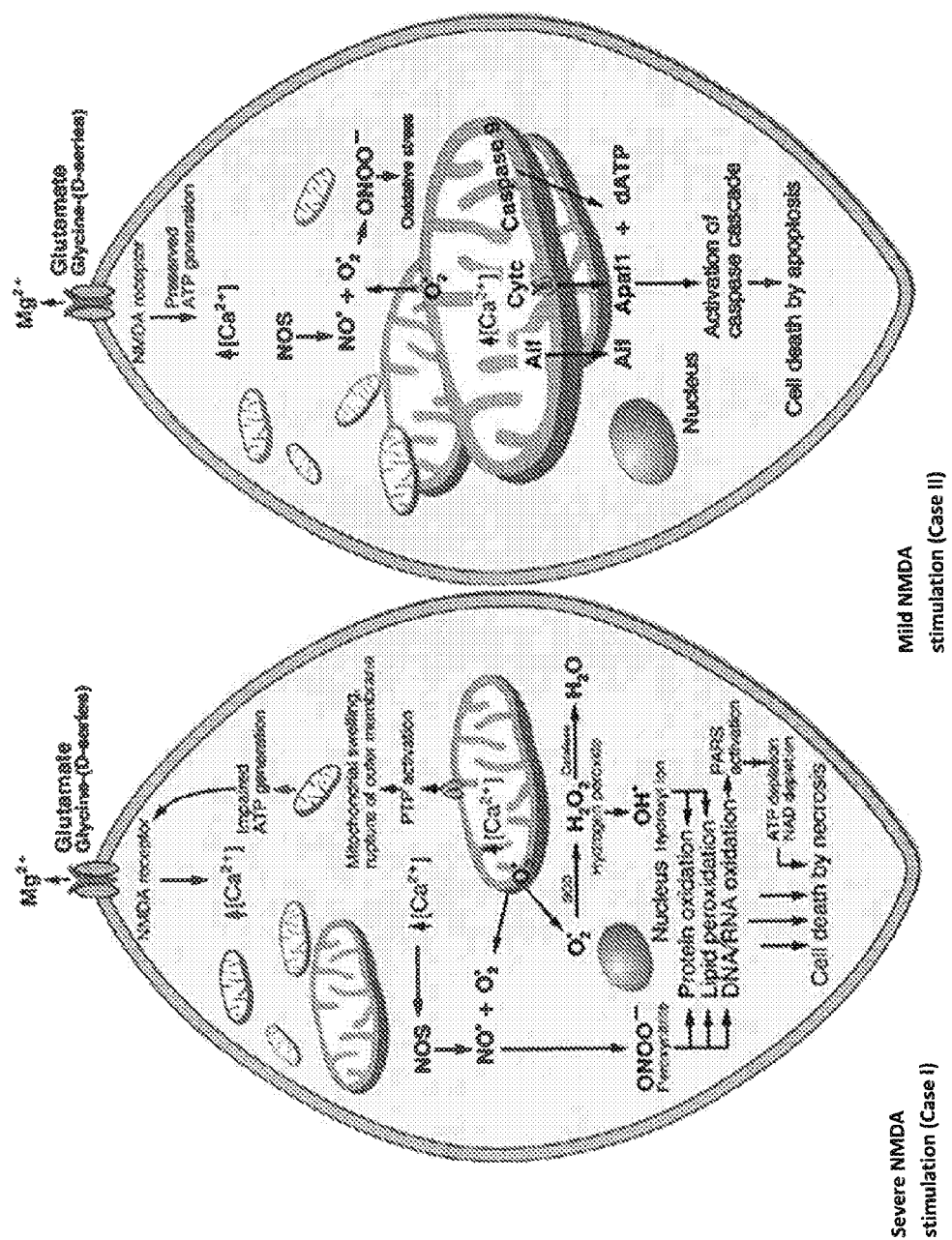
Figure 3:
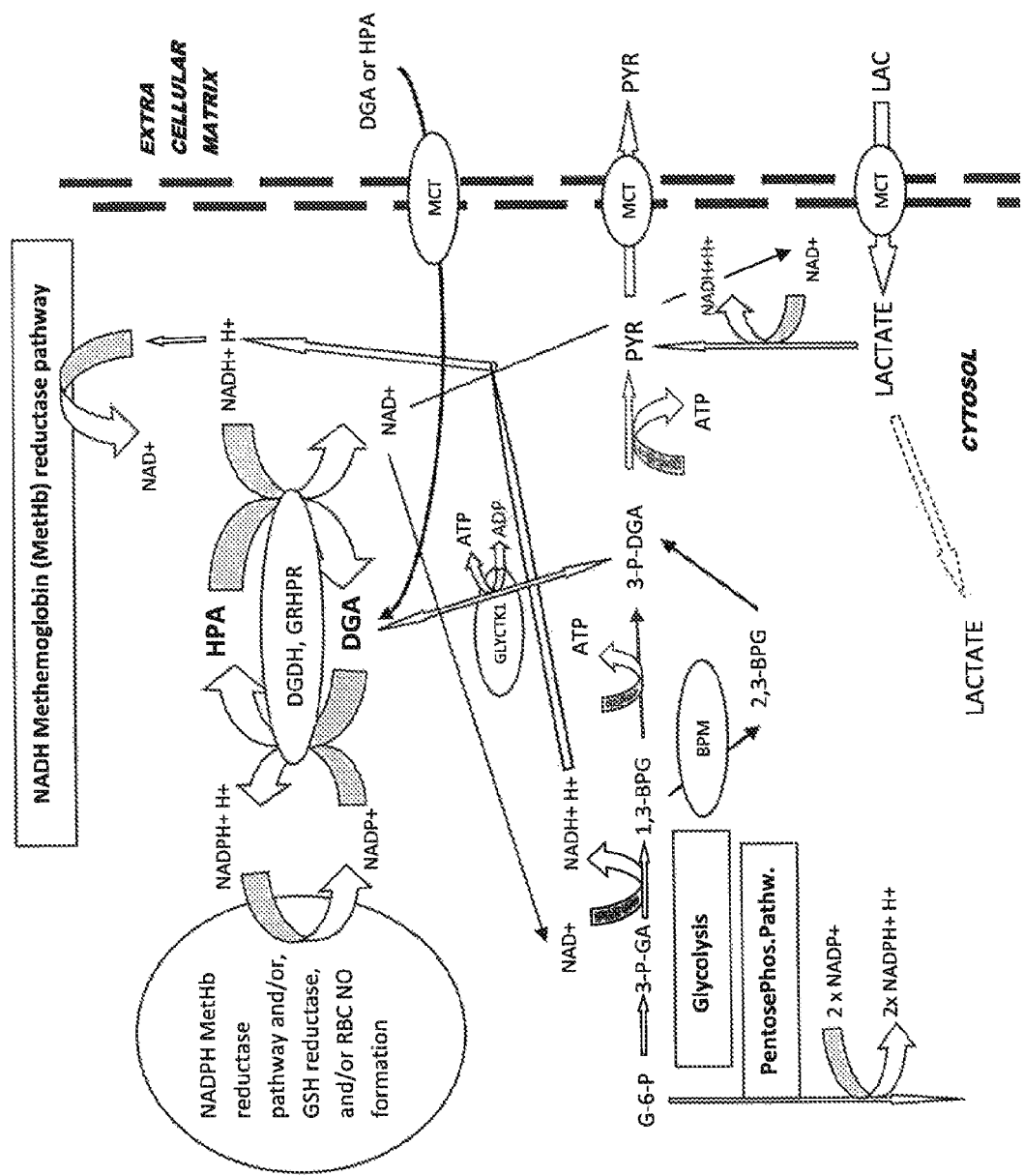

GP-shuttle is irreversible. MA-shuttle is partially irreversible, i.e. the aspartate (ASP) side with glutamate functions only to one direction but malate (MAL) can be interchanged with alfa-ketoglutarate (a KG) or with phosphate also out from the matrix (FIG. 3a). This partially inverted MA-shuttle can export mitochondrial NADH equivalents out from the matrix and thus reduce the pressure towards complex I to oxidize NADH inside the matrix. This happen e.g. in gluco- and glyceroneogenesis situations when oxaloacetate (OAA) from the matrix is exported via malate to the cytosol for re-conversion back to OAA and further to phosphoenolpyruvate (PEP) or to aspartate-asparagine route to protein synthesis (see FIG. 1b and FIG. 3a).

The use of DGA promotes especially glyceroneogenesis (shown e.g. by the increase in PGC-1a, in blood triglycerides and pyruvate). The rise in MA-shuttle intermediates arises from increased pyruvate formation (Example 2.3.3). In some situations, e.g. in intensive exercise glycolysis produces excessive amounts of NADH in short time or glycolysis is inhibited by lack of NAD$^+$. In these situations it is beneficial 1) to rapidly oxidize part of the NADH outside of the mitochondrial matrix like GP-shuttles do, and 2) that also MA-shuttles function efficiently. The present Invention provides that GP-shuttle mechanisms can possibly exist also in other cell membranes than in mitochondrial ones.

Figure 1B:
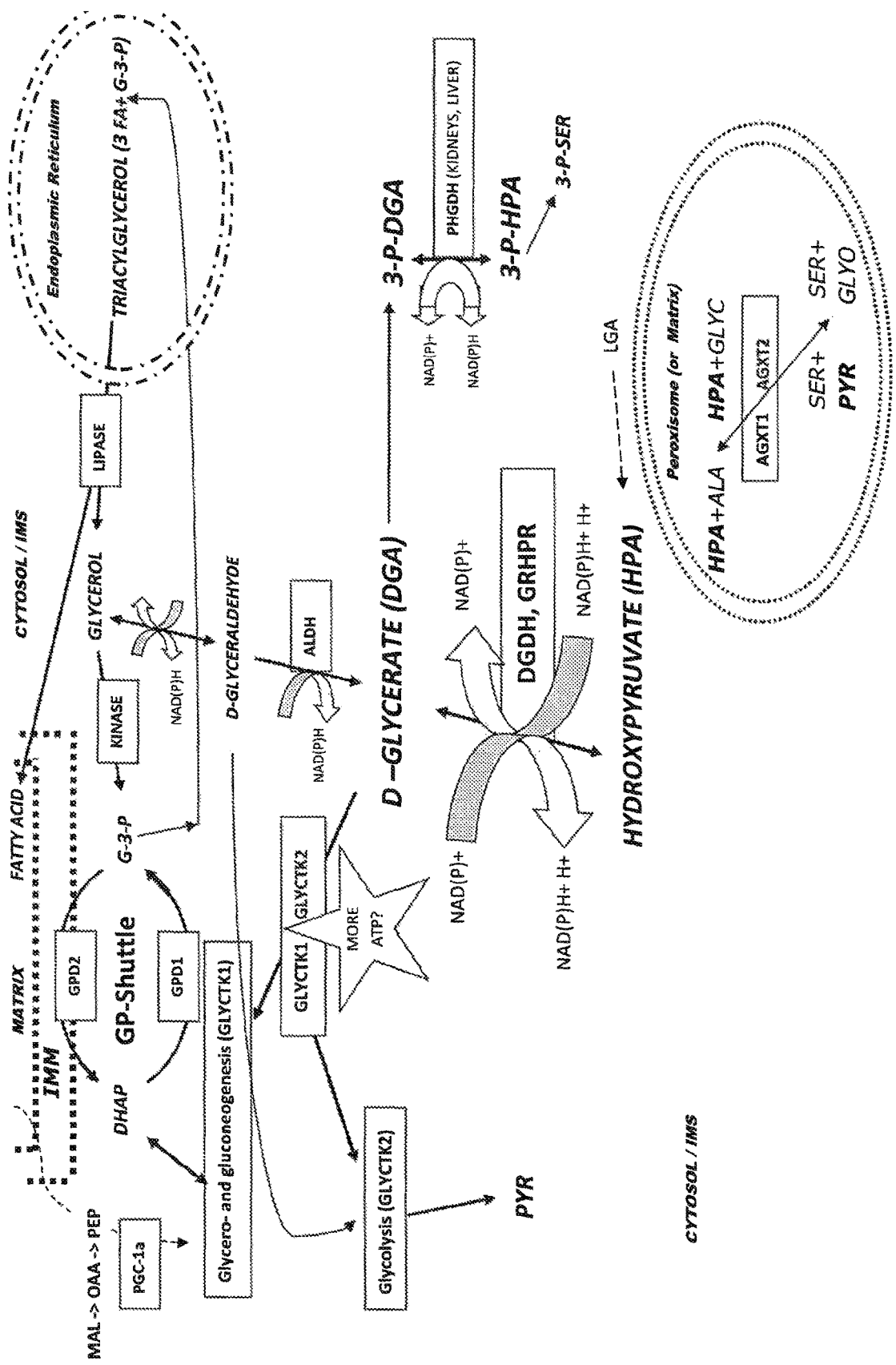
FIG. 1b depicts some important metabolic routes for D-glycerate (DGA) and hydroxypyruvate (HPA). Reactions catalyzed by D-glycerate dehydrogenase (DGDH) and hydroxypyruvate reductase (GRHPR) occur in cytosol/IMS and likely also in some other favorable spaces in other cell organelles or compartments but not in the mitochondrial matrix. Cytosolic location applies also to D-glycerate kinases (GLYCTK1, GLYCTK2) that relate DGA directly to major cytosolic pathways, i.e. glycolysis and gluco-/glyceroneogenesis. Abbreviations: GDP2, mitochondrial glycerol-phosphate dehydrogenase; GDP1, cytosolic glycerolphosphate dehydrogenase; GLYCTK1, Glycerate 1-kinase; GLYCTK2, Glycerate 2-kinase; DGDH, D-glycerate dehydrogenase; GRHPR, glyoxylate/hydroxypyruvate reductase; AGXT1,2, alanine-glyoxylate aminotransferase 1 or alanine-glyoxylate aminotransferase 2; PYR, Pyruvate; OAA, oxaloacetate (OAA); PEP, phosphoenolpyruvate; MAL, malate; SER, L-serine; GLYO, glyoxylate; GLY, glycine; 3P-DGA, glycerate phosphate; 3P-HPA, hydroxypyruvate phosphate; 3P-SER, serine phosphate.

FIG. 1b describes signaling and related metabolic pathways. As seen in Examples 2, 3.2, and 5, DGA administration can increase aerobic metabolism significantly and the effect is almost immediate. Furthermore, this effect is sustained also in the longer run (4 days, 3 weeks and even for 8 weeks). This is very likely due to some enzyme activation in correct location of the cytosol and/or IMS that gives a strong signal for cells to activate aerobic metabolism and related vast set of health benefitting effects (see FIG. 2). Without clear signaling effect it is impossible to explain how relatively small DGA (or HPA) administration could induce strong ETS gene activation, antioxidant defense activation, increase in triglyceride synthesis and simultaneous increase in pyruvate and decrease in lactate levels. Further DGA and HPA can directly complement the activation of aerobic metabolism because they themselves provide right substrates for the initiation of e.g. glyceroneogenesis, and the TCA cycle via pyruvate increase, like seen in FIG. 1b.

Most probable candidate for the location dependent signaling is the activation of GLYCTK1 and/or GLYCTK2 enzymes in the main direction of DGA and HPA metabolism. High and prolonged ATP demand, like seen e.g. in endurance exercise, likely activates GLYCTK1 and/or GLYCTK2 genes (that can yield ATP). That is likely also why DGA and/or HPA administration is able to activate mitochondrial aerobic energy metabolism, including beta oxidation. At the same time, it should be noted that complex cell signaling network can also require initial activation or even deactivation of some other related enzymes or pathways, e.g. D-glycerate dehydrogenase (DGDH) and glyoxylate/hydroxypyruvate reductase (GRHPR). Additionally aldehyde oxidase (AOX1) can be involved in this cellular process. (AOX1 is not presented in the graph but it is activated as part of the Nrf2/ARE system, see Example 2.3.2 and FIG. 2.) Activation can involve also some relevant candidate from vast aldehyde dehydrogenase (ALDH) family, and/or increased peroxisomal or ER gene activity. Whatever the signal mechanism is, the use of the use of DGA initiates similar, very health promoting mechanisms that can be associated with long term aerobic exercises. But additionally, because of formed extra pyruvate is not consumed, there is clearly even more benefits to be gained for vast amount of therapy areas then simply from initiating long term exercises. Also therapeutic use of e.g. HO-1 (Nrf2/ARE) up and down regulation gives numerous therapeutic possibilities for the use of DGA (more on HO-1 in FIG. 2 and gene expression studies, Examples 1.3 and 2.3.2).

Presented feedback mechanism between DGA and HPA likely further enhances the positive activation effects of various NADH and NADPH dependent oxidation-reduction-reactions by the use of DGA and/or HPA. DGA-HPA-loop is due to the fact that DGDH and GRHPR can utilize both NADH and NADPH as co-substrates in oxidation-reduction-reactions and even to both directions in FIG. 1b. Favored reaction directions of these enzymes are as mentioned in the names of the enzymes. DGDH favors NAD+ as a co-substrate and GRHPR favors NADPH. From the "DGA-HPA loop" cells get additional tools to balance NAD$^+$/NADH-ratio (energy metabolism)—and importantly also NADPH/NADP+-ratio (antioxidant defense and anti-inflammatory control) (see FIG. 2 and FIG. 4). DGA-HPA loop is likely an important factor in observed efficacy of the use of DGA and/or HPA in longer term administration, but the use of DGA and/or HPA does not provide (or need) that DGA and/or HPA carbon skeletons shuttle on average multiple times between DGA and HPA.

Direction from DGA towards D-glyceraldehyde (D-GALD) is not favored due to the fact that ALDH enzyme activity clearly favors direction towards DGA. Additionally ALDH enzymes are typically most active in mitochondrial matrix, i.e. not in cytosol/IMS.

From upper right hand corner of FIG. 1b it can be seen that generated G-3-P that can be used in packaging of fatty acids (FAs) in to triacylglycerides (trigys). Trigys are used in intracellular storage and extra cellular transportation of FAs into tissues. When need arises lipase enzymes liberate FAs to be used in beta oxidation and simultaneously liberated free glycerol can be phosphorylated by glycerol kinase back to glycerol phosphate (G-3-P). G-3-P can be also used in the biosynthesis of phospholipids in the endoplasmic reticulum (ER). ER often has a close physical interplay with mitochondria in cells. Gluco- and glyceroneogenesis requires generally more energy (ATP, GTP and UTP) than glycolysis produces.

Figure 2:
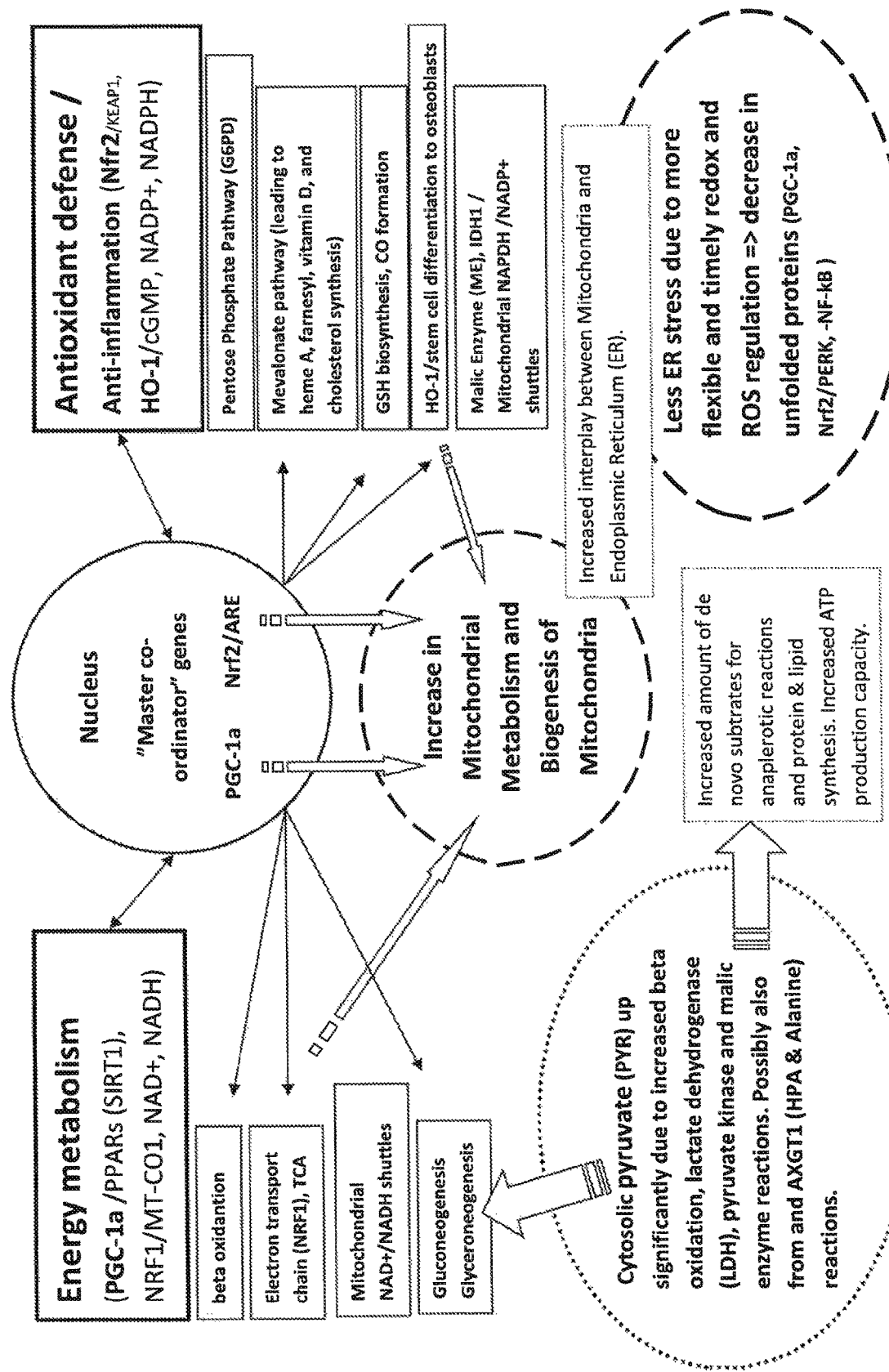
FIG. 2 describes major metabolic pathways that the use of DGA activates. Virtuous cycle of enhanced energy metabolism and endogenous antioxidant defenses with increased mitochondrial activity and mitochondrial biogenesis and increased pyruvate concentration with less ER stress creates wide range of specific and also pleiotropic therapeutic effects that can alleviate, prevent or even heal basically all non-communicable diseases related to dysfunction in energy metabolism, increased ROS formation, and/or unregulated anti-inflammatory disorders. Abbreviations: PGC-1α, Peroxisome proliferator-activated receptor gamma (PPAR-γ) coactivator 1-alpha; Nrf2, nuclear factor-2 erythroid related factor-2; AREs, antioxidant response elements; NRF1, nuclear respiratory factor 1; HO-1, inducible heme oxygenase; SIRT1, sirtuin (silent mating type information regulation 2 homolog) 1; MT-CO1, mitochondrially encoded cytochrome c oxidase I; Keap1, Kelch-like ECH-associated protein 1; NF-kB, Nuclear factor kappa-light-chain-enhancer of activated B cells; PERK, RNA-dependent protein kinase (PKR)-like ER kinase.

From lower right hand corner of FIG. 1b it can be seen that part of the HPA can be converted with alanine (ALA) into pyruvate (PYR) and L-serine (SER). This transaminase reaction materializes typically in peroxisomes using transaminase enzymes (AGXT1 and AGXT2). In some tissues this transaminase reaction can happen also in the mitochondrial matrix and possibly also in the cytosol/IMS. Peroxisomes generate ROS. In the peroxisomes L-serine with glyoxylate (GLYO) can be converted back to HPA and glycine (GLY) the simplest amino acid. Pyruvate can be also converted back to alanine in cytosolic or mitochondrial transaminase reaction with glutamate (not in the graph). In a situation with excess ALA and GLYO this HPA-SER-reaction series can convert excess ALA and GLYO into pyruvate and glycine. Transporting mechanisms of alanine and glyoxylate into peroxisomes exist. There are some reports in the literature that very high HPA amounts can be harmful for e.g. glial cells in cell cultures. This is likely due to excessive conversion of HPA and glycine into glyoxylate and L-Serine. Decreased amounts of glycine can be harmful for the functioning of the CNS. This view on the possible cause for HPA toxicity in the CNS tissues has not been reported in the literature before. The amounts of DGA and HPA that are needed in the present invention are clearly lower than possibly toxic amounts of HPA. FIG. 2 describes induced master regulatory genes and pathways. Virtuous cycle formed by the use of DGA of enhanced energy metabolism and endogenous antioxidant defenses with increased mitochondrial activity and mitochondrial biogenesis and increased pyruvate concentration with less ER stress creates wide range of specific and also pleiotropic therapeutic effects that can alleviate, prevent or even heal basically all non-communicable diseases related to dysfunction in energy metabolism, increased ROS formation, and/or unregulated anti-inflammatory disorders.

Additionally the activation of pentose phosphate pathway increases even the production of nucleobases adenine and guanine thus helping the de novo formation of important biological molecules related to DNA formation and energy metabolism. We have shown that even short 12 hour clinical, in vivo administration of DGA increases gene expression of GPD2 in peripheral leukocytes. Genes related to complex III (MT-CYB) and IV (COX1) of the ETS increased statistically very significantly after 4 day administration implying that aerobic energy metabolism and nuclear respiratory factor 1 (NRF1) were activated. The use of DGA can activate cellular aerobic energy metabolism also the expression of PGC-1a increased statistically significantly in leukocytes already after 4 day administration of DGA (in vivo), and in hepatocytes in 2 days (in vitro) compared to zero control. PGC-1a increases mitochondrial biogenesis by activating vast amount of aerobic energy production, i.e. oxidative phosphorylation, related genes. To confirm the case of increased aerobic mitochondrial metabolism by the use of DGA, plasma lactate has been shown to decrease by more than 30%. This is a very remarkable and strong indication of enhance oxidative capacity of cells.

PGC-1a has also been associated with increased beta oxidation and glyceroneogenesis. Furthermore PGC-1a has been associated with reduced ER stress. PERK (=RNA-dependent protein kinase (PKR)-like ER kinase) is a key ER stress sensor of the unfolded protein response, is uniquely enriched at the mitochondria-associated ER membranes. Activation of PERK in unfolded protein response situation is necessary and sufficient condition on Nrf2/Keap1 dissociation and subsequent nuclear import.

Heme oxygenase-1 (HO-1) expression is strongly activated after 4 days with higher doses of DGA but notably smaller doses of DGA can also down regulate the activity of HO-1 after 4 day administration (see Example 2.1) and also in 12 h after first doses (Example 2.3.2).

Use of DGA increases blood pyruvate levels 20-25%. In literature increased pyruvate concentrations have been inter alia shown to alleviate and, when needed, also activating inflammatory responses mediated by NF-kB, a pro-inflammatory transcription factor.

The use of DGA can efficiently enhance the in vivo activity level of antioxidant and anti-inflammatory defenses of the cells, and simultaneously improve oxidative and inflammatory status of cells, tissues, organs and whole physiological systems. The improvement in status is followed from enhanced endogenous energy production and notably increased supply of exogenous energy fuel for certain tissues especially in brains and elsewhere in the CNS in the form of pyruvate. The use of DGA provides even several adjacent and independent mechanisms that produce and/or activates pleiotropic therapeutic events thus ensuring that some positive therapeutic effect will be materialized in all subjects in need.

Rate limiting enzyme of the pentose phosphate pathway (G6PD) is activated rapidly i.e. in 12 h after first administration. The expression of G6PD remains at high levels compared to the zero control also after 4 days. HO-1 expression is strongly associated with Nrf2 as well as G6PD gene also. In the nucleus Nrf2 binds to antioxidant response element (ARE) that initiate antioxidative genes, e.g. G6PD and Ho-1, transcription, and also many mitochondrial transcription factors.

Like PGC-1a, also Nrf2/ARE promotes mitochondrial biogenesis. Nrf2/ARE activates antioxidant defenses of the cells by e.g. activating genes related to mitochondrial NADPH-shuttles including malic enzyme and cytosolic isocitrate dehydrogenase (IDH1). These NADPH-dependent channels also play a pivotal role in activated antioxidant defenses by generating NADPH form $NADP^+$. Clear in vitro results with human primary hepatocytes showing that DGA administration can sharply reduce ROS levels further supports the relationship that DGA administration significantly increases antioxidant Nrf2/ARE-pathway. Separate in vitro results from rat cortical neurons show increased mitochondria biogenesis after 4 day administration of DGA. Positive test results in peripheral leukocytes, neurons and hepatocytes support the idea that both PGC-1a and Nrf2/ARE are activated by DGA in all cell types that use mitochondrial energy metabolism as their primary source of energy.

FIG. 3a relates to fasting state. Fasting and resting state, e.g. during the night and DGA or HPA administration before going to bed, is very favorable for beneficial anabolic and anaplerotic actions of the DGA use (on top of the activation of Nrf2 and PGC-1a/NRF1 pathways). In fasting DGA administration increases 1) glyceroneogenesis that provides substrates to the GP-shuttle (and seen as an increase in GP-shuttle activity in gene expression), 2) beta oxidation that is inter alia indicated by significant increase in glycerol and pyruvate levels (see Examples 5 and 2.3.3), and 3) activity of MA-shuttles and the TCA (due to increase in pyruvate). In the longer run more permanent increase in beta oxidation leads to enhanced intracellular triglycerides formation and lipase activity in tissues e.g. in muscle cells (like in example 5). In the short run increased demand for triglycerides in muscles is provided mostly by the liver, and seen as a temporary increase in blood triglycerides levels (Examples 2.1., 2.2 and 2.3.1).

DGA can facilitate enhanced NADH oxidization into $NAD^+$ and thus e.g. lactate (LAC) conversion into pyruvate (PYR). In Feedback effect from HPA back to DGA can activate e.g. malic enzyme (ME) that converts malate (MAL) into pyruvate. ME on the other hand is related to Nrf2/ARE nuclear transcription factor. Formed excess amount of pyruvate can be rapidly used as redox-regulator (reaction back to lactate), or in energy production through TCA and/or in fatty acid synthesis and/or gluco-/glyceroneogenesis, and further even into protein synthesis via OAA. Cytosolic OAA can be used in gluco-/glyceroneogenesis or be transaminated with glutamate (GLUT) into alfa-ketoglutarate (aKG) and aspartate (ASP). Aspartate with glutamine and ATP can be further converted into asparagine and glutamate and AMP+PPi. (Glutamine is formed from glutamate and ammonia using one ATP into ADP+Pi, not in the graph.) Energy needed for these anabolic reactions in this fasting state is provided typically by beta oxidation. As an example related to increased glyceroneogenesis, healthy and/or trained skeletal muscle cells start to form increased amounts of triglycerides close to mitochondria from glycerol phosphate and fatty acids as an efficient energy source for future mitochondrial beta oxidation. On the protein synthesis side more energy needing asparagine has been reported to be a superior building block for functioning proteins compared to e.g. glutamine. All in all, enhanced energy production by the use of DGA facilitates healthy metabolism.

Dotted line implicating pyruvate net export from the cells through MCTs (monocarboxylate transporters) happens in bigger scale only in glycolytic cells that can't further use pyruvate in their energy metabolism. These cells include e.g. red blood cells (RBC), glycolytic oligodendrocytes and some other glial cells, and additionally glycolytic myocytes. Those cells have totally or partially lost their mitochondrial activity and have been specialized in some important support role for other cells and tissues, like oxygen transport for RBCs or support of axonal integrity in the CNS. By being able to provide NAD+ and NADPH simultaneously and repeatedly the DGA-HPA-loop can enhance glycolysis and thus ATP and pyruvate production of also glycolytic cells, and simultaneously enhance the antioxidant defense of these those cells. The effect of the use of DGA to energize neuronal axons possesses positive effect in preventing and alleviating e.g. neurodegenerative diseases. It is possible that headache, the only withdrawal effect seen thus far in Examples 2.1, 2.2 and 2.3, is a cause of neurons getting used to better energetic environment with the use of DGA. Outside of the blood-brain-barrier the significant increase of blood pyruvate concentration by the use of DGA implies significant average increase of intracellular pyruvate concentration due to automatic balancing of excessive concentration gradient over plasma membrane by the monocarboxylate transporters (MCTs). In literature administration of pyruvate in various forms e.g. as pyruvate salt or as ethyl pyruvate has been associated with several beneficial effects including an increase in activity of the Nrf2/ARE mediated pathways. As shown by the Example 2.1 and 2.2 the use of DGA can bring similar positive therapeutic effects in vivo and with relatively low DGA administration.

Worth noticing also is that in cerebrospinal fluid (CSF) of healthy individuals the concentration of DGA is clearly higher than in blood (Hoffman et al) implying that DGA has a role in normal healthy CNS metabolism. Clear concentration gradient across the BBB, implies that there exists some kind of monocarboxylate transporting mechanism across the BBB for DGA that notably prevents passive diffusion from CSF to the blood.

FIG. 3b relates to fed state. In fed state blood glucose (GLUC) levels typically increase and in healthy individuals blood insulin levels rise. Insulin initiates complex process in which inter alia certain glucose transporters (GLUT4) are transported to the cell surface. GLUT4 are insulin sensitive glucose transporters e.g. in skeletal muscle, hearth and adipose tissue and to lesser extend also in the CNS. The transportation of GLUT4 needs energy. Insulin, on the other hand, is synthesized in the pancreas within the so called β-cells. Interestingly glucose stimulated insulin secretion (GSIS) is stimulated by mitochondrial citrate iso-citrate carrier (CIC) in β-cells, as well as ATP/ADP ratio and NADPH/NADP$^+$ ratio of the β-cells. The use of DGA facilitates all mentioned GSIS stimulators and thus it is not surprising that the insulin levels in blood seem to increase in fed state by the use of the use of DGA. Accordingly glucose intake by the cells increases.

An additional explanation to increased glucose intake effect of the use of DGA could be the increased production capacity of ATP by the cells. ATP (and UTP) facilitates glucose intake also by converting GLUC into G-6-P or glycogen and thus prolonging inflow of glucose from blood into cells.

Elevated cellular pyruvate (PYR) concentration increases Acetyl Coa level and further more citrate concentration. Increased export of citrate and its cytosolic conversion into Acetyl Coa and OAA is an important step in fatty acid (FA) synthesis and also for so called mevalonate pathway. Increased Acetyl Coa levels can additionally activate also pentose phosphate pathway that can use imported and phosphorylated glucose (G-6-P) for ribose-5-phosphate (R-5-P) synthesis, and also to provide efficient enhancement of cytosolic NADPH/NADP$^+$ ratio in the cells.

Increased aerobic ATP production increases ROS production that is likely one factor activating Nrf2/ARE antioxidant defense mechanisms of the cells by the use of DGA. In literature it is reported that Nrf2/ARE can activate glutathione (GSH) as well as mitochondrial superoxide dismutase (SOD2) production in the cells, and thus facilitate the formation of very efficient endogenous antioxidant defense for cells. As has been mentioned earlier the use of the use of DGA can facilitate ROS scavenging very efficiently compared to zero control in human primary hepatocytes (Example 1.1 and 1.2). The use of DGA provides antioxidant protection also during fasting state. Target use of the use of DGA is against cancer, to almost all degenerative diseases, many auto inflammatory and autoimmune diseases, diabetes, cardiovascular diseases and various myo- and neuropathies related to aerobic energy metabolism and mitochondrial disorders.

FIG. 3c describes neuronal protection in NMDA stimulation (excitotoxic insult) disclosed by Flint Beal M., (Trends in Neuroscience 23: 279-330, 2000): "A severe excitotoxic insult (Case I) results in cell death by necrosis, whereas a mild excitotoxic insult (Case II) results in apoptosis. After a severe insult (such as ischemia), there is a large increase in glutamate activation of NMDA receptors, an increase in intracellular Ca2+ concentrations, activation of nitric oxide synthase (NOS), and increased mitochondrial Ca2+ and superoxide generation followed by the formation of ONOO–. This sequence results in damage to cellular macromolecules including DNA. . . . A mild excitotoxic insult can occur due either to an abnormality in an excitotoxicity amino acid receptor, allowing more Ca2+ flux, or to impaired functioning of other ionic channels or of energy production, which may allow the voltage-dependent NMDA receptor to be activated by ambient concentrations of glutamate. This event can then lead to increased mitochondrial Ca2+ and free radical production, yet relatively preserved ATP generation."

In neurons, that possess very high oxygen and ATP need, lactate is often produced in so called aerobic glycolysis in cytosol as its end product, and then it is shuttled into the matrix through MCT (see FIG. 3b). In the matrix lactate is converted back to pyruvate. This mechanism provides additional shuttle mechanism for shuttling NAD$^+$s into cytosol from the ETS (Complex I and/or the ETS) besides MA- and GP-shuttles. Neurons need excess amounts of NAD$^+$-shuttling capacity form mitochondria probably because they rely mainly on glycolysis in their energy production. The use of DGA can enhance NAD$^+$ shuttling capacity and thus it can alleviate or even heal especially dysfunctions related to the energy metabolism in the CNS (e.g. basically all neurodegenerative diseases but also epilepsy, bi-polar disorder etc.).

The use of DGA has been shown in vitro to protect rat cortical neurons against excitotoxic insult caused by NMDA stimulation (see Example 3.1). Excitotoxicity may be involved in spinal cord injury, stroke, traumatic brain injury, hearing loss (through noise overexposure or ototoxicity) and in neurodegenerative diseases of the central nervous system (CNS) such as multiple sclerosis, Alzheimer's disease, amyotrophic lateral sclerosis (ALS), Parkinson's disease, over-rapid benzodiazepine withdrawal, and also Huntington's disease. One explanation for the protection against excitotoxic insult is increased ATP production by the use of DGA. ATP facilitates calcium storage into ER and also its efflux out of the neuron by ATP dependent plasma membrane $Ca^{2+}$ ATPase. Increased ATP production is important facilitator in neutralizing of excess calcium levels but $Ca^{2+}$ ATPase is not very fast exporter of calcium and thus neurons need also so called $Na^+/Ca^{2+}$ exchangers for rapid clearance of excessive cytosolic calcium that can cause cell death. On top of rapid ATP production neurons need also glial cells in their adjustment and protection against external and internal stresses. According to current understanding close interplay between astrocytes and neurons in the CNS give neurons the protection by the Nrf2/ARE system e.g. against NOS induced cell damage (see FIG. 4 and Example 3.1 for further information). Also increased mitochondrial biogenesis (shown in Example 3.2) can facilitate calcium regulation and protect against excitotoxic insult.

In the CNS increased expression of PGC-1a can also limit beta-amyloid formation that is considered one major reason for Alzheimer's disease (AD). In the literature it is shown that peripheral leukocytes can give good indication on e.g. pathological development in AD. In vivo clinical experiments have indirectly shown that the use of DGA can efficiently alleviate normal metabolic challenges in the CNS in healthy volunteers, because mild but clear negative effects like headache have been reported after stopping the use of the use of DGA. DGA probably cannot freely cross the blood brain barrier but instead uses similar transporting mechanisms as pyruvate and other small carboxylic acids. Interestingly it has been shown in literature that pyruvate can alleviate glucose deprivation induced increase in beta amyloid formation in the brain tissue. The use of DGA can increase pyruvate concentration in blood in fasting and fed states.

In vitro neuronal cell culture studies are often done without ample amounts glial cells like astrocytes in the culture. This means that e.g. Nrf2/ARE antioxidant protection mechanisms provided almost solely by astrocytes in the brains are often missing to a large extent from these study set ups. Astrocytes have been shown also to provide lactate and pyruvate for neuronal ATP production by oxidative phosphorylation.

FIG. 3d depicts one mechanism of action of the DGA and/or HPA use in red blood cells (RBC or erythrocytes). Mature RBC lack mitochondria, nucleus and basically all other cell organelles that are replaced by hemoglobin molecules. RBCs' main and maybe only major role in an organism is to transport oxygen into tissues and export $CO_2$ with hemoglobin molecules. RBCs have a life span of only some 120 days and thus new ones are being produced some millions every second in adult humans. RBCs produce their ATP energy via glycolysis. Formed NADH molecules can't be used for energy production in the ETS and they are mainly used and converted back to $NAD^+$ in NADH dependent methemoglobin reductase pathway that converts methemoglobin into hemoglobin by oxidizing its iron molecule into $Fe^{2+}$. This critical conversion makes it possible for hemoglobin to bind oxygen. Important to notice that also NADPH can be used in different kind of methemoglobin reductase reactions (also presented in FIG. 3d). Due to lack of mitochondria, it is especially important to keep NAD+ and NADPH producing mechanisms active and functioning in RBCs. NAD+ is needed for ATP production and NADPH for antioxidant defenses. Major source of NADPH molecules in RBC is the pentose phosphate pathway. In the literature it is shown that both enzymes DGDH and GRHPR are active in RBCs. One NADPH (or NADH) can be produced when moving from DGA to HPA, and $NAD^+$ ($NADP^+$) when moving back to DGA from HPA. The invention activates DGA-HPA-31 loop reactions in the RBCs and makes balancing of $NAD^+/NADH$ and $NADPH/NADP^+$-ratios more efficient. The use of DGA helps RBCs' energy production, antioxidant defense, and hemoglobin integrity (increased viability of RBC is indicated by observed decline in serum LDH in Examples 2.1 and 2.3.1). By enhancing the ATP production of the RBCs and their $NAD^+/(NADH+H^+)$-ratios (=increase in intracellular pH), the invention can increase 2,3-BPG content in the erythrocytes in subjects in need. Importantly 2,3-BPG allosterically increases oxygen releasing capacity of oxygen, this effect can be significant in tissues deprived of oxygen. By enhancing RBC oxygen releasing capacity the invention can likely alleviate hypertension and possibly congestive heart failure and similar disorders. By reducing oxidative damage/increasing NADPH levels, the invention can possibly alleviate symptoms related to G6PD and 6PGD (6-Phosphogluconate dehydrogenase) deficiencies. Because of lack of peroxisomes and mitochondria, the main way out from the DGA-HPA loop (besides direct efflux through plasma membrane) is eventually moving towards glycolysis and towards pyruvate. RBC pyruvate production can increase also due to influx of lactate into RBCs (that is a well-documented fact) and its conversion towards pyruvate. By enhancing $NAD^+$ formation the invention can increase reversed LDH activity of RBCs and efflux of pyruvate into blood stream (as the results of increased blood pyruvate concentration indicate, Example 2.3.3).

Figure 4:
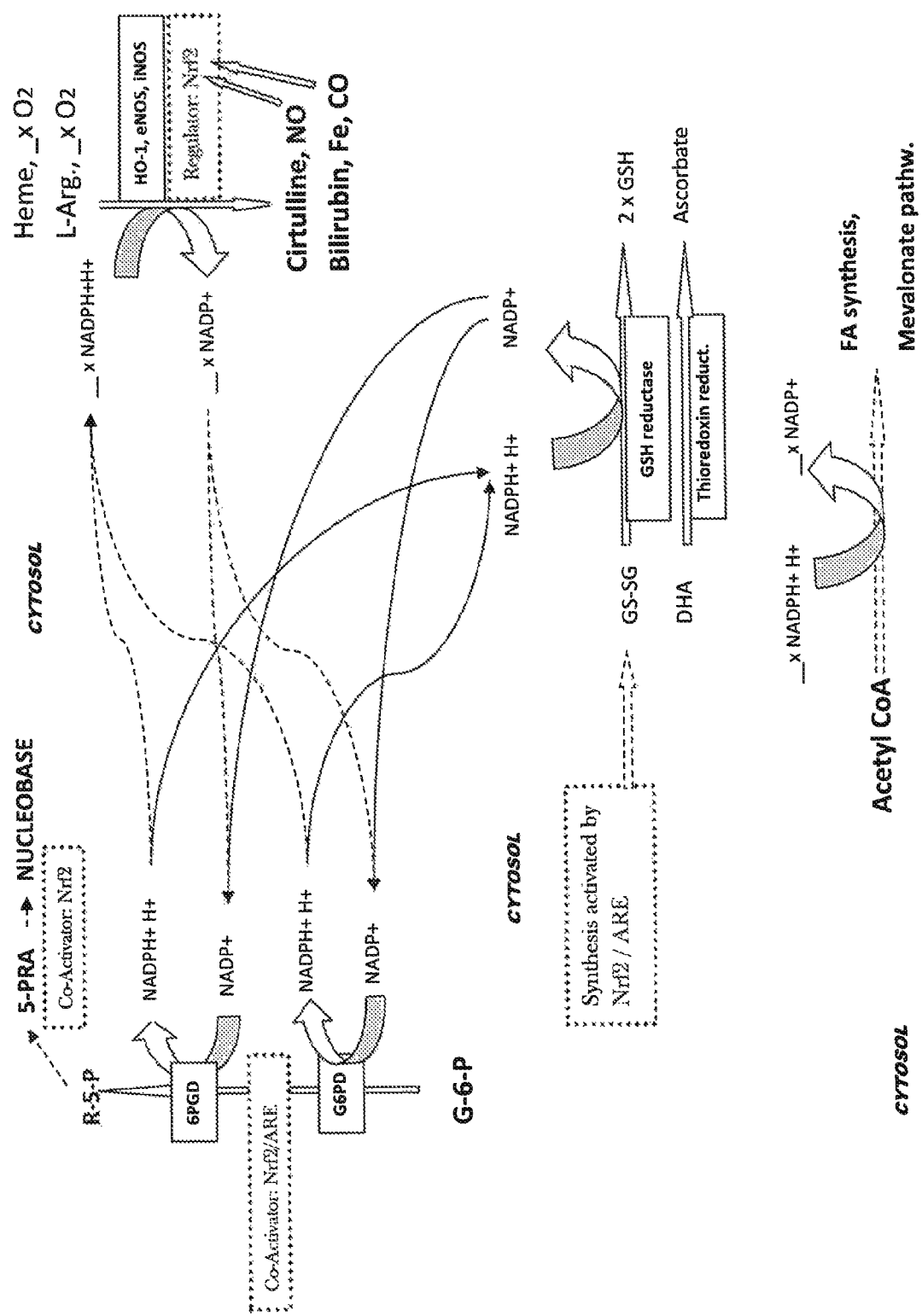
FIG. 4 depicts some of the NADPH dependent pathways that the use of DGA activates and/or can also down regulate. Most of these NADPH dependent pathways and genes are also directly or indirectly related to cellular antioxidant defenses, i.e. Nrf2/ARE related genes and pathways. In general Nrf2 regulated genes can be divided into three categories: (1) antioxidants, (2) anti-inflammatory, and (3) genes related to mitochondrial biogenesis/protection. Abbreviations: G6PD, glucose-6-phosphate dehydrogenase; 6PGD, 6-Phosphogluconate dehydrogenase; NO, nitric oxide; iNOS, inducible NOS, eNOS, endothelia NOS; R-5-P, ribose-5-phosphate; 5-PRA, β-5-phosphorybosylamine; L-Arg, L-arginine; CO, carbon monoxide; Fe, iron; DHA, dehydroascorbate.

FIG. 4 describes NADPH- and Nrf2/ARE related pathways. Most of these NADPH dependent pathways and genes are also directly or indirectly related to cellular antioxidant defenses, i.e. Nrf2/ARE related genes and pathways. The relationship can be e.g. like presented in FIG. 3b where PPP provides NADPH for reducing (activating) glutathione. In general Nrf2 regulated genes can be divided into three categories: (1) antioxidants, (2) anti-inflammatory, and (3) genes related to mitochondrial biogenesis/protection.

In the FIG. 4 there are also some enzymes and reactions that have not yet been directly tested but instead are logically induced by shown effects of the use of DGA, e.g. glucose-6-phosphate dehydrogenase (G6PD) is the rate limiting step of pentose phosphate pathway (PPP) and thus it naturally activates next enzymes in the pathway e.g. 6PGD (6-Phosphogluconate dehydrogenase). Furthermore PPP generates a lot of NADPH that can activate or at least be used as a co-substrate in most of the presented reactions. Other abbreviations in the graph: ribose-5-phosphate (R-5-P), β-5-phosphorybosylamine(5-PRA), L-arginine (L-Arg.), NO=nitric oxide, CO=carbon monoxide, Fe=iron, and DHA=dehydroascorbate. For eNOS and iNOS and their relation with HO-1/Nrf2 see below.

Pentose phosphate pathway (PPP) is up regulated relatively fast already in 12 hours in healthy volunteers. The expression of G6PD the rate limiting enzyme of this important pathway increased statistically significantly in peripheral leukocytes. The reason for this activation can be increased ROS production from aerobic mitochondrial energy production (increase in GPD2, in beta oxidation (acetyl CoA up), and eventually in PGC-1a). ROS scavenging needs NADPH that PPP can supply. Increased ROS production activates also Nrf2 pathway. Nrf2 translocation from cytosol into nucleus activate AREs (=antioxidant response elements) of specific antioxidant defense related genes, like HO-1. The use of DGA can activate HO-1 very strongly, indicating that it can efficiently activate Nrf2 pathway. Also increase in blood bilirubin concentrations have been observed simultaneously after 4.5 day administration of the DGA confirming enzymatic action at substrate level (example 5.3.1 and 5.3.2). Importantly, lower administration of the DGA has also consistently decreased bilirubin levels in healthy and exercising (=mitochondrial metabolism using) volunteers. The use of DGA is planned also for the longer term prevention of diseases and health promotion, and thus it is important that unnecessary activation of cellular defense mechanisms is not turned on all the time. In fact examples 1.1 and 2.1 show that most of the time Nrf2 is down regulated by the use of DGA in humans. Reduced normal ROS levels and simultaneous alert defense systems (with ample ATP energy supply) are the key to longer term health and extended life span.

Figure 12:
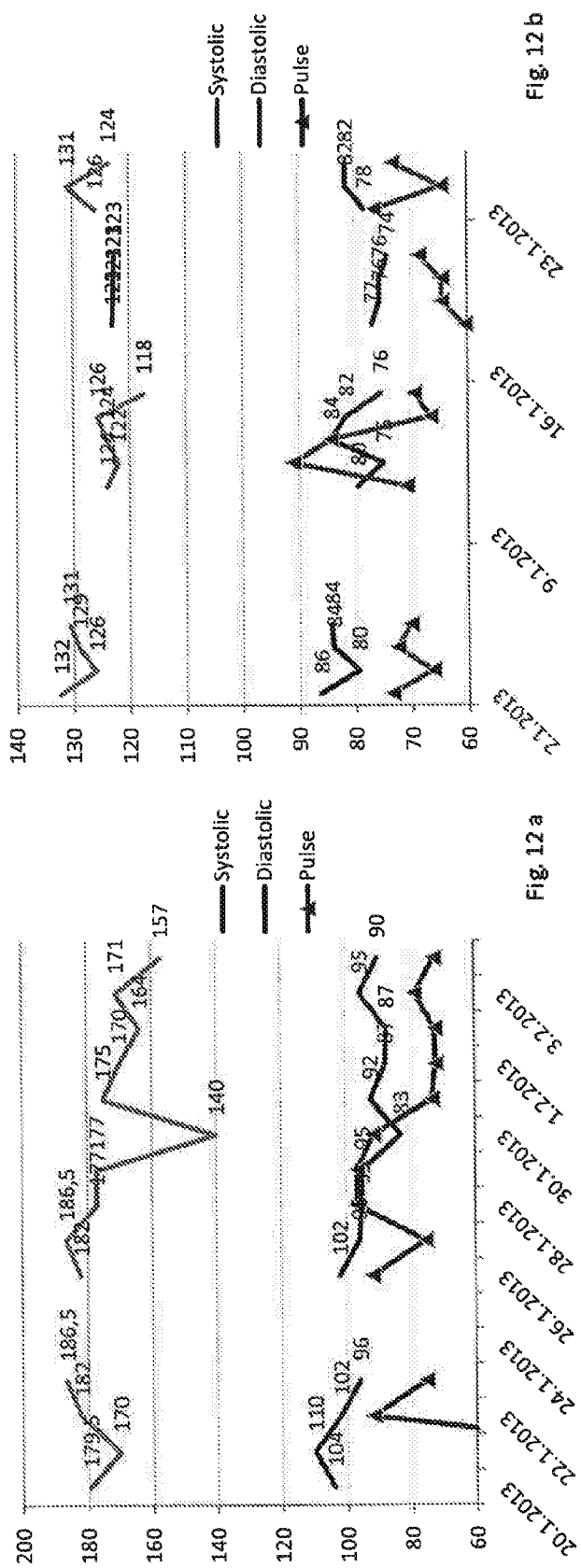
FIG. 12 depicts that hypertension was measured in two study subjects out of eight (subject 4 and 5). Subject 5 was the only person with clearly elevated blood pressure. (For other study subjects 1-3 and 6-8 blood pressures were at normal level.) Subject 5 blood pressure was first observed without any treatment for 6 days (from 20Jan. to 26 Jan. 2013). After that subject 5 received twice a day 4 mg/kg of DGA mixed to water for 10 days. As can be seen in left hand graph during the administration systolic blood pressure was lowered from roughly 180 to some 160, and diastolic blood pressure from 102 to some 90. Subject 4 received 1×4 mg/k/day of DGA for 3 weeks. Her blood pressure declined also somewhat.

It is well known that HO-1 expression and Nrf2/ARE pathway correlate positively. Nitric oxide synthase (NOS) family inducible NOS (iNOS), endothelia NOS (eNOS) and neuronal NOS on the other hand seem to correlate clearly negatively with Nrf2 expression as well as also the NO production does, e.g. Nrf2 activation (in astrocytes) can protect neuronal cells against excessive NO generation in excitotoxity model (see FIG. 3c). Important exception in NO production respect seems to be endothelial cells in which very surprisingly NO production is able to remain at high levels even though Nrf2 clearly depresses eNOS expression. Possible explanation being simultaneous increase in HO-1 expression. (Source: Heiss et al., J Biol Chem. 2009 Nov. 13; 284(46):31579-86, "Nrf2 Contributes to keep eNOS in the coupled state"). From previous it follows that HO-1 and NOS expressions often correlate negatively. This could be a follow up of the facts that 1) the products CO and NO of reactions are complementary in many signaling tasks, and that 2) both reactions use a lot of NADPH as a co-substrate (FIG. 4). Tentatively the use of DGA seems to be able to increase blood NO levels, i.e. activate eNOS, in humans with metabolic syndrome thus contributing to lowered blood pressure (Example 2.3.3). We also know that DGA can reduce blood pressure in subjects in need with elevated blood pressure (FIG. 12). Interestingly in healthy volunteers the use of DGA reduces blood urea levels and as follow up it also reduces blood NO levels (see Example 2.1 and Example 2.3.3).

Nrf2 and NADPH production contribute clearly and positively to the reduced glutathione (GSH) levels of the cells. GSH is readily usable in cells antioxidant defenses. As stated already above increased antioxidant defense capacity from the use of DGA is very clearly visible from e.g. Examples 1.1 and 2.1. Finally NADPH can activate ascorbate (vitamin C) to its reduced state from DHA. Vitamin C is needed e.g. in collagen synthesis. This aspect is relevant for several therapeutic areas (see indication areas below).

A composition which is useful in the present invention comprises one or more compounds selected from the D-glycerate group (D-glyceric acid, DL-glyceric acid, L-glyceric acid, and hydroxypyruvatic acid and salts and esters thereof). Said compounds are for use in a method of enhancing direct and indirect mitochondrial metabolism. Said compounds or a composition comprising one or more of said compounds are also for use in a method of treating or preventing a disease or disorder. The disease or disorder is such as a cardiovascular disease, metabolic syndrome, disorder associated with metabolism, cancer, overweight, elevated blood pressure, or aging process of an organism, but is not limited to said disorders.

The present invention is useful in the therapy areas selected from the following non-limiting groups. Preferably DGA is used.

Cardiovascular diseases: atherosclerosis, myocardial infarction, cardiomyopathy/congestive heart failure, vascular thrombosis and/or embolism, asthma and chronic obstructive pulmonary disease (COPD), G6PD and 6PGD (6-Phosphogluconate dehydrogenase) deficiencies in RBC/hemolytic anemia, lethal sepsis, lethal hemorrhagic shock, and infant jaundice.

Elevated blood pressure/hypertension: primary (essential) hypertension or secondary hypertension, including but non-limited to incidental hypertension and hypoxic pulmonary hypertension.

Disease or disorder related to metabolic syndrome: diabetes, diabetic neuropathy Disorder associated with metabolism: mitochondrial DNA depletion and other mitochondrial diseases, Leigh syndrome, epilepsy, bipolar disorder, psychiatric disorders and mood disorders, cerebrovascular accident, damage from acute head injury, acute or chronic renal failure, acute or chronic liver failure, splenomegaly, acute or chronic pancreatic failure, chronic auto inflammation and autoimmune syndrome and diseases, psoriasis, impairment in collagen synthesis, pre-eclampsia, thyroid disease, chronic fatigue, fibromyalgia.

Overweight

Cancer: cancer subtypes: Basically all types of cancers that are caused by ROS damage to the cell, dysfunctioning mitochondria (e.g. compromised ability for apoptosis) or/and dysfunction of the energy production of the cells can be postponed or even prevented. In some cases a process that endogenously could suppress some tumor is facilitated. In general by alleviating aging related degeneration of the cells, the present invention is useful in reducing the number of malignant cells and/or enhancing their controlled cell death. A skilled person in art is able to select a cancer subtype that can be postponed, alleviated, prevented or suppressed e.g. from the list in National Cancer Institute of US NIH: http://www.cancer.gov/cancertopics/types/alphalist Disease or disorder related to aging of an organism: age related hearing loss, including but not limited to presbyacusis, noise induced hearing impairment, ototoxic hearing impairment), age related macula degeneration, glaucoma, optic neuropathy and ischemic optic neuropathy, retinitis pigmentosa, osteoporosis, osteoarthritis, chronic neurodegeneration, amyotrophic lateral sclerosis, Alzheimer's disease, Parkinson's disease, multiple Sclerosis, Huntington's disease, prion disease.

Pyruvate therapy: the use of DGA can increase plasma pyruvate levels by 25% (shown in Example 2.3.3). An increase in plasma is a direct reflection of similar intracellular pyruvate increase through MCTs. Thus DGA can be used for so called pyruvate therapy (PTh) and even substitute it. In PTh pyruvate is administered orally in salt or ester form. It is well known that administration of pyruvate salt or ester can alleviate, prevent or even heal many diseases and/or disorders such as lethal sepsis, lethal hemorrhagic shock, Leigh syndrome, COPD and other inflammatory diseases, mitochondrial DNA depletion and other mitochondrial diseases. Oral DGA calcium salt can significantly increase endogenous pyruvate production and pyruvate levels in plasma and in the cells; moreover the effect is achieved with very low doses compared to orally administered pyruvate doses needed in PTh.

The composition of the present invention is also useful for enhancing general health and wellbeing of subjects in need.

Furthermore, the composition of the present invention is for use in a method of enhancing oxygen binding of erythrocytes and releasing capacity of hemoglobin (due to increased cytosolic pH due to converting $NADH+H^+$ into $NAD^+$ that increases the production of 2,3-bisphosphoglycerate (see FIG. 3d)). The composition of the present invention is also for use in a method of lowering blood pressure in patients with clearly elevated levels.

In a preferred embodiment of the invention the composition comprises one or more compounds selected from the group consisting of D-glyceric acid, DL-glyceric acid, L-glyceric acid, hydroxypyruvatic acid and their salts and esters, as the only active substance or substances.

In another preferred embodiment of invention the composition consists of one or more compounds selected from the group consisting of D-glyceric acid, L-glyceric acid, hydroxypyruvatic acid and their salts and esters, as the sole ingredient or ingredients of said preparation.

A composition of the present invention comprising one or more compounds selected from the group consisting of D-glyceric acid, DL-glyceric acid, L-glyceric acid, or hydroxypyruvatic acid or their salt or ester is for use in a method of enhancing physical training, performance and recovery from exercise.

The compounds of the present invention enhance aerobic and anaerobic production of energy and enables cells to recover after physical exercise. For example acidosis in skeletal muscle tissues can be moderated by increased redox balancing capacity, i.e. transforming $NADH+H^+$ into $NAD^+$.

A composition comprises one or more compounds selected from the group consisting of D-glyceric acid, L-glyceric acid, hydroxypyruvatic acid and their salts and esters for use as an antioxidant or for use as a medicament having an antioxidant activity.

A composition comprising one or more compounds selected from the group consisting of D-glyceric acid, DL-glyceric acid, L-glyceric acid, and hydroxypyruvatic acid and salts and esters thereof for use in a method of increasing the muscle yield per gram of nutrition and simultaneous decreasing of fat content of humans and animals, and/or alternatively in a method of decreasing nutrition consumption without losing muscle mass of the animals including but limited to live stock (mammals), poultry, and fish.

A composition useful in the present invention may be an oral, topical, parenteral, or inhalable composition for enhancing direct and indirect mitochondrial metabolism comprising one or more compounds selected from the group consisting of D-glyceric acid, DL-glyceric acid, L-glyceric acid, hydroxypyruvatic acid and their salts and esters. The composition or compositions for use in the present invention may further comprise a pharmaceutically acceptable excipient. Suitable conventional excipient and/or carriers which can be used in the present invention are known by the skilled person in the art.

The composition may be preparation in the form of a solution, syrup, powder, ointment, capsule, tablet or an inhalable preparation. The composition may be in the form of a solution suitable for parenteral administration.

The various ingredients and the excipient and/or carrier are mixed and formed into the desired form using conventional techniques. The compositions of the present invention may also be formulated with a number of other compounds. These compounds and substances add to the palatability or sensory perception of the particles (e.g., flavorings and colorings) or improve the nutritional value of the particles (e.g., minerals, vitamins, phytonutrients, antioxidants, etc.).

The composition for use in the present invention may be a part of a beverage, a food product, a functional food, a dietary supplement, or a nutritive substance.

Said beverage, food product, functional food, dietary supplement, supplementary food, or nutritive substance may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. Such optional ingredients may be either naturally occurring or concentrated forms.

In an embodiment the beverage, food product, functional food, dietary supplement, or nutritive substance further comprises vitamins and minerals. In further embodiments, the compositions comprise at least one food flavoring. In other embodiments, the compositions comprise at least one synthetic or natural food coloring.

The composition of the present invention may be in the form of a powder or liquid suitable for adding by the consumer or food producer to a food or beverage. For example, in some embodiments, the dietary supplement can be administered to an individual in the form of a powder, for instance to be used by mixing into a beverage or bottled water, or by stirring into a semi-solid food such as a pudding, topping, spread, yoghurt, sauce, puree, cooked cereal, or salad dressing, for instance, or by otherwise adding to a food, such as functional food.

The handling of excess energy from excess nutrition intake is improved in the present invention. The production of energy from digested food is enhanced. In other words the composition used in the present invention is useful as a diet medicament.

A packaged pharmaceutical preparation useful in the present invention may comprise at least one therapeutically effective dosage form containing D-glyceric acid, DL-glyceric acid, L-glyceric acid, or hydroxypyruvatic acid or their salt or ester.

An embodiment of the present invention is a pharmaceutical composition comprising an effective amount of one or more compounds selected from the group consisting of D-glyceric acid, DL-glyceric acid, L-glyceric acid, and hydroxypyruvatic acid and salts and esters thereof for use in methods according to present invention.

A composition useful in the present invention may be a nutritional preparation for enhancing the metabolism of carbohydrates, fat and/or amino acids comprising one or more compounds selected from the D-glycerate group (consisting of D-glyceric acid, DL-glyceric acid, L-glyceric acid, hydroxypyruvatic acid and their salts and esters).

The present invention is also related to a method of enhancing direct and indirect mitochondrial metabolism in a subject comprising administering an effective amount of one or more compounds selected from the group consisting of D-glyceric acid, DL-glyceric acid, L-glyceric acid, hydroxypyruvatic acid and their salts and esters to a subject in need of enhancing the metabolism of carbohydrates, fats and/or amino acids.

The present invention also relates to a method of enhancing physical training, performance and recovery from exercise, or reducing radical oxygen species with antioxidants in a subject comprising administering a composition comprising an effective amount of one or more compounds selected from the group consisting of D-glyceric acid, DL-glyceric acid, L-glyceric acid, and hydroxypyruvatic acid and salts and esters thereof to a subject in need.

The present invention also relates to a method of increasing the muscle yield per gram of nutrition and simultaneous decreasing of fat content of humans and animals, and/or alternatively in a method of decreasing nutrition consumption without losing muscle mass of the animals including but limited to live stock (mammals), poultry, and fish comprising administering a composition comprising an effective amount of one or more compounds selected from the group consisting of D-glyceric acid, DL-glyceric acid, L-glyceric acid, and hydroxypyruvatic acid and salts and esters thereof to a subject in need. An embodiment of the method comprises administering a pharmaceutical preparation comprising one or more compounds selected from the group consisting of D-glyceric acid, DL-glyceric acid, L-glyceric acid, hydroxypyruvatic acid and their salts and esters, and a pharmaceutically acceptable excipient. An embodiment of the method comprises administering an oral preparation in the form of a solution, syrup, powder, capsule or tablet.

An embodiment of the method comprises administering one or more compounds via a parenteral solution and topical medicament.

Another embodiment of the method comprises administering one or more compounds via a beverage, a food product, a functional food product, a dietary supplement, or a nutritive substance.

The composition is administered to a subject in need at a dose effective in enhancing metabolism. An advantage of the present invention is that the administrable dose is small allowing a convenient dosage to subjects in need. The daily dose in humans may be from 0.1 mg/kg body weight to 20 mg/kg body weight, such as 0.1, 1, 2, 3, 4, 5, 6, 7, 8, 9, 10, 11, 12, 13, 14, 15, 16, 17, 18, 19 or 20 mg/kg, preferably from 3 to 5 mg/kg body weight once or twice a day such as 180 mg-600 mg per day for 60 kg weighing person. In animals the daily dosage per kilogram could be also higher.

The composition may be used in a mixture for enhancing metabolism in a subject in need. The composition is useful for use as a therapeutic agent. The amount of antioxidants is increased in the body. The composition of the present invention is useful as e.g. a complement to vitamins and flavonoids. The decrease of ROS and reduction or stabilizing of blood cholesterol is observed (Table 3). This among several other shown factors leads to improvements in patients suffering from a cardiovascular disease.

Also patients suffering from cancer and metabolic syndrome may benefit from the use of the compositions of the present invention. Another example of a preferable application is use in weight control and reduction.

A useful application of the present invention is in aging process. This is supported by results of in vitro cell studies, wherein significant reduction of the amount of ROS was observed. Also in vivo results support the notion that oxidative stress is reduced (Table 4, bilirubin, urate and LDH), and aerobic energy metabolism is significantly increased (Example 2.3.3). Increased ETS activity and mitochondrial beta oxidation is seen in humans in vivo. Also clear activation of endogenous antioxidant defense mechanisms was seen (Nrf2/ARE pathways).

Glycolysis, Beta Oxidation and Energy Metabolism of the Cells

Fatty acid catabolism involves three stages. The first stage of fatty acid catabolism is beta-oxidation, which occurs in mitochondrial matrix. The second stage is formation of acetyl CoA (FIG. 3a) and its oxidation to carbon dioxide in TCA. The third stage is electron transfer from formed electron carries in the ETS to oxygen. Fatty acid oxidation also occurs in peroxisomes, when the fatty acid chains are too long to be handled by the mitochondria. However, the oxidation ceases at octanoyl-CoA. It is believed that very long chain (greater than C-22) fatty acids undergo initial oxidation in peroxisomes which is followed by mitochondrial oxidation.

In glycolysis in the cytosol of eukaryotic cells, phosphorylated glucose (G-6-P) is converted to pyruvate (PYR), with the net formation of two ATPs and the net reduction of two $NAD^+$ molecules to $NADH+H^+$. ATP is formed by two substrate-level phosphorylation reactions in the conversion of glyceraldehyde 3-phosphate to pyruvate. Pyruvate can enter the mitochondrial matrix and convert to acetyl CoA, and thereafter to enter citric acid cycle (TCA cycle) that also uses $NAD^+$ as a catalyzing oxidative agent.

Both beta oxidation and glycolysis (via pyruvate) produce acetyl CoA for the TCA. When beta oxidation is active there is ample amount of acetyl CoA around. In these situations pyruvate accumulates into the cells and body (like seen in example 2.3). This is why we can state that an increase in pyruvate is an indication of increased beta oxidation. Of course we need also other proof for the case of beta oxidation, like an increase in blood triglycerides and free glycerol from lipase reaction.

Enhancement of PPP by the use of DGA is an indication of increased cytosolic acetyl CoA levels, but that can be due to both an increase in pyruvate or in beta oxidation. Additionally in example 1.2.1 we have seen a dose dependent decrease in NAD+/NADH levels indicating that on whole cell level the metabolic activity has increased, but in there also we can't make a distinction on the exact source of the increment, because all energy producing pathways (including also the TCA) convert $NAD^+$ into NADH.

Accumulated pyruvate is a fact and it can be also used in anaplerotic and anabolic reactions. Depending on the redox-state of the cell it can also convert to lactate using reduced NADH as a co-enzyme, and producing cytosolic $NAD^+$. This ability of pyruvate to produce cytosolic $NAD^+$ rapidly is an additional, important feature of the use of DGA in e.g. preventing of AGEs formation. In general lactate levels seem to decrease more than 30% by the use of DGA which is very clear proof on the efficacy.

The rate of glycolysis, beta oxidation and the TCA, which depends on the cell's need for ATP, is controlled by the inhibition and stimulation of several enzymes. This complex regulation coordinates the activities of the glycolytic pathway, beta oxidation and the citric acid cycle and can results in the storage of glucose as glycogen or as fat when ATP is abundant.

Lactate formed in the skeletal muscles can be exported to the liver and converted there back to pyruvate and further to gluconeogenesis in the liver and later moved back to the muscles as glucose (so called Cori cycle).

Mitochondria have a permeable outer membrane and an inner membrane, which is the site of electron transport system and ATP synthase. Pyruvate dehydrogenase, a very large multienzyme complex in the mitochondrial matrix converts pyruvate into acetyl CoA and $CO_2$. In each turn of the citric acid cycle, acetyl CoA condenses with the four-carbon molecule oxaloacetate to form the six-carbon citrate, which is converted back to oxaloacetate by a series of reactions that release two molecules of $CO_2$ and reduce three $NAD^+$ into NADH molecules and one FAD into FADH2 and further one ubiquinone into ubiquinol and one GDP into GTP molecule (FIG. 1). $CO_2$ is exhaled or converted to bicarbonate and excreted via urea cycle to urine.

The NADH generated in the cytosol during glycolysis can be re-oxidized to $NAD^+$ e.g. with the concomitant reduction of $NAD^+$ to NADH in the mitochondrial matrix, by a set of enzymes and transport proteins that form shuttle mechanisms through the inner mitochondrial membrane (IM), e.g. so called malate-aspartate-shuttle or glycerol phosphate shuttle (FIG. 1a).

In the matrix reduced NADHs from the TCA and from above mentioned shuttle mechanisms are mostly transported to the so called electron transport system (ETS) located in and on the IM (FIG. 1a).

In the ETS, electrons from NADH and $FADH_2$ move via a series of membrane-bound electron carriers in the inner mitochondrial membrane to $O_2$, regenerating $NAD^+$ and FAD. This stepwise movement of electrons is coupled to pumping of protons across the inner membrane. The resulting proton-motive force powers ATP synthesis by creating electric gradient over inner membrane of mitochondria and generates most of the ATP resulting from aerobic oxidation of glucose.

ETS consists of several complexes that transport electrons and bump protons from the matrix to the inter membrane space (IMS). The end product of ETS is water and formed electrochemical gradient can "energize" ADP molecules into ATP inside the matrix in ATP synthase complex spanning through the inner membrane. Pumping ATP out of the matrix and ADP into the matrix requires some energy thus consuming part of the electrochemical gradient (FIG. 1a). Most of the complexes in ETS span throughout the inner membrane but so called complex II type of shuttle mechanisms operate only from one side of inner membrane. "Standard" complex II shuttle is located inside the matrix and it forms also one step in the TCA, i.e. reaction from succinate to fumerate catalyzed by flavin adenosine dinucleotide (FAD). GP-shuttles are Complex II type of mechanism that are on the outside of the inner membrane.

Main Sites of Action

Most important main site of action in aerobic cells is the ATP producing electron transfer system (ETS) in mitochondria. Signals for activated aerobic metabolism channel from cytosol into nucleus and from there to mitochondria (FIG. 2). Thereafter or simultaneously are MA- and GP-shuttles that shuttle reducing equivalents into the cytosol activated. Next, the mitochondrial activation of ATP production enhances the interplay between mitochondria and endoplasmic reticulum and peroxisomes. Finally increased ATP and substrates (pyruvate and amino groups) activate inter alia protein and enzyme syntheses; additionally increased availability of ATP activates unfolded protein response and similar important cellular metabolic control mechanisms.

All in all it seems clearly that the whole ATP energy producing system of the cell is increased as well as Nrf2/ARE pathways (Example 1.1/decline in ROS and Example 1.2.1/increase in NADH concentrations). Rate of beta oxidation seems to be increased also structurally in the longer term administration (Example 5). Typically beta oxidation and glycolysis compete, but paradoxically also glycolysis may be enhanced due to increased amount of redox-balancing pyruvate and increased capacity of GP- and MA-shuttles.

Produced extra ATP must be consumed, because stored fat or glycogen amounts do not seem to pile up, in fact the contrary (see Example 4). More discussion on these observed effects is in the next section below.

ATP Production Per Gram of Nutrition and Change in Body Composition

ATP is continuously recycled in organisms. It has been estimated that the human body, which on average contains some 250 grams of ATP, roughly turns over its own body weight equivalent in ATP each day.

Even though we can say that aerobic and also anaerobic ATP production capacity and very likely also the ATP production is increased by the use of DGA, we can't estimate the precise effect of the use of DGA on the ATP production per gram of nutrition because there are so many endogenous processes that are affected and that feed back to the "equation" that changes also itself.

On one hand GP-shuttles on the outside of inner mitochondrial membrane, can yield increase in metabolic flux with stable ATP production compared to situation without increased activity of GP-shuttles, i.e. ATP production per gram of nutrition is decreased. But on the other hand increase in aerobic energy metabolism within the cells and clearly less lactate trafficking Example 2.3.3) back to the liver, yields very significantly more energy per gram of nutrition compared to glycolysis and lactate cycling/export to the liver. Additionally gene expression results (Example 2.3.2) and increased substrate providing to both shuttles point to that the normal balance between more efficient MA-shuttles and less efficient GP-shuttles is restored to normal very soon after first spark in GP activity. (Additional note: GP-shuttles are also limited by its substrate (G-3-P and DHAP) availability in the IMS, and also by their tissue specificity. GP-shuttles may importantly speed up cytosolic NADH oxidation significantly in some situations and in some tissues, but their effect on over all energy metabolism of the body in normal metabolic situations is relatively small.)

Increase in the PPP (G6PD gene) can, depending on the destiny of G6P molecule, either increase ATP production (destiny glycolysis) or decrease it (destiny nucleobase formation). Increase in mitochondrial beta oxidation of fatty acids by the use of DGA can either enhance or deteriorate ATP yield per nutrition depending on e.g. how the triglycerides and related fatty acids are formed. Fatty acid synthesis consumes NADPH and glyceroneogenesis ATP and NADH. In general beta oxidation is very efficient slow energy provider and thus in normal metabolic situations its activation increases ATP yield per gram of nutrition.

All in all it is very reasonable to assume that in vivo, ATP production potential per gram of nutrition is increased by some percentage points. Clear reduction in lactate cycling supports this view also.

In example 4 we have seen a surprising phenomenon in which nutrition intake increased statistically significantly in 3 week experiment with rats and simultaneously body weight of rats in DGA groups decreased (males) or remained stable (females) compared to the control group without DGA. The phenomenon comes even more surprising when we assume an increase in ATP per gram of nutrition. If there is no additional demand for ATP, it is not produced by the cells. In abundant ATP situations the body starts to convert nutrition into glycogen and fat (typically as triglycerides) that should increase (not decrease) the weight of the rats.

Excess ATP can also be consumed to increased protein synthesis, and to sharpened control of various metabolic processes (e.g. unfolded protein response). As presented FIG. 2 and shown by human (and animal) in vitro and in vivo examples the use of DGA clearly increases the "discussion" between nucleus and mitochondria in energy metabolic and antioxidant/anti-inflammatory pathways. The use of DGA also increases mitochondrial metabolism and also biogenesis of new mitochondria (and naturally the autophagy of the old ones). Mitochondria on the other hand have a close interplay between the ER where proteins (rough ER) and lipids (smooth ER) are synthesized. Also peroxisomes are activated by the use of DGA (see FIG. 1b). All in all we find it very reasonable to believe that the extra (unexplained) ATP is consumed to many anabolic reactions that e.g. in net terms convert fat to protein (muscles) and triglycerides stores in myocytes (muscles), i.e. fat into muscle mass, and to increased metabolic control leading to clearly healthier over all metabolism in the long run.

Rough calculation on muscle mass increase. Based on Examples 2.1-2.3 (declines in urea cycle and NO output in healthy volunteers) we can assume that the rate of urea output from the body decreases in short (max. 1-4 week) administration of DGA by some 10%. Average men remove roughly 15 grams of urea from the body in the urine per one day. In 15 g of urea there is roughly 7 g of nitrogen (N). In the literature it is mentioned that a gram of N is roughly equal of 6.25 g of protein, and 1 g of protein equals roughly 5 g of muscle mass. All in all a 10 percent save of N due to decline in urea output can be estimated to equal some 219 grams of saved (skeletal) muscle mass per day. In adult men skeletal muscles make up some 42% of the bwt, i.e. some 30 kg in average 70 kg adult man. Thus in 2 weeks over 3 kg or more than 1% of the muscle mass can be saved. This figure can be very likely increased by optimization. In animals DGAcs should probably be used only some weeks or days before the slaughtering, because longer term addition on DGAcs into the animal feed can increase costs uneconomically.

As a non-limiting example, in some optimized conditions meat contents (mass or weight) could possibly increase some 1-2% and simultaneously fat contents to drop 2-3% measured of the total body weight with stable food consumption. Commercially this is viable because the production process by fermentation gives as the side output big amounts of material that contains small amounts of DGA and that can be used as food after validation of the production process. Use of the side output increases also the environmental sustainability of the production. Additionally there are potentially even significant possibilities to further enhance the conversion from fat to protein by the use of DGA by optimization for different life stock, feed, feeding time and DGAcs concentration etc. An example being activated interplay between DGA-HPA-loop (genes DGDH and GRHR) and PPP (G6PD) that can in certain settings clearly increase further the ATP yield per gram of nutrition. The Effective Dose and Suitable Time of the Administration The present inventors have observed in vitro cell culture experiments and in vivo experiments that administration of DGA, and in vitro experiment with LGA and HPA (FIG. 11) that in small doses substances of the innovation are able to enhance direct and/or indirect mitochondrial metabolism and simultaneously to reduce oxidative stress. Doses both in vivo and in vitro experiments have been adjusted as equal as possible. In here it should be noted that in vitro studies there is full and direct effect of the substance towards chosen tissues and cells e.g. hepatocytes. In oral administration i.e. in vivo studies used substance first enters mouth and gastrointestinal tract and only thereafter to the blood stream etc. Thus most effective "equal" amounts can be several times higher in oral administration compared to cell cultures.

In in vivo studies the doses range from 3 to 12 mg/kg/day, and in in vitro studies the doses range from 0.2 to 20 mg/kg/day. Positive effects from the administration are observed with all tested doses (except for tested very low doses in vitro, 0.02 mg/kg/day, in some studies). An effective dose depends greatly on the activity of subject's mitochondria. In general the better the physical condition of the user the smaller doses per kilogram per day are effective. The excess storage of fats and glycogen in the cells may increase the need of the dose per kilogram per day. Based on the results it can be concluded that there is clearly a safe possibility to take bigger doses D-glyceric acid temporarily, if needed. At the same time it is likely that the incremental positive effects disappear when dose get clearly bigger than normal effective dose.

Figure 11:
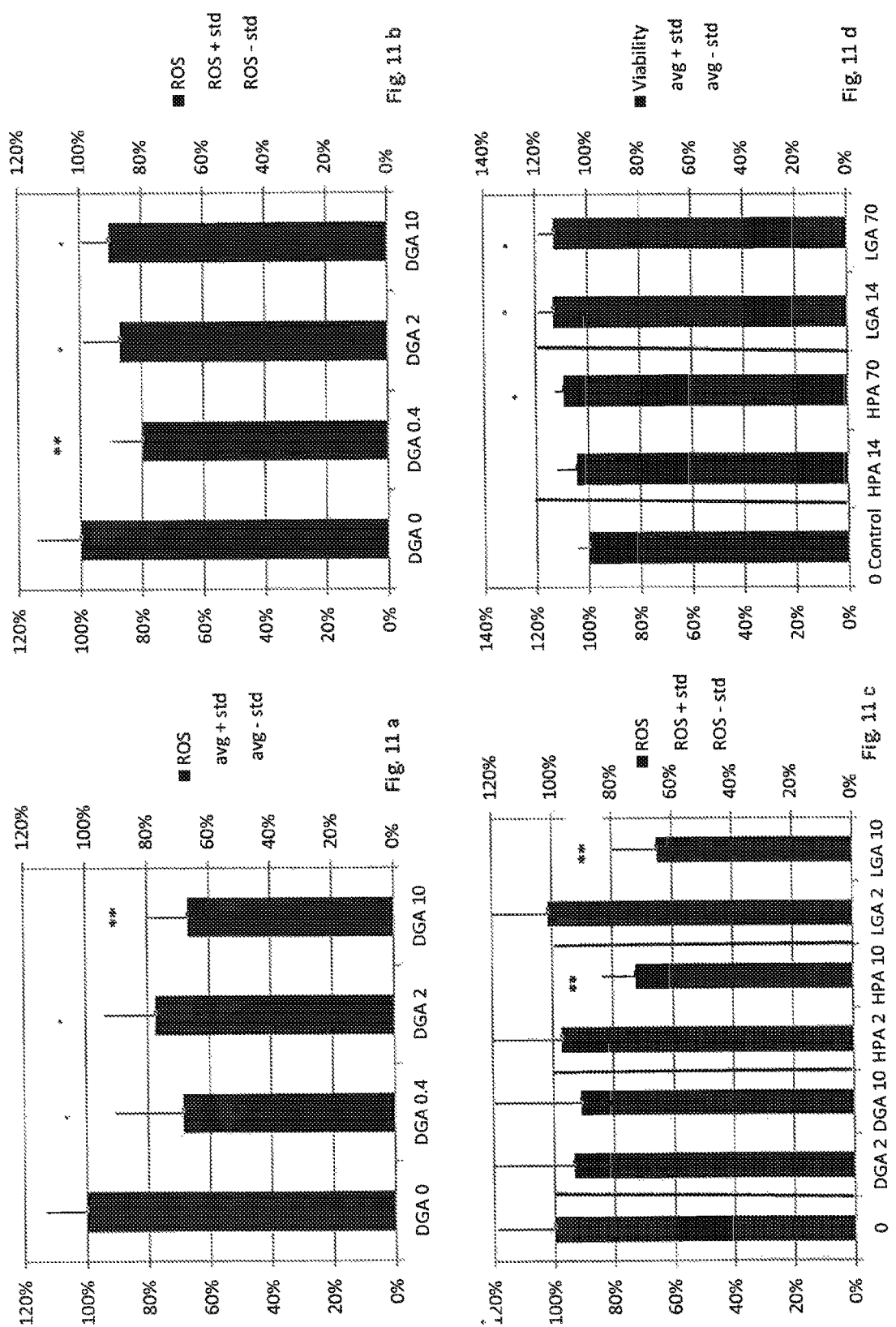
FIGS. 11a, 11b, 11c and 11d depict that DGA decreases ROS compared to 0 dose in study 2 (two upper graphs). In study 3 (lower left hand graph) also HPA and LGA decrease ROS compared to 0 dose. Further in study 3 (lower right hand graph) HPA and LGA increase viability compared to 0 dose. Results are measured under moderate metabolic stress. Experimental setup for study 2 and 3 is described in Example 1.

L-glyceric acid (LGA) is not a naturally active enantiomer of glyceric acid but it can in some circumstances be oxidized into HPA in humans and thus further into DGA. Thus also LGA molecules or its salts and esters can possess (indirectly) similar positive effects on cell metabolism than DGA and thus also LGA can be important part of this innovation (FIG. 11, lower graphs).

Figure 10:
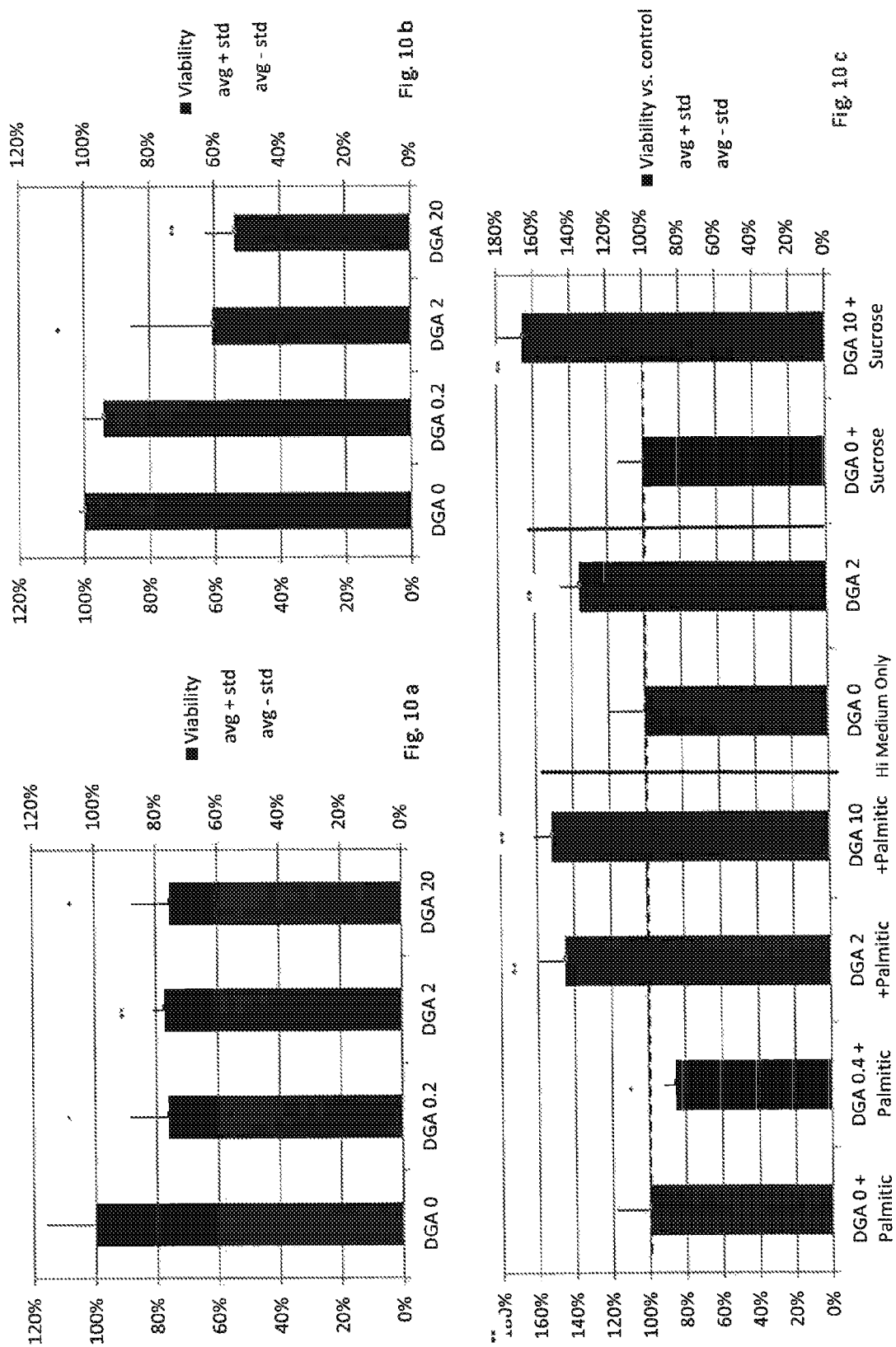
FIGS. 10a, 10b and 10c depict in study 1 starving diet test, i.e. no addition or change of medium during 48 hours, that DGA decreases the viability of hepatocytes compared to control (two upper graphs). Increase of viability shown in FIG. 9 with optimal nutrition and decrease of the viability of same donors in starving diets indicate clearly that DGA increases metabolic flux. In study 2 (male donor CDP/lower graph with 3 diets)) and normal change of medium, i.e. normal/optimal nutritional conditions, DGA again increases the viability of hepatocytes in almost all diets compared to 0 dose. It should be noted also that viability decreases with 0.4 DGA dose and Hi Medium+palmitic acid and this decline is statistically significant. Excessive increases of viability (or decreases) are not normal and they also indicate some kind of excessive increase of metabolism in the cells. In vitro cells/tissues can't control the stimulating effect of DGA, unlike in vivo (FIG. 5 and Table 3). Experimental set up for study 2 is described in Example 1.

In vitro experiments with primary human hepatocytes show effects in the amount of ROS, viability and metabolic flux (covering both anabolic and catabolic reactions). The amount of ROSs in metabolic stress situation is decreased by 15-40% and the viability of cells is increased on average by 5-10%. In some cases the hepatocytes viability in vitro has increased even by 40-60% (FIG. 10/lower graph). This is a clear indication that DGA has significant impact on the activity of the hepatocytes. That especially metabolic flux, i.e. anabolic and catabolic reactions, is increased is supported by the fact that hepatocytes kept under starvation (no addition of food, i.e. change of medium during 48+1.5-2 h) died clearly more likely than same hepatocytes without activating doses of DGA (first two graphs in FIG. 10).

Several in vivo effects are observed with healthy volunteers after standard 10-12 h fasting diet, such as clear increase in plasma pyruvate and clear decrease in lactate levels. Also NO levels were lowered statistically significantly in healthy volunteers, and increased with one subject experiencing mild to moderate metabolic syndrome (BMI >>25).

Also some enhancement in the intake of glucose, sodium and other nutritional substances from blood to cells is seen. Increased glucose intake was later confirmed in acute 4.5 day administering in vivo (Example 2.3.4). Significant lowering of bilirubin and bilirubin conjugate in blood is an indication of lower oxidative stress. Importantly in similar test with acute 4.5 day administering of DGA only 2.5 hours before the blood sample was taken, also very different results on bilirubin and HO-1 gene expression were received. With the suitable use of the DGA it is possible to manage average HO-1 expression up and down in circadian cycle. Decreased levels of uric acid (UA) in blood indicate that the systemic oxidative stress of cardiovascular system is reduced (see table 3).

The present invention is based on natural enhancement of indirect and direct mitochondrial metabolism and mitochondrial energy production. The amount of reactive oxygen species (ROS) is decreased due to activated Nrf2/ARE systems. The redox state is improved. Also metabolic syndrome in general is ameliorated due to increased metabolic flux with less ROS. The positive effect from the use of DGA is obtained during fed and fasting. Fasting situation before going to bed is likely the most effective time to promote longer term health effects.

DGA gives cells a signal for increased mitochondrial aerobic metabolism. Simultaneous increase in the activity of mitochondrial $NAD^+$ transporting shuttles due to increase in substrates extensifies the positive effect on energy metabolism. Very likely DGA-HPA-loop presented in FIG. 1b lengthens the effect of very small administering to last e.g. 24 h before a new very small dose is taken. In the longer run also structural positive changes towards aerobic metabolism and enhanced capacity for keeping optimal cytosolic $NAD^+$/NADH-ratio will appear, as well as enhanced Nrf2/ARE pathways.

For some individuals, with less active mitochondria, 4 week or even longer administration period might be needed for obtaining significant results like on table 3 for lean persons with good physical condition in 4 days. For overweight people or persons with very low physical condition the most beneficial combination is to start suitable physical training at the same with DGA administration. This way the health effects of DGA arising mostly from mitochondrial activity materialize more rapidly. Additionally daily doses for overweight people or persons with very low physical condition during the first week or two should be high (7-10 mg/kg twice a day) compared to longer term administration of 5 mg/kg once a day before going to bed.

The endogenous antioxidant defense is increased in the body. The composition of the present invention is useful as e.g. a complement to vitamins.

The decrease in ROS and, if needed, the activation of HO-1 gene expression in cardiovascular system, and simultaneous reduction in blood pressure, and of blood lactate, sodium, and to some extend also blood cholesterol may be observed. This leads to improvements in patients suffering from a cardiovascular disease.

Also patients suffering from cancer and metabolic syndrome may benefit from the use of the compositions of the present invention. Another example of a preferable application is use in weight reduction, and in change of body composition from fat to muscle tissues.

A very useful application of the present invention is in aging process in fighting against neuro- and other degeneration in extremely wide range of diseases and disorders. This is supported by the human in vivo results and also by in vitro cell studies, wherein genes for increased energy metabolism and increased antioxidant defenses and anti-inflammatory response were activated, pyruvate amount was increased and lactate amount decreased. Also the reduction on the amount of ROS in human primary hepatocytes and increase in viability and in some cases increase of apoptosis of cells were observed supports the idea that the use of DGA can alleviate, postpone and even heal wide range of aging related diseases and/or disorders.

Therapeutic and/or Preventive Pathway(s) Induced by the Use of DGA

Enhanced mitochondrial energy metabolism is important for specific and also pleiotropic effects of the use of DGA or HPA in preventing non-communicable diseases. Simultaneous daily activation of Nrf2/ARE pathway and clear increase in blood pyruvate concentration makes the therapeutic potential of the use of DGA really significant for extremely wide range of diseases. More than 30% decrease in blood lactate confirms the increase in oxidative capacity by the use of DGA. Increase in ATP production enhances endogenous cell cycle control and also unfolded protein response as well as control of many other metabolic pathways. Extremely important in the use of DGA is its ability to up and also down regulate e.g. HO-1 (Nrf2/ARE) expression during circadian cycle that is clearly seen in conducted two clinical trials (Examples 2.1 and 2.3) with different time of measurements in respect to last DGAcs dosing. The use of DGA also promotes homeostasis of protease/antiprotease balance by activating Nrf2/PERK/MAPK (see FIG. 2).

Cardiovascular Disease

General therapeutic effects for reducing the risk for cardiovascular diseases: 1) Reducing Oxidative Stress and Inflammation when needed (daily activation of Nrf2/ARE genes). 2) Increasing mitochondrial biogenesis and energy production of peripheral leukocytes (PGC-1a and NRF1/MT-CO1. also Nrf2). 3) Increasing mitochondrial biogenesis and energy production of Cardiac Myocytes (PGC-1a and NRF1/MT-CO1, also Nrf2). 4) Enhancement of liver and kidney function (Nrf2/ARE, decreased blood urea, decreased blood lactate, improved AST/ALT-, HDL/LDL- and other ratios in blood). 5) Enhancement of lung function against oxidative stress, activation of Nrf2/ARE. 6) Increasing the viability of erythrocytes, their redox and energy state leading e.g. to increase in 2,3-BPG content (Nrf2/ARE and DGA-HPA-loop in FIGS. 2 and 1b and 3a). 7) Increasing endothelial Nitric Oxide production in subjects in need (Example 2.3.3).

Atherosclerosis

Atherosclerosis is caused by a combination slowly advancing and long lasting events that eventually lead to hardening and narrowing of the arteries due to plaque formation. These causes reduce the elasticity of the artery walls but do not affect blood flow for decades because the artery muscular wall enlarges at the locations of plaque. Initial cause may be some tiny defect on artery wall that leads to attack by white blood cells to correct the problem. Somehow inflammation is not properly corrected due to e.g. oxidative stress and/or improper fine tuning of the defense response by the body. Deficiency of nitric oxide (NO) and its endothelial synthase (eNOS) enzyme can further escalate the risk of serious consequences like e.g. elevated blood pressure and eventually myocardial infarct (MI). Also excessive amount of LDL compared to HDL cholesterol, and triglycerides in the blood stream may increase the risk of developing atherosclerosis, but there are experts who say that blood cholesterol and triglycerides can have even contrary effect towards cardiovascular diseases.

It is commonly agreed that oxidative stress and chronic inflammation in cardiovascular system are behind slow advance of Atherosclerosis. Also lack of physical exercise is often one major reason of the advancing of this disease. Furthermore consensus exists that nitric oxide (NO) and its endothelial synthase (eNOS) enzyme in endothelial cells and also in RBCs that is a recent discovery can alleviate Atherosclerosis and even prevent its serious consequences by making artery wall more flexible.

Therapeutic strategy of the use of DGA is to enhance the control of oxidative stress and reduce it when needed in cardiovascular system by daily activation of HO-1 and other Nrf2/ARE related antioxidant enzymes. Secondly the use of DGA aims at elevated efficiency in control of the inflammation response by the peripheral leukocytes. This task is achieved by increasing also energy production by increasing mitochondrial aerobic metabolism. Thirdly blood cholesterol balance is kept at suitable range by LDL receptor (LDLR) activation by HO-1 expression. Therapeutic effect of the use of DGA is clearly seen in Examples 2.3 and 1.1.2 showing clear increase in PGC-1a/NRF1 related genes, and also in Nrf2/ARE pathway genes (HO-1, G6PD and AOX1).

Prevention of Atherosclerosis follows also from the above described general therapeutic or preventive pathways. Additionally PGC-1alpha is a key regulator of high glucose-induced proliferation and migration in vascular smooth muscle cells (VSMCs), and suggests that elevation of PGC- 1alpha in VSMC could be a useful strategy in preventing the development of diabetic atherosclerosis.

Positive therapeutic effects from increased physical exercises have been shown to decrease the risk of Atherosclerosis. The use of DGA provides strongly similar effects than physical exercise, and thus can prevent Atherosclerosis, especially combined with some exercise and normal healthy diet.

Myocardial Infarction (MI)

MI prevention by the use of DGA follows from prevention of Atherosclerosis and the above described general therapeutic or preventive pathways for cardiovascular diseases. As seen in Example 2.1 and 2.3 blood levels of Creatine kinase (CK) are down, which is a sign of reduced muscle and myocardial dysfunction. Clinical in vivo down regulation of Ck in blood compared to controls also indicates an increased aerobic ATP production in line with main idea of the use of DGA. Positive therapeutic effects from increased physical exercises have been shown to decrease the risk of myocardial infarction. The use of DGA provides strongly similar effects than physical exercise, and thus can prevent Myocardial infarction, especially combined with some exercise and normal healthy diet.

Cardiomyopathy/Congestive Heart Failure

Prevention of cardiomyopathy and congestive heart failure follows from the above described general therapeutic or preventive pathways. Positive therapeutic effects from increased physical exercises have been shown to decrease the risk of cardiomyopathy/congestive heart failure. The use of DGA provides strongly similar effects than physical exercise, and thus can prevent cardiomyopathy/congestive heart failure, especially combined with some exercise and normal healthy diet.

Vascular Thrombosis and/or Embolism

Over expression of HO-1 has been shown to prevent vascular thrombosis and/or embolism. See also other relevant general stimulation effects by the use of DGA from above and below.

Asthma and Chronic Obstructive Pulmonary disease

Chronic Obstructive Pulmonary Disease (COPD) is a term used to describe a number of lung conditions that are long-term, gradually worsen, and cause shortness of breath by reducing the normal flow of air through the airways. The most common are emphysema, chronic bronchitis and chronic asthma. Each of these conditions can occur on its own, although many people have a combination of conditions. Asthma is a common chronic inflammatory disease of the airways characterized by variable and recurring symptoms.

Preventive and/or alleviating therapeutic strategy against COPD and Asthma arises from: 1) Enhanced control of oxidative stress in lungs and respiratory system by daily activation of HO-1 and other Nrf2/ARE related antioxidant enzymes. 2) Elevated efficiency in control of the inflammation response by respiratory tissues. This task is achieved by Nrf2/ARE activation and simultaneous enhancement of energy producing metabolism by increasing mitochondrial aerobic activity. 3) Increased substrate supply (pyruvate, serine and glycine, see FIG. 1b) for protein synthesis, and its enhanced quality and quality control (Nrf2/PERK/MAPK, see FIG. 2). 4) Increase in pyruvate (see pyruvate therapy above). 5) Increased regeneration of ascorbate (vitamin C) from dehydroascorbate (DHA), see FIG. 4.

Nrf2 activation can protect lungs from induced acute respiratory distress syndrome, hyperoxic injury, and in some pulmonary fibrosis by increasing detoxification pathways and antioxidant defense potential. The use of DGA can increase plasma pyruvate levels by 25% (shown in Example 2.3.3). An increase in plasma is a direct reflection of similar intracellular pyruvate increase through MCTs. Increase in pyruvate can alleviate, prevent or even heal many diseases and/or disorders such as lethal sepsis, lethal hemorrhagic shock, Leigh syndrome, COPD and other inflammatory diseases, mitochondrial DNA depletion and other mitochondrial diseases. The use of DGA can likely efficiently substitute so called pyruvate therapy.

G6PD and 6PGD (6-Phosphogluconate dehydrogenase) Deficiencies in RBC/Hemolytic Anemia and Infant Jaundice, Severe Nrf2/ARE deficiency has been reported to cause inter alia hemolytic anemia. The use of DGA can alleviate or prevent it activating Nrf2/ARE and enhancement of glycolysis in RBCs. Additionally the activation of Pentose Phosphate Pathway by the use of DGA may postpone or alleviate G6PD and 6PGD deficiency. Activating DGA-HPA loop in RBC can also compensate for G6PD and 6PGD deficiency.

Lethal Sepsis and Lethal Hemorrhagic Shock

The use of DGA can increase plasma pyruvate levels by 25% (shown in Example 2.3.3). An increase in plasma is a direct reflection of similar intracellular pyruvate increase through MCTs. Increase in pyruvate can alleviate, prevent or even heal many diseases and/or disorders such as lethal sepsis and lethal hemorrhagic shock.

Elevated Blood Pressure/Hypertension

Primary (essential) hypertension and/or secondary hypertension, including but not limited to incidental hypertension and hypoxic pulmonary hypertension. The use of DGA is an Nrf/ARE pathway/HO-1 agonist. Also increased diuresis and natriuresis by the use of DGA reduce hypertension. Other pleiotropic effects from other claims related to cardiovascular diseases and also enhanced function of major organs (see above and below) tend to lower elevated blood pressure. Decreased plasma lactate has been associated at least with reduction of incidental hypertension. Plasma Nitric Oxide seems to increase in subjects in need. The effect of the use of DGA on elevated blood pressure is seen from Example 2.1 and FIG. 12.

Hypoxic Pulmonary Hypertension

The alleviating strategy of the invention is based on the above and especially to the ability of the use of DGA as an efficient HO-1 regulator and an efficient agonist with bigger therapeutic doses. The use of DGAcs seems to enhance eNOS regulation and thus increase NO levels in subjects in need.

Disease or Disorder Related to Metabolic Syndrome (if not Mentioned Elsewhere)

Enhanced mitochondrial energy metabolism is important for specific and also pleiotropic effects of the use of the DGA also in other diseases related to metabolic syndrome than above mentioned cardiovascular diseases and hypertension. Simultaneous activation of Nrf2/ARE pathway and clear increase in blood pyruvate concentration and decrease in lactate makes its therapeutic potential really significant for extremely wide range of diseases related to metabolic syndrome.

Diabetes

Therapeutic effect in diabetes: PGC-1a and NRF1/MT-CO1 related enhancement of ATP production in cells. ATP enhances insulin sensitive GLUT4 cells to facilitate glucose influx (see Example 2.3.4). Glucose influx is further assisted by enhanced ATP/energy status of the cells due to conversion of extra glucose into glycogen with the help of phosphate group from UTP (note, ATP+UDP=ADP+UTP). Conversion of glucose into glycogen enhances passive diffusion of glucose from plasma. Insulin resistance (IR) is decreased. Significant plasma lactate decrease by the use of DGA points also clearly towards the ability to postpone or even heal type II diabetes. Activated AOX1 gene (also belonging to Nrf2/ARE pathway) has been shown to detoxify tissues. AOX1 is expressed also in human skin, the biggest organ of the body. The lack of AOX1 and ROS scavenging Nrf2/ARE enzymes have been shown to increase IR. Additional therapeutic effect of the use of DGA on IR is to activate AOX1 and other Nrf2/ARE enzymes. Pleiotropic effects (1, 3) of the invention towards all major organs from activation of Nrf2/ARE and PGC-1a/NRF1 pathways, and increase in energy fuel (pyruvate and decrease in lactate) in blood stream assist prevention of especially type II diabetes. Positive therapeutic effects from increased physical exercises have been shown to decrease the risk of type II Diabetes. The use of DGA provides strongly similar effects than physical exercise, and thus can prevent Diabetes, especially combined with some exercise and normal healthy diet.

Diabetic Neuropathy

Prevention by the use of DGA follows from effects described in section Diabetes (above) and from relevant effects described in section Neurodegenerative disorders (below).

Disorder Associated with Metabolism

Enhanced mitochondrial energy metabolism is important for specific and also pleiotropic effects of the use of the DGA, but simultaneous activation of Nrf2/ARE pathway, and clear decrease of blood lactate and an increase in blood pyruvate concentration makes its therapeutic potential really significant for extremely wide range of metabolic diseases, and probably unique in the mechanism of action. Extremely important in the use of DGA is its ability also to down regulate e.g. HO-1 (Nrf2/ARE) expression during circadian cycle like is clearly seen in two different clinical trials and in time dependence compared to dosing. Nrf2 serves as a master regulator of the ARE-driven cellular defense system against oxidative stress. Numerous studies have shown that Nrf2 protects many cell types and organ systems from a broad spectrum of toxic insults and disease pathogenesis. Multi-organ protection phenomenon of Nrf2/ARE arises from protection of many different cell types by coordinately up-regulating classic ARE-driven genes as well as cell type-specific target genes that are required for the defense system of each cell type in its unique environment. The widespread nature of Nrf2 may have an important therapeutic potential, allowing prevention of also carcinogenesis and neurodegenerative diseases.

Mitochondrial DNA Depletion Syndrome

The use of DGA can increase plasma pyruvate levels by 25% (shown in Example 2.3.3). An increase in plasma is a direct reflection of similar intracellular pyruvate increase through MCTs. It is generally known that an increase in plasma pyruvate can alleviate, prevent or even heal Leigh syndrome. The use of DGA can likely efficiently substitute so called pyruvate therapy (see above). Mitochondrial DNA depletion syndrome is likely efficiently alleviated by the direct activation of mitochondrial energy metabolism and ETS gene RNA expression. Also the activation of pentose phosphate cycle (G6PD gene expression) and protein synthesis both support the notion that the use of DGA is likely efficient against Mitochondrial DNA depletion syndrome. (in vivo gene expressions see Example 2.3.3 and increased protein/enzyme synthesis Examples 2.1-2.3)

Leigh Syndrome

The use of DGA can increase plasma pyruvate levels by 25% (shown in Example 2.3.3). An increase in plasma is a direct reflection of similar intracellular pyruvate increase through MCTs. Increase in pyruvate can alleviate, prevent or even heal many diseases and/or disorders such as Leigh syndrome. Leigh syndrome is related to dysfunction in CNS mitochondria and thus the use of DGA can likely alleviate, prevent or even heal it also directly by activating mitochondria in the neuronal system (Example 2.3.2 and Example 3.2).

Epilepsy

In literature Epilepsy is described as a group of long-term neurological disorders characterized by epileptic seizures. These seizures are episodes that can vary from brief and nearly undetectable to long periods of vigorous shaking. In epilepsy, seizures tend to recur, and have no immediate underlying cause while seizures that occur due to a specific cause are not deemed to represent epilepsy. Activation of Nrf2/ARE has been shown to alleviate Epilepsy. Also the protection by the use of DGA against excitotoxic insult could be beneficial for prevention of epileptic seizures. Furthermore inducers of CYP3A4 and CYP2B6 have been used as anticonvulsants and mood stabilizers. In Example 5.3.2 it is shown that the use of DGA can induce both of these genes. Preventive and alleviating therapeutic effects of the invention for occurrence of epileptic seizures follow from the above and additionally from general descriptions for age related neurodegenerative diseases (see below).

Bipolar Disorder

Inducers of CYP3A4 and CYP2B6 have been used as anticonvulsants and mood stabilizers in bipolar disorder. In Example 5.3.2 it is shown that the use of DGA can strongly induce both of these genes, and thus it can possibly be efficiently used in protection against bipolar disorder and possibly also in schizophrenia. For additional preventive and alleviating therapeutic effects of the invention for occurrence of bipolar disorder, see epilepsy (above) and general descriptions for age related neurodegenerative diseases (below).

Psychiatric Disorders and Mood Disorders

Psychosis, schizophrenia, autism, depression, personality change, panic disorder, anxiety disorder. Major psychiatric diseases are common, chronic, recurrent mental disorders that affect the lives of millions of individuals worldwide. Although schizophrenia and mood disorders are not classic neurodegenerative disorders, there is an increasing amount of evidence that these disorders are associated with abnormalities in cellular plasticity, including the ability of neuronal and glial cells to resist or adapt to environmental stressors and the ability of these cells to undergo remodeling of synaptic connections. Neuronal function is highly dependent on mitochondrial function. Thus impaired mitochondrial function might lead to a disruption of normal neural plasticity and reduce cellular resilience, promote the development or progression of mood and psychotic disorders. The use of DGA can alleviate or prevent psychiatric and mood disorders by activating its three main pathways Nrf2/ARE, PGC-1a/NRF1 and pyruvate formation presented in FIG. 2.

Cerebrovascular Accident, Damage from Acute Head Injury

Prevention of Cerebrovascular accident (CVA, or alternatively stroke or ischemia) follows from the above described general therapeutic or preventive pathways. Also enhanced recovery and damage suppression follows from the above described general therapeutic or preventive pathways. The protection of neurons against excitotoxic insult by the use of DGA, see example 3.1, is beneficial for prevention of permanent injuries from CVA and other damage from acute head injury or trauma.

Acute or Chronic Renal Failure

Nrf2/ARE has been shown to increase diuresis and natriuresis (also seen in clinical tests, Example 2.1-2.3) that indicates improvement in renal function. Activated AOX1 gene has been shown to detoxify various tissues. Therapeutic effects of the use of DGA on renal function arise also from reduced/shared burden on kidneys to detoxify body fluids. E.g. blood urea levels have been shown to decrease after the use of the use of DGA. The use of DGA facilitates also the prevention of diabetic nephropathy in chronic kidney disease. Kidneys have also a role in gluconeogenesis, secondary to the liver. Significantly decreased lactate levels and increased amount of pyruvate in blood stream by the use of DGA is a clear indication that the pressure towards gluconeogenesis in the liver and in kidneys for brains and other tissues decreases. It liberates renal resources for other important metabolic functions, especially in subjects in need. By rendering free capacity to kidney's, and the activation of Nrf2/ARE and aerobic energy metabolism the use of DGA suppresses and corrects various renal malfunctions. Thus it may possibly also reduce e.g. kidney stone formation due to activation of metabolic control.

Acute or Chronic Liver Failure

Liver is probably the most important inner organ in metabolism. On top of various vital tasks related to nutrition intake and excretion, and metabolite detoxifying, it has a major role in gluconeogenesis and triglyceride synthesis, and numerous other tasks that effect wellbeing of other major organs and whole physiological system(s). Significantly decreased lactate levels and increased amount of pyruvate in blood stream by the use of DGA is a clear indication that the pressure towards gluconeogenesis in the liver decreases. It liberates hepatic resources for other important metabolic functions, especially in subjects in need.

In Examples 1.1-1.2 and 2.1-2.3 we show clearly that the use of DGA activates very effectively endogenous ROS scavenging mechanisms in human primary hepatocytes. In separate gene expression studies with hepatocytes (in vitro) and peripheral leukocytes (in vivo) we have been able to show that ROS scavenging is due to increased expression of Nrf2/ARE related genes e.g. HO-1, G6PD and AOX1. Also the master regulator PGC-1a/NRF1 gene was activated in human primary hepatocytes.

Test set up with hepatocytes (in vitro) in Starving Diet and the comparison with standard diet indicates clearly that hepatic activity increases by the invention and it leads to cell death due to lack of nutrition, i.e. starvation in 48 h test. Significantly increased levels of circulating triglycerides in some of the clinically tested individuals (Examples 2.1-2.3) indicate also enhanced hepatic triglycerides formation activity by the use of DGA in vivo. (The increase in triglycerides is of course also an indication of increased demand of fatty acids for beta oxidation, resulting further in increase in hepatic and plasma free glycerol levels (see Example 5).

Splenomegaly

Nrf2/ARE deficiency has been reported to cause Splenomegaly and often related hemolytic anemia. The use of DGA can alleviate or prevent Splenomegaly by activating its three main pathways Nrf2/ARE, PGC-1a/NRF1 and pyruvate formation presented in FIG. 2.

Increased viability of RBCs (see e.g. table 4/LDH result and FIG. 3. d) can reduce the risk of Splenomegaly.

Acute or Chronic Pancreatic Failure

Increase in PGC-1a/NRF1 pathway and subsequent enhancement in energy metabolism alleviates symptoms. Interestingly it has been shown that GP-shuttles are especially active in pancreatic beta cells that produce insulin. GP-shuttles and increase in aerobic metabolism produce ROS. On the other hand Nrf2/ARE-mediated antioxidant induction has been shown to play paradoxical roles in pancreatic beta-cell function: 1) induction of antioxidant enzymes protects beta-cells from oxidative damage and possible cell death, thus minimizing oxidative damage related impairment of insulin secretion, and 2) the induction of antioxidant enzymes by Nrf2 activation blunts glucose-triggered ROS signaling, thus resulting in reduced glucose stimulated insulin secretion.

In our limited clinical tests blood insulin levels have tended to increase more rapidly with the use of the invention, thus indicating activated pancreatic function.

Chronic Auto Inflammation and Autoimmune Syndrome and Diseases

Initial cause of the onset of chronic auto inflammation and autoimmune diseases may be some tiny defect somewhere in the body that leads to attack by the immune defense system to correct the problem. Somehow inflammation is not properly corrected due to e.g. oxidative stress and/or improper fine tuning of the defense response by the body. Also some long term irritation from external toxins can cause the onset of the syndrome.

In literature Auto inflammatory diseases are described as a relatively new category of diseases that are different from autoimmune diseases. However, autoimmune and auto inflammatory diseases share common characteristics in that both groups of disorders result from the immune system attacking the body's own tissues, and also result in increased inflammation.

Therapeutic strategy of the use of DGA is to enhance the oxidative stress and the anti-inflammation control of tissues and also the immune system by daily ensuring and testing of the activity of Nrf2/ARE pathway enzymes. Secondly the use of DGA aims at elevated efficiency in control of the inflammation response by increasing aerobic energy production of peripheral leukocytes and immune systems as a whole. This task is achieved by increasing mitochondrial aerobic metabolism, i.e. PGC-1a/NRF1 related genes. Therapeutic effect of the use of DGA is clearly seen in examples 2.3.3 (and 1.2) showing clear increase in PGC-1a/NRF1 related genes, and also in Nrf2/ARE pathway genes (HO-1, G6PD and AOX1). The use of DGA increases also detoxifying capacity by increasing AOX1 gene expression.

Furthermore, the use of DGA can decrease NO levels in the body demonstrated in example 2.3.3. In literature it has been reported that iNOS induced NO (see description of FIG. 4) often exacerbates inflammation, thus the reductions can be beneficial. The statistically significant 13% decline in NO in healthy individuals is likely due to inhibition of NF-kB (FIG. 2) that can explain the reduced iNOS activity and subsequent reduction in NO by the use of DGA.

Finally the use of DGA can increase plasma pyruvate levels by 25% (shown in example 2.3.3). An increase in plasma is a direct reflection of similar intracellular pyruvate increase through MCTs. Increase in pyruvate can alleviate, prevent or even heal many inflammatory diseases. Non-limited examples of chronic auto inflammation diseases: 1) Gout is a medical condition usually characterized by recurrent attacks of acute inflammatory arthritis—a red, tender, hot, swollen joint. 2) Rheumatoid arthritis is an autoimmune disease that results in a chronic, systemic inflammatory disorder that may affect many tissues and organs, but principally attacks flexible (synovial) joints.

Reduction in uric acid may alleviate gout as well as increase in aerobic energy metabolism. Also the ability of DGA to manage HO-1/Nrf2 enzymes up and down paves way for efficient therapy regimen towards arthritis gout and also rheumatoid arthritis. See also other general therapeutic effects of the use of DGA (in above and below) for alleviating and prevention of Chronic auto inflammation and autoimmune syndrome and diseases.

In this use the DGA can be classified as NSAID, i.e. non-steroidal anti-inflammatory drug.

Psoriasis

Psoriasis is an inflammatory skin disease with characteristic changes in the epidermis that resembles unsuppressed wound healing due to excessive hyperproliferation of keratinocytes. The exact cause of Psoriasis Vulgaris and Psoriasis Arthritis is not known but dysfunction in cell regulation due to ROS and toxins, and possibly due to dysfunction in energy metabolism are important reasons for onset and incidence of psoriasis. In recent years there has arisen growing evidence that psoriasis more frequent in patients with other disorders related e.g. to metabolic syndrome.

Therapeutic effect 1 a: Increase in the activity of HO-1/Nrf2/ARE related enzyme pathway against epithelial ROS damage.

Therapeutic effect 1 b: In literature it has been shown that increased HO-1 expression is essential for wound healing indicating clearly that the use of DGA has the potential to manage occurrence of Psoriasis due to the fact that it can efficiently and dose dependently manage HO-1 expression in cells, example 2.1, 2.3.1 and 2.3.2.

Therapeutic effect 2: Increase in the activity of AOX1/Nrf2/ARE related enzyme pathway against various toxins towards epithelial cells.

Therapeutic effect 3: More accurate control and suppression of over expression of auto inflammatory pathways and cell proliferation due to enhanced energy production (pyruvate therapy) and status of epithelial keratinocytes.

Therapeutic effect 4: the use of DGA can decrease NO levels in the body demonstrated in example 2.3.3. It is well known that iNOS induced NO (see description of FIG. 4) often exacerbates inflammation and clearly observed also in Psoriasis, thus observed reductions in NO can be beneficial.

Therapeutic effect 5: Pleiotropic effect from management of general disorders related e.g. to Metabolic Syndrome can likely postpone the onset or reduce the occurrence of Psoriasis.

Impairment in Collagen Synthesis

Collagen is the most abundant protein in mammals. Its synthesis is typically reduced as an organism ages. From the literature any defect in collagen synthesis is described to lead to disorders like impaired osteogenesis, scurvy, systemic lupus erythematosus as well as some other auto immune diseases. Reduced synthesis of collagen types I and III is also characteristic of chronologically aged skin.

Many cell types e.g. osteoblasts produce collagen. Glycine is clearly the most abundant amino acid in collagen. It forms approximately one third of its content. Reduced form of ascorbate is a rate limiting step in collagen synthesis.

The invention can 1) enhance stem cell differentiation into osteoblasts by increased HO-1 expression (Example 2.3.2), 2) very likely increase peroxisomal glycine and pyruvate output from imported alanine and glyoxylate via HPA-Serine-loop (see FIG. 1b, and FIG. 3) can efficiently enhance ascorbate regeneration from dehydroascorbate (ROS/Example 1.1 and increased NADPH producing capacity, FIG. 4).

Thus the use of DGA can attenuate, postpone, and even cure many age related diseases arising from impaired collagen synthesis.

Pre-Eclampsia

Pre-eclampsia is a disorder of pregnancy characterized by high blood pressure and large amounts of protein in the urine. Though present in the majority of cases, protein in the urine need not be present to make the diagnosis of preeclampsia. It involves many body systems and evidence of associated organ dysfunction may be used to make the diagnosis when hypertension is present.

From the literature, serum concentration of oxidized low-density lipoprotein (oxLDL) is higher in women with preeclampsia than in normal pregnant woman. LDL receptor (LDLR) is the scavenger receptor for oxLDL and it is abundantly expressed in placenta. It is well known that oxLDL activates nuclear factor erythroid 2-related factor 2 (Nrf2), a master regulator of antioxidant and cytoprotective genes such as heme oxygenase-1 (HO-1), which play an important role in pre-eclampsia. HO-1 activation has been shown to alleviate pre-eclampsia.

With correct dose, the use of DGA can significantly increase HO-1 expression in peripheral leukocytes and other tissues. Additional important therapeutic effect from the use of DGA comes from its alleviating effects towards other organ dysfunction related to pre-eclampsia.

Thyroid Disease

In literature Thyroid disease is described as a medical condition impairing the function of the thyroid gland. Imbalance in production of thyroid hormones arises from dysfunction of the thyroid gland itself, or the pituitary gland, which produces thyroid-stimulating hormone (TSH), or the hypothalamus, which regulates the pituitary gland via thyrotropin-releasing hormone (TRH). Concentrations of TSH increase with age, requiring age-corrected tests. Hypothyroidism affects between three and ten percent of adults, with incidence higher in women and the elderly.

The use of DGA can alleviate and postpone the onset of dysfunction of thyroid gland. Therapeutic strategy of the use of DGA is to enhance the oxidative stress and the anti-inflammation control of tissues and also the immune system by daily activation of Nrf2/ARE pathway enzymes. Secondly the use of DGA aims at elevated efficiency in control of the inflammation response by increasing aerobic energy production of peripheral leukocytes and immune systems as a whole. This task is achieved by increasing mitochondrial aerobic metabolism, i.e. PGC-1a/NRF1 related genes. Therapeutic effect of the use of DGA is clearly seen in gene expression and other examples showing clear increase in PGC-1a/NRF1 related genes, and also in Nrf2/ARE pathway genes (HO-1, G6PD and AOX1). The use of DGA increases also detoxifying capacity by increasing AOX1 gene expression.

Chronic Fatigue

Main therapeutic effect: increase in energy metabolism and production of ATP (PGC-1a/NRF1 pathway).

Positive therapeutic effects from increased physical exercises have been shown to decrease the symptoms of chronic fatigue. The use of DGAcs provides strongly similar effects than physical exercise, and thus can alleviate and even prevent chronic fatigue, especially combined with some exercise and normal healthy diet.

Fibromyalgia

Main therapeutic effect: increase in energy metabolism and production of ATP (PGC-1a/NRF1 pathway).

Also increased Nrf2/ARE-mediated antioxidant defense and anti-inflammation control alleviate fibromyalgia.

Positive therapeutic effects from increased physical exercises have been shown to decrease the symptoms of chronic fatigue. The use of DGAcs (Invention) provides strongly similar effects than physical exercise, and thus can alleviate and even prevent chronic fatigue, especially combined with some exercise and normal healthy diet.

Overweight

The use of DGAcs increases anabolic and anaplerotic reactions that per se promote healthier metabolism and on the other hand consume a lot of energy. Used energy is consumed in the form of ATP (e.g. in pyruvate carboxylase, protein synthesis), GTP (e.g. in gluconeogenesis), UTP (e.g. glycogen production), and CTP (for phospholipid synthesis). Importantly ATP can render its phosphate group to GDP, UDP and CDP using enzyme nucleoside-diphosphate kinases and activate them back to their most active/highest energy state. Thus enhanced ATP production of the use of DGA can efficiently contribute to these anabolic and anaplerotic reactions. Increased use of energy/nutrition leading to weight loss by the invention has been shown indirectly in controlled starving diet test with human primary hepatocytes and calorie restriction test with rat cortical neurons, see. Examples 1.1 and 3.1, and also directly in 3 weeks rat feeding study, see Example 4. The use of DGA works best to reduce overweight when also aerobic muscle cells (myocytes) are activated by exercise, i.e. when the main pathways related to the use of DGA are in use.

Cancer

Increase in antioxidant protection of basically all cell types from activation of Nrf2/ARE, i.e. decreased DNA damage from ROS and thus decline in occurrence of cancer cells. Enhanced energy metabolism and mitochondrial activity leads to more accurate control of malignant cancer cells and their controlled apoptosis. Also enhanced pyruvate supply to aerobic cells facilitates cells' endogenous quality control. Nrf2/ARE/HO-1 as an inhibitor of NF-kB nuclear translocation, can increase apoptosis in certain cancers, e.g. solid tumor and hematological malignancies. On the other hand NF-kB activation can also have positive effect for suppressing some tumors. Enhanced aerobic energy production of potential tumor cells by the use of DGA facilitates critical screening process for controlled apoptosis.

Cancer Subtypes

Basically all types of cancers that are caused by ROS damage to the cell, dysfunctioning mitochondria (e.g. compromised ability for apoptosis) or/and dysfunction of the energy production of the cells can be postponed or even prevented by the invention. In some cases the use of DGA could even facilitate a process that endogenously could suppress some tumor. In general by alleviating aging related degeneration of the cells, the use of DGA can reduce the number of malignant cells and/or enhance their controlled cell death.

List of cancer subtypes that the use of DGA can supposedly postpone, alleviate, prevent or even suppress can be found e.g. in National Cancer Institute of US NIH: http://www.cancer.gov/cancertopics/types/alphalist Disease or Disorder Related to Aging of an Organism, i.e. Degeneration of the Organism, its Organs, and Cell Tissues Like Neuronal, Epithelial, Endothelial, and Other Metabolically Active Tissues General Therapeutic or Preventive Effects and Pathways of the Invention for Diseases and Disorders Related to Aging Enhanced mitochondrial energy metabolism (PGC-1a/NRF1) is important for specific and also pleiotropic effects of the use of DGA in preventing degeneration due to aging. Simultaneous activation of Nrf2/ARE pathways genes is also crucial. Additionally simultaneous clear increase in blood pyruvate concentration makes therapeutic potential of the use of DGA really significant for extremely wide range of ageing related diseases and probably unique in the combined action of multiple mechanisms. Related increase on mitochondrial biogenesis in neurons, leukocytes, and other aerobically active cell types intensifies the defensive mechanisms against degeneration due to aging of an organism. Extremely important in the use of DGA is its ability also to down regulate e.g. HO-1 (Nrf2/ARE) expression during circadian cycle. This is clearly seen in conducted two clinical trials, with different time of measurements compared to dosing of the use of DGA, Examples 2.1 and 2.3.3. Decrease in diabetic neuropathy can prevent slowly advancing chronic neurological diseases. (See above)

Age Related Hearing Loss

Age related hearing loss includes but is not limited to presbyacusis, Nnise induced hearing impairment and ototoxic hearing impairment. Age-related hearing loss (AHL) is associated with an age-dependent loss of sensory hair cells, spiral ganglion neurons, and stria vascularis cells in the inner ear. AHL is thought to be the result of aging, oxidative damage, mitochondrial impairment, and environmental factors. Noise is the most documented environmental factor causing hearing loss. Outer hair cells are the primary lesion from noise exposure, and the accumulated effect of noise is thought to contribute to AHL. Ototoxic substances such as aminoglycoside antibiotics also increase susceptibility to AHL as these drugs can damage hair cells.

Experimental evidence suggests that mitochondrial dysfunction associated with reactive oxygen species (ROS) plays a central role in the aging process of cochlear cells. Cochlear cells are exquisitely sensitive to disturbances in energy metabolism. There is a growing bod of evidence suggesting mitochondrial ROS contributes to AHL that is age-dependent and has no defining genetic basis.

Reactive oxygen species contribute to the formation of several types of cochlear injuries, including age-related hearing loss and medicine induced ototoxity. The present findings in literature clearly indicate that Nrf2/ARE pathway protects the inner ear against age related hearing injuries and ototoxicity by up-regulating antioxidant enzymes and detoxifying proteins.

Therapeutic effect 1: Longer term managed increase in the activity of HO-1/Nrf2/ARE related enzyme pathway against hair cell ROS damage.

Therapeutic effect 2: Increase in the activity of whole Nrf2/ARE pathway and related up-regulation of detoxifying enzymes in the inner ear.

Therapeutic effect 3: Increase in PGC-1a/NRF1 pathway and subsequent enhancement in energy metabolism could postpone or alleviates symptoms of age-related hearing loss. Enhanced neuronal metabolism (due also to increased pyruvate) can also facilitate signal transportation from hair cells to the brains.

Age Related Macula Degeneration

From the literature: Age related macular degeneration (AMD) is triggered by oxidative stress, which imbalances innate immunity. Retinal pigment epithelial (RPE) cell/mitochondrial damage are the key events in early disease that is regulated by the transcription factor Nrf2/ARE pathway. Impaired Nrf2 signaling induces mitochondrial and RPE dysfunction that results in an oxidative, inflammatory, and pathologic microenvironment.

Preventive therapeutic effect 1: Increasing mitochondrial biogenesis and energy production in RPEs indicated by similar increase in neurons, peripheral leukocytes and hepatocytes (genes: PGC-1a and NRF1/MT-CO1, GPD2 and also Nrf2/ARE genes).

Preventive therapeutic effect 2: reduction in oxidative stress by increasing the activity of HO-1 and other Nrf2/ARE dependent antioxidants.

Therapeutic effect 3: Pleiotropic effect from management of general disorders related e.g. to Metabolic Syndrome (see above) can likely postpone the onset of AMD.

Glaucoma, Optic Neuropathy and Ischemic Optic Neuropathy

Glaucoma is a term describing a group of ocular disorders with multi-factorial etiology united by a clinically characteristic intraocular pressure-associated optic neuropathy. This can permanently damage vision in the affected eye(s) and lead to blindness if left untreated.

The nerve damage involves loss of retinal ganglion cells in a characteristic pattern. The many different subtypes of glaucoma can all be considered to be a type of optic neuropathy.

Preventive therapeutic effect 1: Increasing mitochondrial biogenesis and energy production in optical neurons, ganglia cells, RPEs etc. indicated by similar increase in neurons, peripheral leukocytes and hepatocytes, i.e. genes: PGC-1a and NRF1/MT-CO1, GPD2 and also Nrf2/ARE genes, see Examples 1, 2, and 5)

Preventive therapeutic effect 2: reduction in oxidative stress by increasing the activity of HO-1 and other Nrf2/ARE dependent antioxidants.

Therapeutic effect 3: Pleiotropic effect from management of hypertension and diabetes (see above) can likely postpone the onset of Glaucoma and acute Glaucoma, i.e. Ischemic Optic Neuropathy and/or Optic Nerve Crash. For Ischemic optic neuropathy, see also cerebrovascular accident above.

Increase in glycerol by the use of DGA may alleviate acute glaucoma (see example 5).

Retinitis Pigmentosa

Retinitis pigmentosa (RP) is a prevalent cause of blindness caused by a large number of different mutations in many different genes. The mutations result in photoreceptor cell death of the retina. It has been widely suggested that oxidative stress possibly contributes to its pathogenesis.

Preventive therapeutic effect 1: reduction in oxidative stress by increasing the activity Nrf2/ARE dependent antioxidants.

Preventive therapeutic effect 2: Increasing mitochondrial biogenesis and energy production in rod and cone cells indicated by similar increase in neurons, peripheral leukocytes and hepatocytes (genes: PGC-1a and NRF1/MT-CO1, GPD2 and also Nrf2/ARE genes).

Preventive therapeutic effect 3: Increase in blood pyruvate concentration increases the viability of rod and cone cells.

Sarcopenia

Sarcopenia is described as the age-associated decline in muscle mass. The physical basis for the disorder is a combination of atrophy, loss of the constituent muscle fibers, and defects in energy metabolism in skeletal muscle. Metabolic genes and myosin isoform expression are regulated through the transcriptional co-activator PGC-1a. Changes in muscle metabolism can have systemic effects. It has been shown that defects in skeletal muscle energy metabolism are linked to type II diabetes and glucoregulatory dysfunction.

The compositions and methods of the present invention can alleviate or prevent sarcopenia by activating its three main pathways Nrf2/ARE, PGC-1a/NRF1, and pyruvate formation presented in FIG. 2.

Osteoporosis

Osteoporosis is described as a progressive bone disease that is characterized by a decrease in bone mass and density which can lead to an increased risk of fracture. In osteoporosis, the bone mineral density (BMD) is reduced, bone microarchitecture deteriorates, and the amount and variety of proteins in bone are altered.

The use of DGA can increase the differentiation in mesenchymal stem cells into osteoblasts (instead of developing into adipocytes) by enhancing overexpression of HO-1 gene and thus attenuate osteoporosis by promoting bone formation.

Figure 5:
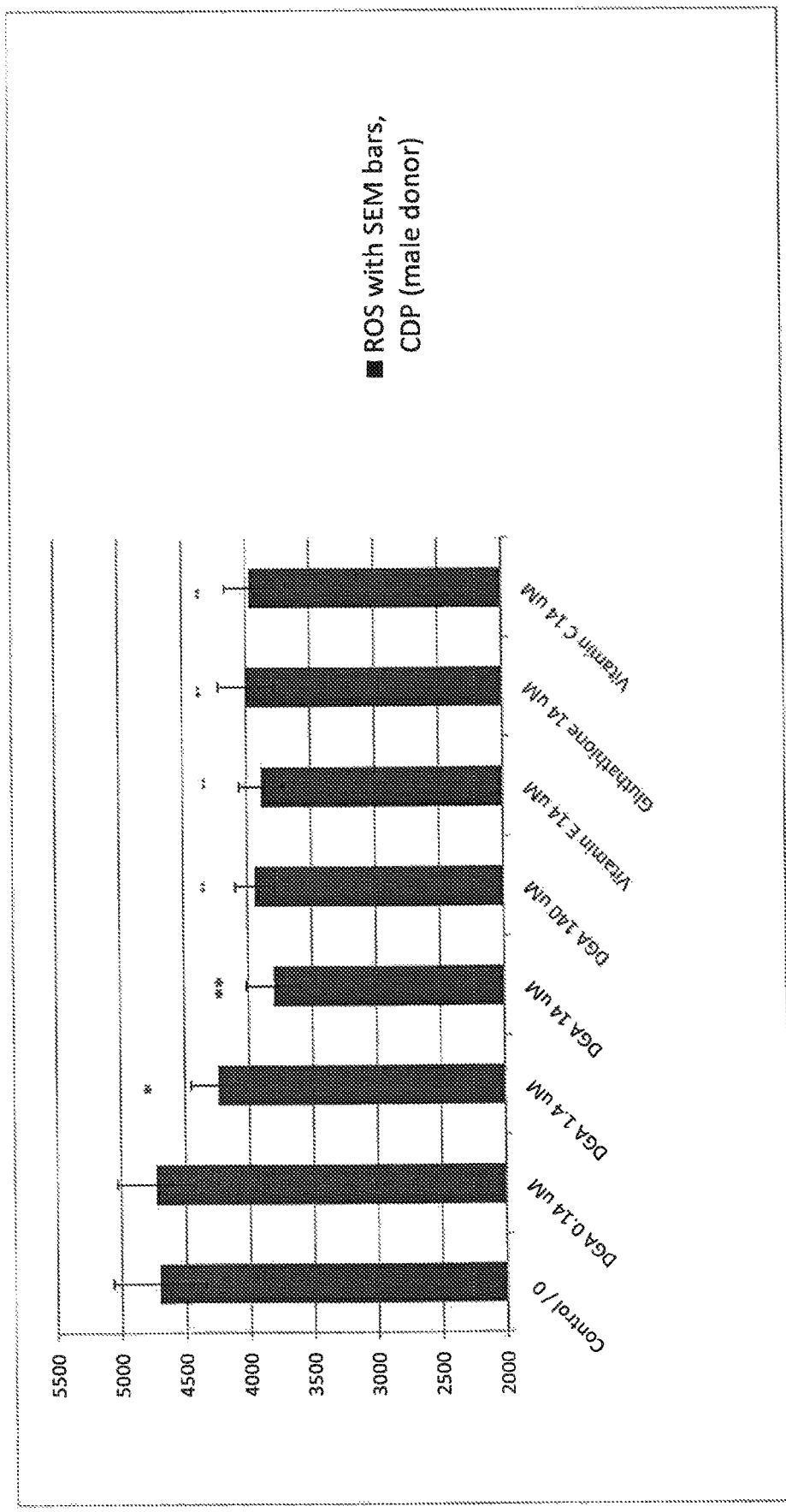
FIG. 5 depicts results from human hepatocytes (male donor CDP) cell culture study. It clearly demonstrates that under moderate metabolic stress (1.5 hours after addition of new medium) DGA reduces ROS production significantly compared to 0 dose/control in standard high nutrition medium. (Later high nutrition medium from Celsis is called "High Medium".) Furthermore the reduction in ROS is DGA dose dependent. Significant efficacy is reached already with 1.4 µM concentration of DGA, and on the other hand 0.14 µM concentration had no effect. Biggest ROS scavenging effect is seen in 14 µM (14 µM dose equals 2 µg/ml concentration). In equimolar comparisons against other known efficient antioxidants (vitamin E, glutathione, and vitamin C) DGA seems to be superior or at least as good ROS scavenger as this peer group. Molecular weight of all others is greater than DGA and thus also the weight of equimolar dose. Cell viabilities were rather volatile in different DGA doses maybe reflecting some cell signaling differences in respect to apoptosis. In general no tendency for big deviations in viability compared to the peer group, thus this analyses gives relatively accurate picture on ROS scavenging abilities also when analyzing ROS per viable cell. Experimental study setup and some analysis on the statistical significance of the results is described in example 1. In here and in all following graphs sign "*" indicates statistically significant difference compared to the control (p-value is clearly less than 5%), and "**" statistically very significant difference compared to the control (p-value clearly less than 1%).
Figure 6:
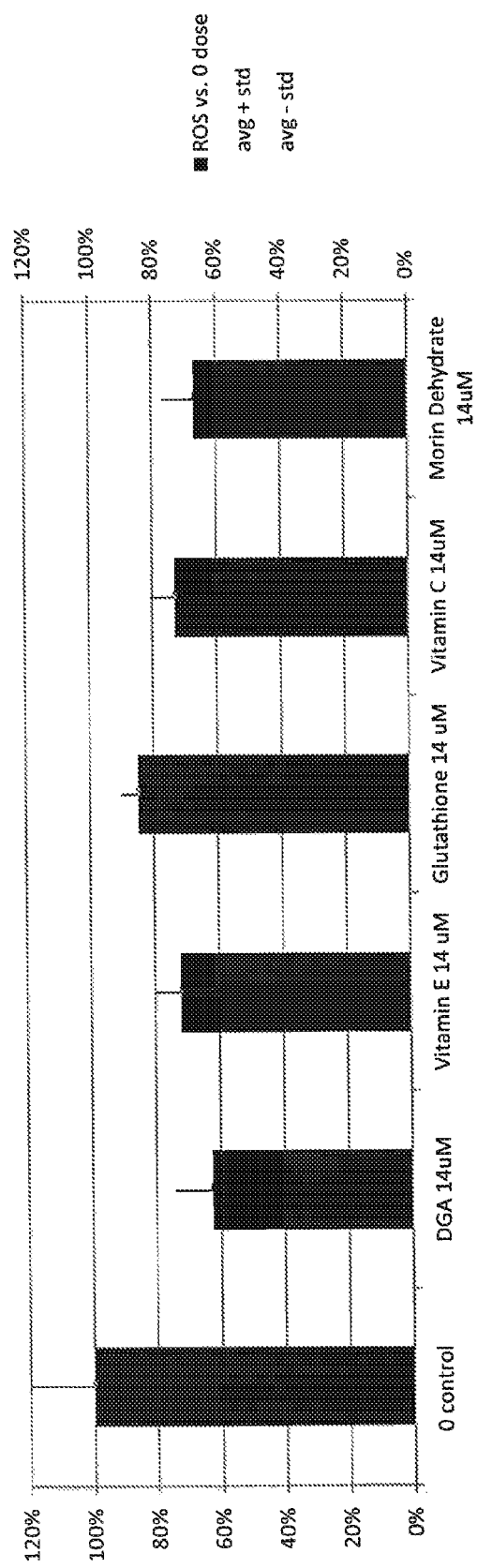
FIGS. 6a and 6b depict results from human cell culture studies, which demonstrate that under moderate metabolic stress DGA reduces ROS production significantly compared to control/0 dose both in standard High Medium (FIG. 6a) as well as in High Medium+0.75 mM palmitic acid diet (FIG. 6b) for female donor JGM. (Later high nutrition medium is called "High Medium".) Furthermore DGA seems to be superior antioxidant in equimolar comparison against most other currently known best antioxidants: vitamin E, glutathione, vitamin C and morin dehydrate. (Molecular weight of all others is greater than DGA and thus also the weight of equimolar dose.) In High Medium only the viabilities of the cell were relatively similar, very small decrease, for all groups except for vitamin E (trolox) and thus the direct comparison of ROS readings is well justified. Vitamin E decreased viability some 23% and thus the ROS per viable cell was greater for vitamin E than FIG. 6 shows. Experimental setup (for this study 4) and analysis on the statistical significance of the results is described in Example 1.
Figure 6:
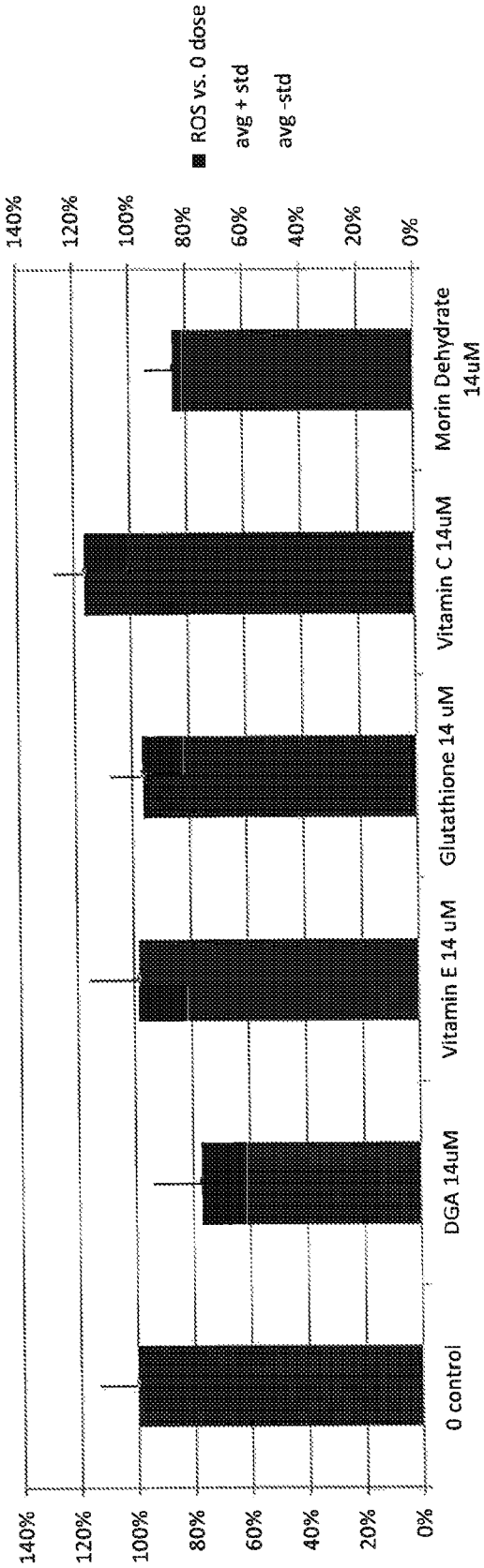
Figure 7:
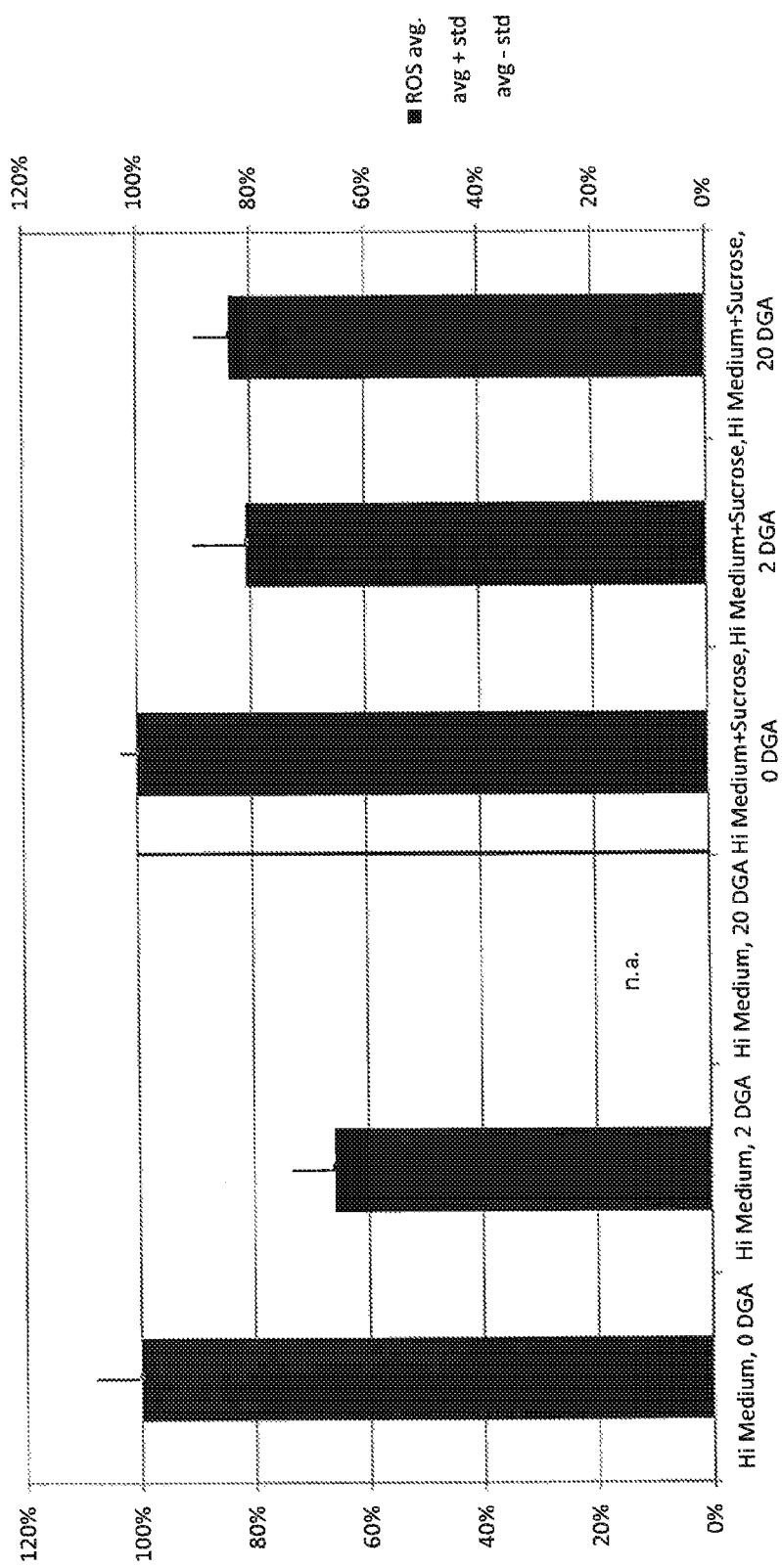
FIG. 7 depicts that DGA reduces ROS per viable compared to control/0 dose in primary human hepatocytes in study 1 for DOD (male donor). ROS per viable cell, DOD (male donor), 24+24+1.5 h, High Medium and High Medium+Sucrose. Results are measured under moderate metabolic stress. 2 DGA=2 µg/ml of DGA=14 µM of DG. 20 DGA=20 µg/ml of DGA=140 µM of DGA. Experimental setup for study 1 and analysis on the statistical significance of the results is described in Example 1
Figure 8:
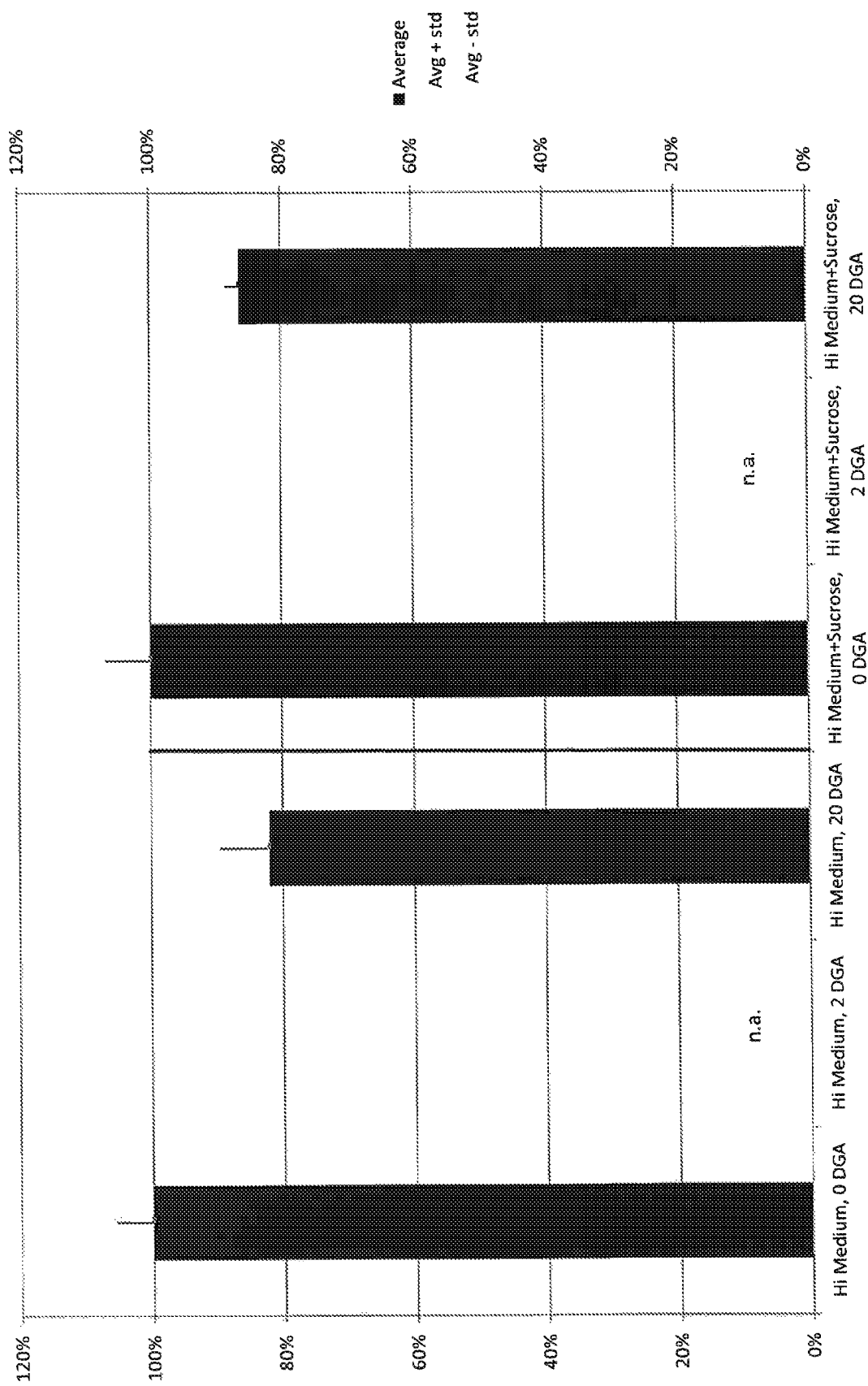
FIG. 8 depicts that DGA reduces ROS per viable cell compared to control in primary human hepatocytes in study 1 for YJM (female donor). ROS per viable cell, YJM (female donor), 24+24+2 h, High Medium and High Medium+ Sucrose. Results are measured under moderate metabolic stress. Experimental setup for study 1 is described in Example 1.
Figure 9:
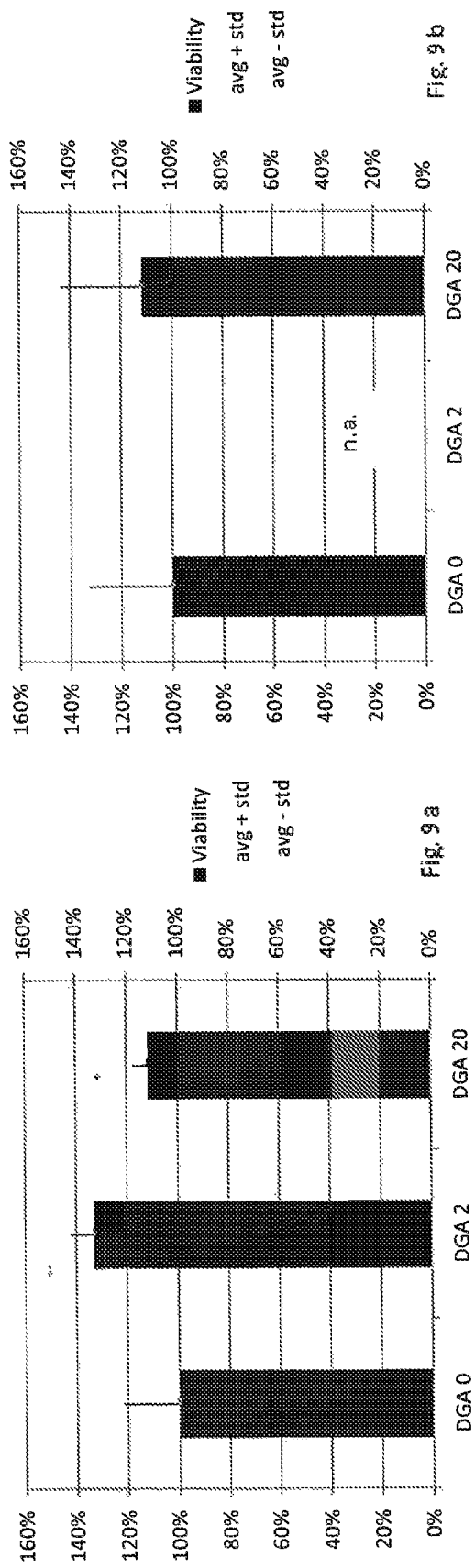
FIGS. 9a, 9b, 9c and 9d depict that DGA can increases viability of primary human hepatocytes in study 1 compared to 0 doses for YJM (female donor) and DOD (male donor). Results are measured under moderate metabolic stress. Experimental setup and analysis on the statistical significance of the results is described in Example 1.
Figure 9:
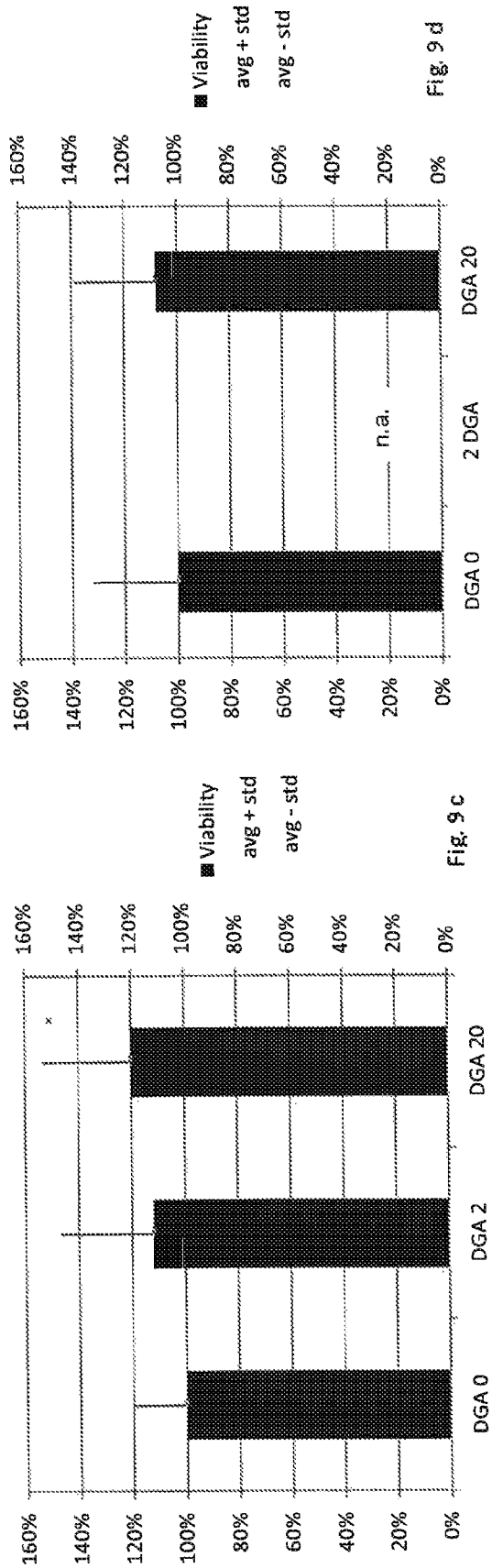

Also enhancing de novo synthesis of vitamin D precursors through facilitating Mevalonate Pathway by increasing NAPDH supply (see FIG. 3b and FIG. 5) may postpone Osteoporosis.

On the other hand the use of DGA also may attenuate osteoporosis by enhancing general metabolism, aerobic energy formation, and related ROS formation by increasing PGC-1a/NRF1 gene expression and daily testing of Nrf2/ARE pathways. Also internal control of excess or in-excess bone formation and turnover may be enhanced by the use of DGA due to increased aerobic energy supply.

De novo increase in pyruvate and other building blocks for anabolic reactions, and simultaneous increase in required energy (ATP, GTP, UTP and CTP) for anabolic reactions by the use of DGA, likely plays a role in preventing or postponing the onset of Osteoporosis.

Osteoarthritis

Osteoarthritis (OA) also known as degenerative arthritis or degenerative joint disease or osteoarthrosis, is a group of mechanical abnormalities involving degradation of joints, including articular cartilage and subchondral bone.

Therapeutic strategy of the use of DGA for osteoarthritis is to enhance the metabolism and renovation of lost tissues, especially collagen. In collagen synthesis vitamin C, in its active reduced form, is an essential co-factor. The ability of the invention to promote regeneration of ascorbic acid from e.g. dehydroascorbate possesses the specific therapeutic effect for preventing and curing osteoarthritis. Additionally the use of DGA aims at elevated efficiency of metabolism by increasing aerobic energy production and by increasing anabolic reactions for all protein, including collagen, synthesis. This task is achieved by increasing mitochondrial aerobic metabolism, i.e. PGC-1a/NRF1 related genes, and resulting increased amount of pyruvate in the cells and blood circulation. Therapeutic effect of the use of DGA is clearly seen in Examples 1.2.3 & 2.3.3 showing clear increase in PGC-1a/NRF1 related genes. Also increase in gene expression of G6PD is an indirect sign of increased NADPH production and indirectly also on elevated anabolic reactions due to Acetyl Coa signaling (FIG. 3b.).

Aging Related Neurodegenerative Diseases in General

On top of general effects for age related diseases described above, additional important general therapeutic effect for neurological dysfunctions is the increase concentration of pyruvate in blood by the use of DGA. CNS needs a lot of energy for sustaining adequate neuronal signaling provided by axons and synapses. Especially axonal activity benefits from increased external energy source from pyruvate. Pyruvate is transported through blood brain barrier via transport system. For preventing age related neuronal diseases Nrf2/ARE expression in astrocytes, and its protective role towards oxidative stress also in neurons is very important. Also positive therapeutic effects from increased physical exercises have been shown to prevent, and at least to decrease the symptoms of Neurodegenerative diseases. The use of DGA provides strongly similar effects than physical exercise, and thus can alleviate and even prevent Neurodegenerative diseases, especially combined with some exercise and normal healthy diet.

As a whole the use of DGA is very suitable in prevention, alleviation, and even curing of a wide range of age related neuronal disorders. Indirect evidence from clinical in vivo testing indicates that the use of DGA possesses very clear effect positive towards the CNS in general. In vitro excitotoxity studies with primary rat cortical neurons confirm that there exists also a protective effect from the use of DGA, as well as statistically significant increase in mitochondrial biogenesis.

Chronic Neurodegeneration

Chronic neurodegeneration is the umbrella term for the progressive loss of structure or function of neurons, including death of neurons. Many neurodegenerative diseases including ALS, Parkinson's, Alzheimer's, and Huntington's occur as a result of neurodegenerative processes. As research progresses, many similarities appear that relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Preventive and alleviating therapeutic effects of the invention follow from above general descriptions for age related neurodegenerative diseases.

Amyotrophic Lateral Sclerosis

Amyotrophic lateral sclerosis (ALS) is a neurodegenerative disease with various causes. It is characterized by muscle spasticity, rapidly progressive weakness due to muscle atrophy, difficulty in speaking (dysarthria), swallowing (dysphagia), and breathing (dyspnea).

Preventive and alleviating therapeutic effects of the invention follow from above general descriptions for age related neurodegenerative diseases.

Additionally in prevention of ALS especially important is the enhanced axonal energy metabolism by the use of DGA. The use of DGA supports wellbeing of oligodendrocytes and their important role in axonal integrity and wellbeing.

Alzheimer's Disease

Alzheimer's disease (AD) is the most common cause of dementia. The term dementia describes a set of symptoms which can include loss of memory, mood changes, and problems with communication and reasoning. Neurodegenerative processes associated with AD are complex and involve many CNS tissue types, structures and biochemical processes. Factors believed to be involved in these processes are generation of ROS, associated inflammatory responses, and the bio-molecular and genetic damage they produce. Furthermore beta-amyloid formation in the brains has been considered one important cause of AD. It has been shown that increased activity of PGC-1a can suppress BACE1 expression that is the enzyme behind beta-amyloid formation. Also activation of the mitochondrial ETC especially MT-CO1, has been related to prevention of AD. The invention can increase PGC-1a and MT-CO1 activity, see Example 5.3.2. Nrf2/ARE pathway activation has been shown to decrease spatial learning difficulties related to AD in mouse model.

The use of DGA has been shown in vivo or in vitro to specifically address to all above mentioned general causes of AD, and thus it possesses at least preventive and/or alleviating effect on AD. Additional effect on prevention of excessive beta-amyloid formation is reduced ER stress by the use of DGA (see graph 2). In literature ER stress has been suggested to be involved in some human neuronal diseases, such as Parkinson's disease, Alzheimer's and prion disease.

Parkinson's Disease

Parkinson's disease (PD) is characterized by the progressive loss of specific cells of the brain region called substantia nigra that produce the chemical messenger dopamine. The current mainstay therapy is the administration of drugs that mimic dopamine action.

The main strategy of the use of DGA is in preventing PD is the administration of therapies aimed to prevent neuronal cell death. The use of DGA has been shown in vitro to protect cortical neurons against excitotoxic insults by NMDA stimulation. Also neurons of substantia nigra possess NMDA receptors and thus it is reasonable to believe that the use of DGA can increase their viability and thus prevent or alleviate PD, and/or even cure early PD.

In literature there are reports that PD might be caused by defect in complex I of the ETS or some other mitochondrial defect. As has been shown the use of DGA enhances mitochondrial metabolism (GPD2, MT-CO1/NRF1) and mitochondrial biogenesis specifically in neurons, and thus can possess therapeutic effect for PD also from that angle. Related to enhanced energy metabolism also PGC-1a has been implicated as a potential therapy for PD.

Additionally also Nrf2/ARE enhancement of the use of DGA can likely be used as efficient PD therapy.

Reduced ER stress and enhanced energy metabolism of neurons might also suppress the formation of Lewy Bodies in pathological conditions of PD.

Multiple Sclerosis

In literature Multiple sclerosis (MS) is described as an inflammatory disease in which the insulating covers of nerve cells in the brain and spinal cord are damaged. This damage disrupts the ability of parts of the nervous system to communicate, resulting in a wide range of signs and symptoms. Preventive and alleviating therapeutic effects of the invention for MS follow from above general descriptions for age related neurodegenerative diseases (e.g. enhancement of Nrf2/ARE pathway).

Especially important in prevention and alleviating the symptoms of MS is the enhanced axonal energy metabolism by the use of DGA. The use of DGA supports wellbeing of oligodendrocytes, and other glial cells in their important role in axonal integrity and wellbeing. Thus the use of DGA enhances communication capabilities of the nervous system that is often impaired in MS.

Huntington's Disease

In the literature it is shown that Huntington's disease (HD) is caused by an expansion of cytosine-adenine-guanine (CAG) repeats in the huntingtin gene, which leads to neuronal loss in the striatum and cortex and to the appearance of neuronal intranuclear inclusions of mutant huntingtin. Huntingtin plays a role in protein trafficking, vesicle transport, postsynaptic signaling, transcriptional regulation, and apoptosis. Thus, a loss of function of the normal protein and a toxic gain of function of the mutant huntingtin contribute to the disruption of multiple intracellular pathways. Furthermore, excitotoxicity, dopamine toxicity, metabolic impairment, mitochondrial dysfunction, oxidative stress, apoptosis, and autophagy have been implicated in the progressive degeneration observed in HD.

Preventive therapeutic effect: Increased expression of PGC-1a and mitochondrial metabolism, combined with reduced ROS generation by the use of DGA work in the direction of postponing the age of onset of HD.

Prion Disease

Prion disease represents a group of conditions that affect the nervous system. These conditions impair brain function, causing changes in memory, personality, and behavior; a decline in intellectual function (dementia); and abnormal movements, particularly difficulty with coordinating movements (ataxia).

Preventive and alleviating therapeutic effects of the invention for Prion diseases follow from above general descriptions for age related neurodegenerative diseases.

In literature specifically ER stress has been suggested to be involved in some human neuronal diseases, such as Prion disease. The use of DGA can reduce ER stress (see FIG. 2) and thus likely alleviate its syndromes or even postpone the onset of this rare disease.

In aspect 1 the invention provides a composition comprising one or more compounds selected from the group consisting of D-glyceric acid, DL-glyceric acid, L-glyceric acid, and hydroxypyruvatic acid and salts and esters thereof for use in a method of treating or preventing a non-communicable disease or disorder related directly or indirectly to mitochondrial degeneration and/or mitochondrial dysfunction, impaired cytosolic catabolism of carbohydrates, deteriorated antioxidant defenses, deteriorated inflammation control, formation of malfunctioning proteins, and/or decreased ability to synthesize precursors of nucleobases adenine and/or guanine.

Aspect 2 provides a composition comprising one or more compounds selected from the group consisting of D-glyceric acid, DL-glyceric acid, L-glyceric acid, and hydroxypyruvatic acid and salts and esters thereof for use in a method of treating or preventing a disease or disorder according to aspect 1, wherein the disease or disorder is a cardiovascular disease, metabolic syndrome, disorder associated with metabolism, cancer, overweight, elevated blood pressure, or a degeneration disease related to the aging process of an organism, or a degeneration disease accelerating the aging process of an organism.

Aspect 3 provides a composition comprising one or more compounds selected from the group consisting of D-glyceric acid, DL-glyceric acid, L-glyceric acid, and hydroxypyruvatic acid and salts and esters thereof for use in a method of treating or preventing a disease or disorder according to aspect 2, wherein the cardiovascular disease is selected from the group consisting of atherosclerosis, myocardial infarction, cardiomyopathy or congestive heart failure, vascular thrombosis and/or embolism, chronic obstructive pulmonary disease, asthma, hemolytic anemia, G6PD and 6PGD deficiency in RBC, sepsis, hemorrhagic shock, and infant jaundice.

Aspect 4 provides a composition comprising one or more compounds selected from the group consisting of D-glyceric acid, DL-glyceric acid, L-glyceric acid, and hydroxypyruvatic acid and salts and esters thereof for use in a method of treating or preventing a disease or disorder according to aspect 2, wherein the metabolic syndrome is selected from the group of diabetes, diabetic neuropathy, and diabetic nephropathy.

Aspect 5 provides a composition comprising one or more compounds selected from the group consisting of D-glyceric acid, DL-glyceric acid, L-glyceric acid, and hydroxypyruvatic acid and salts and esters thereof for use in a method of treating or preventing a disease or disorder according to aspect 2, wherein the disorder associated with metabolism is selected from the group consisting of mitochondrial DNA depletion and other mitochondrial diseases, Leigh syndrome, epilepsy, bipolar disorder, psychiatric disorders and mood disorders, cerebrovascular accident, damage from acute head injury, acute or chronic renal failure, acute or chronic liver failure, splenomegaly, acute or chronic pancreatic failure, chronic auto inflammation and autoimmune syndrome and diseases, psoriasis, impairment in collagen synthesis, osteoarthritis, pre-eclampsia, thyroid disease, chronic fatigue, and fibromyalgia.

Aspect 6 provides a composition comprising one or more compounds selected from the group consisting of D-glyceric acid, DL-glyceric acid, L-glyceric acid, and hydroxypyruvatic acid and salts and esters thereof for use in a method of treating or preventing a disease or disorder according to aspect 2, wherein the degeneration disease related to the aging process of an organism, or the degeneration disease accelerating the aging process of an organism is selected from the group consisting of age related hearing loss such as presbyacusis, noise induced hearing impairment or ototoxic hearing impairment, age related macula degeneration, glaucoma, optic neuropathy, ischemic optic neuropathy, retinitis pigmentosa, osteoporosis, chronic neurodegeneration, amyotrophic lateral sclerosis, Alzheimer's disease, Parkinson's disease, multiple sclerosis, Huntington's disease, and prion disease.

Aspect 7 provides use of a composition comprising one or more compounds selected from the group consisting of D-glyceric acid, DL-glyceric acid, L-glyceric acid, and hydroxypyruvatic acid and salts and esters thereof for enhancing physical training, performance and recovery from exercise.

Aspect 8 provides a composition comprising one or more compounds selected from the group consisting of D-glyceric acid, DL-glyceric acid, L-glyceric acid, and hydroxypyruvatic acid and salts and esters thereof for use as a medicament having an antioxidant activity via enhancing endogenous antioxidant protection of living cells, tissues and/or whole organisms.

Aspect 9 provides a use of a composition comprising one or more compounds selected from the group consisting of D-glyceric acid, DL-glyceric acid, L-glyceric acid, and hydroxypyruvatic acid and salts and esters thereof for increasing the muscle yield and simultaneously decreasing of fat content of a human or an animal, and/or decreasing nutrition consumption without losing muscle mass of an animal, such as a mammal, poultry, and fish.

Aspect 10 provides a composition comprising one or more compounds selected from the group consisting of D-glyceric acid, DL-glyceric acid, L-glyceric acid, and hydroxypyruvatic acid and salts and esters thereof for use in a method of treating or preventing a disease or disorder according to any one of aspects 1 to 6, or enhancing physical training, performance and recovery from exercise according to aspect 7, or for use as a medicament according to aspect 8, or for use according to aspect 9, wherein the composition further comprises a pharmaceutically acceptable excipient.

Aspect 11 provides a composition comprising one or more compounds selected from the group consisting of D-glyceric acid, DL-glyceric acid, L-glyceric acid, and hydroxypyruvatic acid and salts and esters thereof for use in a method of treating or preventing a disease or disorder according to any one of aspect 1 to 6, or enhancing physical training, performance and recovery from exercise according to aspect 7, or for use as a medicament according to aspect 8, or for use according to aspect 9, wherein the composition is in a form of a solution, syrup, powder, ointment, mixture, capsule, tablet, or an inhalable preparation.

Aspect 12 provides a composition comprising one or more compounds selected from the group consisting of D-glyceric acid, DL-glyceric acid, L-glyceric acid, and hydroxypyruvatic acid and salts and esters thereof for use in a method of treating or preventing a disease or disorder according to any one of aspect 1 to 6, or enhancing physical training, performance and recovery from exercise according to aspect 7, or for use as a medicament according to aspect 8, or for use according to aspect 9, wherein the composition is in a form suitable for parenteral, oral, topical or inhalable administration.

Aspect 13 provides a composition comprising one or more compounds selected from the group consisting of D-glyceric acid, DL-glyceric acid, L-glyceric acid, and hydroxypyruvatic acid and salts and esters thereof for use in a method of treating or preventing a disease or disorder according to any one of aspect 1 to 6, or enhancing physical training, performance and recovery from exercise according to aspect 7, or for use as a medicament according to aspect 8, or for use according to aspect 9, wherein the composition is part of a beverage, a food product, a functional food, a dietary supplement, or a nutritive substance.

Aspect 14 provides a pharmaceutical composition comprising an effective amount of one or more compounds selected from the group consisting of D-glyceric acid, DL-glyceric acid, L-glyceric acid, and hydroxypyruvatic acid and salts and esters thereof for use according to any one of aspects 1 to 13.

Aspect 15 provides a method of increasing direct or indirect mitochondrial activity, RNA expression of genes encoding ETS related genes, TCA activity, and/or biogenesis of new mitochondria in a subject comprising administering a composition comprising an effective amount of one or more compounds selected from the group consisting of D-glyceric acid, DL-glyceric acid, L-glyceric acid, hydroxypyruvatic acid and salts and esters thereof to a subject in need.

Aspect 16 provides a method of treating or preventing a disease or disorder in a subject comprising administering a composition comprising an effective amount of one or more compounds selected from the group consisting of D-glyceric acid, DL-glyceric acid, L-glyceric acid, and hydroxypyruvatic acid and salts and esters thereof to a subject in need.

Aspect 17 provides a method according to aspect 16, wherein the disease or disorder is as defined in any one of aspects 1 to 6.

Aspect 18 provides a method of enhancing physical training, performance and recovery from exercise, or reducing radical oxygen species with antioxidants in a subject comprising administering a composition comprising an effective amount of one or more compounds selected from the group consisting of D-glyceric acid, DL-glyceric acid, L-glyceric acid, and hydroxypyruvatic acid and salts and esters thereof to a subject in need.

Aspect 19 provides the method according to any one of aspects 15 to 18, comprising administering the composition comprising one or more compounds selected from the group consisting of D-glyceric acid, DL-glyceric acid, L-glyceric acid, hydroxypyruvatic acid and salts and esters thereof, and a pharmaceutically acceptable excipient. Aspect 20 provides the method according to any one of aspects 15 to 19, comprising administering the composition in a form of a solution, syrup, powder, ointment, capsule, tablet, or an inhalable preparation.

Aspect 21 provides the method according to any one of aspects 15 to 20, comprising administering the composition via a parenteral, oral, or topical application route or by inhalation.

Aspect 22 provides the method according to any one of aspects 15 to 21, comprising administering the composition via a beverage, a food product, a functional food, a dietary supplement, or a nutritive substance.

The present invention is illustrated by the following non-limiting examples. The examples constitute an entirety of findings from various tissues, organs, and whole physiological system from humans and animals in different metabolic states or dosing etc. supporting each other.

EXAMPLES

Example 1

The purpose of first 4 separate in vitro studies with primary human hepatocytes (studies 1-4 in Example 1.1) was to investigate the effect of D-glyceric acid, calcium salt dehydrate (product number: 367494/Sigma-Aldrich, later also DGAcs) to the cell viability and cellular reactive oxygen species (ROS). Also HPA and LGA were tested in some experiments.

Additional 2 studies (5-6 in Example 1.2) were conducted in order to verify and specify results from first 4 studies. On top of viability (LDH) and ROS analyses also gene expression and $NAD^+$/NADH-ratio was measured from human primary hepatocytes in studies 5-6 in Example 1.2.

Furthermore in studies 5-6 the accuracy of cell viability results based on LDH method was double checked with independent estimate on viability using the gene expression of the so called housekeeping genes from the cell cultures. The results of these independent viability tests were very well in line confirming that mostly used LDH estimation method worked well, and also that results from gene expression analyses are consistent in respect to dose responses etc.

Validity of the used ROS estimation method was checked by using known antioxidants treatments that are known to decrease ROS as a positive control of the method. Used ROS estimation method gave very reasonable results with e.g. vitamin C, vitamin E, glutathione, and alfa-lipoic acid.

The age of the human donors in these in vitro studies 1-6 varied between 47-65 years. All had some kind of medical history and specified medical cause of death, i.e. they were not healthy volunteers as was mostly the case in clinical in vivo experiments, see Examples 2.1-2.4.

Example 1.1

Measurement of LDH and ROS from Human Primary Hepatocytes

Materials and Methods

Primary human hepatocytes were purchased from Celsis In Vitro Technologies (1450 South Rolling Road Baltimore, Md. 21227, USA). Primary hepatocytes from altogether 4 donors aged 47 (YJM, female), 57 (DOO, male), 58 (CDP, male), and 54 (JGM, female) were used. According to the information provided by the Celsis, hepatocytes from each donor should have at least 70% viability and more than 5 million viable cells. The medium for the culture of hepatocytes was provided by Celsis. They were InVitroGRO CP (for plating) medium (Z99029) and InVitroGRO HI (for incubation) medium (Z99009). Antibiotics (Torpedo Antibiotics Mix, Z990007) were also from Celsis. The thaw, plating and culture of cells were carried out according to the instruction provided by the Celsis In Vitro Technologies.

The other reagents for experiments were D(−) fructose (Sigma-Aldrich, F0127), D(+)-glucose (Sigma-Aldrich G7528), Dulbecco's phosphate buffered saline (DPBS) (Lonza, BE17-512F), absolute ethanol (ProLab 20821.365) and foetal bovine serum (Thermo Fisher, SV30160). For the cell culture, BD BioCoat™ Collagen I Coated 96-well Black/Clear Plates (354649) were used. Other plastic ware used in this study was purchased from Sarstedt Ltd (Leicester LE4 1AW, UK). Cells were cultured in a cell culture incubator (Sanyo MCO-18AIC) at an atmosphere of 37° C. and 5% $CO_2$.

For the measurement of cell viability after treatment of test compound, CytoTox-One Homogeneous Membrane Integrity Assay kit (Promega, G7891) was used. The Cyto-Tox-One Assay is a rapid fluorescent measure of the release of lactate dehydrogenase (LDH) from cells with a damaged membrane. The number of viable cells correlates to the fluorescence intensity determined by a fluorescence plate reader (Hidex Chameleon V multiplate reader, Hidex Oy, Turku, Finland) with excitation 544 nm and emission 590 nm. For the measurement of cellular reactive oxygen species (ROS), DCFDA Cellular ROS Detection Assay Kit from Abcam (ab113851) was used. Reactive oxygen species (ROS) assay kit (ab113851) uses the cell permeant reagent 2′,7′-dichlorofluorescein diacetate (DCFDA), a fluorogenic dye that measures hydroxyl, peroxyl and other ROS activity with the cell. The activity of ROS was measured by a fluorescence plate reader (Hidex) with excitation/emission wavelengths of 485 nm/535 nm.

This study was conducted in accordance with the relevant standard operating procedures (SOPs) in BioSiteHisto Oy.

Cell Culture

The culture of primary hepatocytes was carried out based on the instructions provided by Celsis. After thawing, the cells were suspended in InVitroGRO CP medium. Thereafter the viability of cells was determined using the Trypan Blue exclusion method. Then the concentration of cells was adjusted using InVitroGRO CP medium, so about 30000-35000 cells/100 μl/well can be seeded in collagen I coated 96 well plate (BD, 734-0248).

After seeding, the cells were cultured overnight in the cell culture incubator (Sanyo MCO 18) at atmosphere of 95% air, 5% $CO_2$ at 37° C. Thereafter, the culture medium for the cells was changed to InVitroGRO Hi (Hi Medium) containing test compound (D-glyceric acid calcium salt dehydrate) at the concentrations of 0, 0.2, 2 and 20 μg/ml (study 1, Table 1.1.1) and 0, 0.4, 2 and 10 μg/ml (study 2, Table 1.1.2).

In study 3 also LGA and HPA were tested and compared to DGA (see FIGS. 11c and 11d) with same doses as in study 2.

In study 4 DGA (molecular weight=106 g/mol) was tested in equimolar doses against other substances with known antioxidative properties, i.e. vitamin E (trolox, T3251 Sigma, molecular weight=431 g/mol), glutathione (G6013 Sigma, molecular weight=307 g/mol), vitamin C (L-ascorbic acid, A4544 Sigma, molecular weight=176 g/mol) and morin dehydrate (M4008 Sigma, molecular weight=302 g/mol). The results from study 4 are presented in FIGS. 6a and 6b.

In studies 2-4 additional diet with 0.75 mM of palmitic acid ("fatty acid diet") was added to Hi Medium. Hi Medium in itself contains ample amounts of glucose and fructose and other necessary ingredients for keeping viability of the cell culture at optimal level.

After 24 h (in study 1) and 20 h (in studies 2-4) incubation medium was renewed. Second renewal of the incubation medium occurred at 48 h in study 1 and at 40 h in other studies. ROS and LDH were measured after 1.5-2 hours after last change of the medium, i.e. in a situation with moderate metabolic stress.

LDH Measurement

The measurement of LDH from medium (leaked LDH) and from cell and medium (total LDH) was carried out according to the instruction provided by the Promega (G7891). The plate was incubated at an incubator to achieve a temperature of 22° C. Thereafter, equal volume of Cyto-Tox-ONE Reagent to cell culture medium (100 μl) was added to each well and mix for 30 seconds. Then they were incubated for 10 min at 22° C., and then 50 μl of Stop Solution was added to each well. After gentle mixing, the fluorescence signal was measured at an excitation wavelength of 560 nm and emission wavelength of 590 nm using the Hidex Chameleon V multiplate reader (Hidex Oy, Turku, Finland).

For the total LDH measurement, all the steps are same except a 2 μl of Lysis Solution (per 100 μl original volume) will be added to the each well to lyse the cells before CytoTox-ONE Reagents will be added.

Cellular ROS Detection

The measurement of cellular reactive oxygen species (ROS) was carried out according to the instruction of Abcam (ab113851). At the end of treatment time point, culture medium was taken away for leaked LDH measurement and cells were washed with 100 μl/well PBS once. Thereafter 100 μl/well of DCDA mix was added and incubated for 45 min at 37° C. in the dark. Then cells were washed once with 1×buffer solution. The fluorescence signal was measured at an excitation wavelength of 485 nm and emission wavelength of 535 nm using the Hidex Chameleon V multiplate reader (Hidex Oy, Turku, Finland).

Calculation and Interpretation of Results

For the LDH and ROS assays, individual values of each measurement were stored and average value of fluorescence signals of various repeats of each treatment at studied time point were calculated and compared. All ROS calculations possessed 6 repeats for all measurement point. Viability (LDH) measurements contained 4-6 repeats depending on the study. Results are presented in FIGS. 6-11. In study 1 (48 h & YJM and DOO) not all the data points for both donors were measured. Those points are marked by not available (n.a.).

Results from Studies 1-4

From FIGS. 5-11 it can be concluded that in standard environment and treatment, i.e. no excess nutrition or starvation DGAcs and also LGA and HPA can modestly increase the viability of human primary hepatocytes (or in any case at least keep it stable). Altogether four donors, two donors from both sexes, were tested.

More importantly DGAcs and also HPA and LGA can decrease ROS levels significantly compared to 0 controls. In used cell model ROS levels are calculated under moderate metabolic stress meaning that measurements are made 1.5-2 hours after the change of the medium, i.e. after giving hepatocytes fresh medium with new nutrition. In study 4 with CDP (male donor, in FIG. 5) and with JGM (female donor), it was shown that two day (48 h+1.5 h) administration of DGAcs decreases ROS significantly. Furthermore this decline is at least as large as with other known strong antioxidants (vitamin E, glutathione, vitamin C, and morin dehydrate). DGA seems to work both in moderate metabolic stress induced by glucose (Hi Medium only) (FIG. 6a, with JGM) and also in moderate metabolic stress induced by beta oxidation (Hi Medium+0.75 mM of palmitic acid) (FIG. 6b, data from JGM). With female donor YJM and in Hi Medium+Palmitic acid LGA and HPA doses of 10 µg/ml reduce the level of ROS by 30-35% compared to control (FIG. 11c). DGA gave same decline in with JGM (also a female donor) with same conditions (FIG. 11a). ROS declined significantly with DGA compared to 0 doses also with other donors as well.

Consistent decline in ROS seen in multiple studies is a clear indication and a follow up of activation Nrf2/ARE antioxidant defense system by the use of DGAcs.

Figure 13:
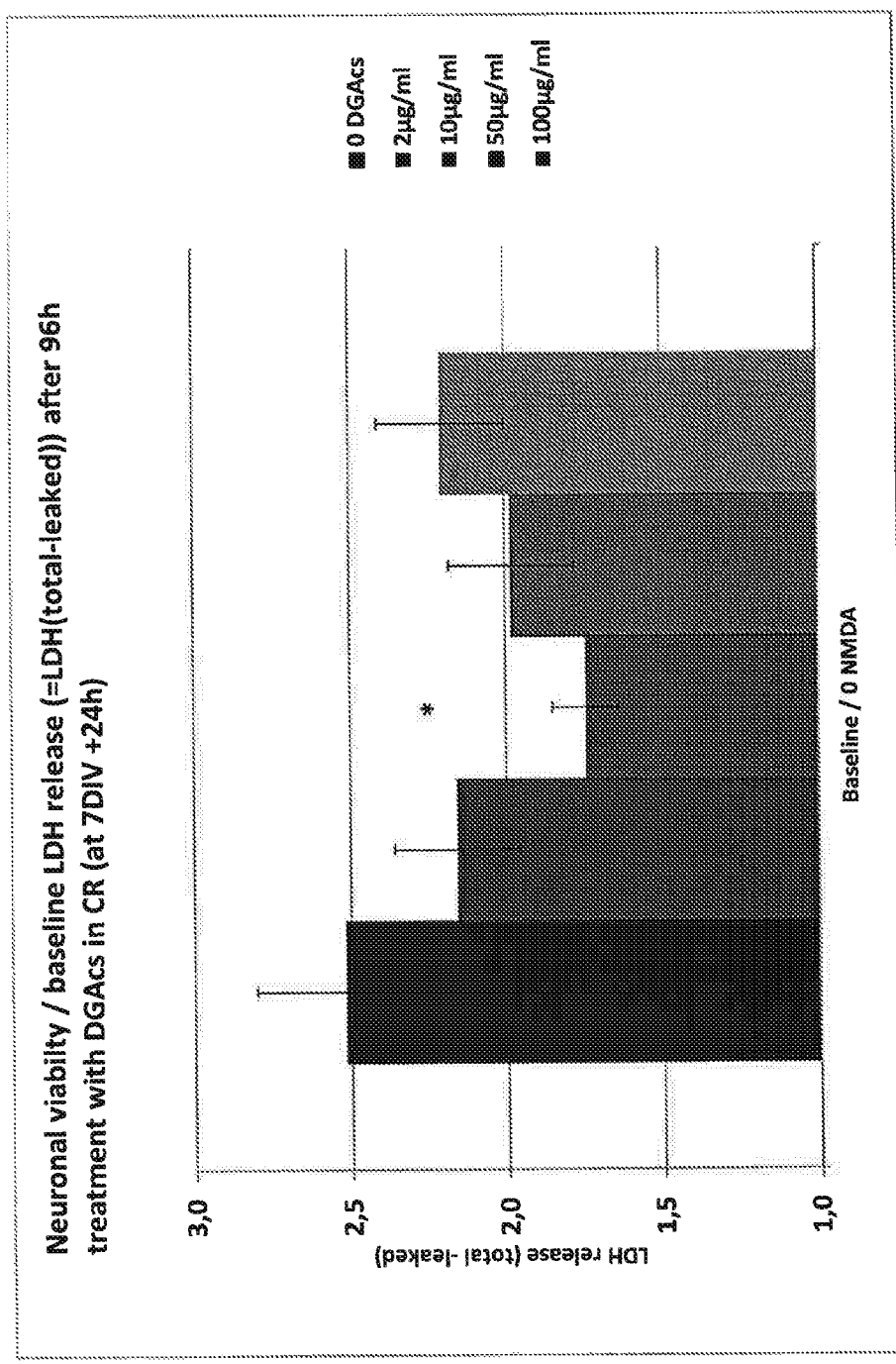
FIG. 13 "Neuronal viability/baseline LDH release (=LDH (total-leaked)) after 96 h treatment with DGAcs in Calorie Restriction (at 7 DIV+24 h)." Cell treatment according to the protocol renewed only 25% of the medium during 5 DIV and 6 DIV, meaning that neurons received only very small amounts of new nutrition. De facto the cell culture was under severe calorie restrictions (CR). This is similar to hepatocytes in "Starving Diet" in Example 1. CR caused dose dependent viability loss also in neurons. Likely explanation is also the same as in hepatocytes: DGAcs administration increases metabolic (anabolic and catabolic) activity in neurons. Anabolic reactions need a lot of energy thus (aerobic) ATP production of neurons and consumption is increased. In a situation with subnormal source of energy (nutrition) this set up leads to enhanced cell cycle control and programmed cell death (apoptosis).

Statistical relevance of each result can be estimated using standard deviations (std) calculated for each study point. Deviations +/−std 0r SEM from calculated averages are presented for all study points (additional +/−line segment on each bar). (In FIG. 6-10 the standard deviations are calculated from individual observations and in FIGS. 5 and 13-14 standard error of the mean (SEM). SEM is otherwise the same as std but it is divided by square root of the number observations (N).). Statistical significance is indicated by * and ** marks (*=P-value<0.05, and **=P-value<0.01).

In some exceptional cases the hepatocytes viability in vitro has increased even by 40-60% and notably in the same test setting, with 0.4 DGA dose, also statistically significant decrease in viability was observed (FIG. 10c). Strong reactions clearly indicate that DGA has significant impact on the activity of the hepatocytes. Additionally, strong viability or cytotoxicity effects seen in FIG. 10c can be interpreted also as increased signaling for apoptosis and/or cell survival, i.e. increased control of cell cycle.

When combining the above viability observations to the observations that hepatocytes kept under calorie restriction (CR=no addition of food, i.e. no change of medium during 48+1.5-2 h) died clearly more likely than control (FIGS. 10a and 10b), it seems obvious that metabolic flux has been increased by the use of DGAcs. Furthermore it seems also that in vitro experiments the cells do not have the means to balance significant impact from DGA use like in vivo. In case of starving diet (CR), the obvious signal for increased apoptosis was the limited amount of nutrition like seen also in below examples with DOO and YJM.

From FIGS. 9a-d it can be seen that the increase in viability in Hi Medium for DOO is statistically significant but for YJM it is not. From FIG. 10c it can be seen that the increase of viability for CDP due to DGA is statistically very significant. Furthermore from FIGS. 10a and 10b it can be seen that starving diet increases cell death the higher the DGA dose has been. This deviation from 0 control is statistically very significant for doses DGA 2 (DOO) and DGA 20 (YJM).

Enhanced control of the cell cycle increases the protection against developing cancer. In combination with enhanced control and activation of intracellular metabolic processes, it also decreases the risk of an onset of several other diseases, including but not limited to auto-inflammatory and auto immune diseases.

Significant decrease in ROS levels, i.e. a clear increase in endogenous defense against oxidative stress, alleviates and prevents the onset of several or even all degenerative diseases (and also cancer). Decrease in ROS in cardiovascular system reduces the risk of cardiovascular diseases e.g. atherosclerosis.

Example 1.2

Measurement of NAD+/NADH-Ratio, Viability and ROS from Human Primary Hepatocytes In studies 5 and 6 same donors were used as in Example 1.1. Cell culturing was according to standard protocols (24 h cycle) and Hi Medium was used like in most experiments 1-4. The 3 donors chosen were DOO (male), JGM (female), and CDP (male). By using same donors we could double check methods used.

Viability and ROS confirmation: Without going into details for repeated viability and ROS results presented already in Example 1.1, we just conclude that DGAcs and also HPA reduced ROS compared to control, and that viability measurement using housekeeping gene expression confirmed LDH viability results.

Example 1.2.1

NAD+/NADH-Ratio in Human Hepatocytes

For the measurement of total NAD ($NAD_{tot}$=NADH+ NAD+) and NAD+/NADH ratio, a NAD+/NADH Quantification kit (MAK037) from Sigma was used. NAD functions as an electron carrier, fluctuating between the oxidized ($NAD^+$) and reduced (NADH) forms. In addition, $NAD^+$ plays critical roles in ADP-ribosylation reaction and as a substrate for sirtuins. According to the Sigma instruction, the NAD+/NADH Quantification kit (Sigma) provides a convenient tool for sensitive detection of NAD, NADH and their ratio without requirement to purify them from samples. Important to notice is that the kit measures NADH and $NAD^+$ in whole cell including all cell organelles and compartments. Mitochondrial matrix is clearly dominant NADH producer from TCA and beta oxidation (consuming naturally the same amount of $NAD^+$ in redox reactions). Importantly, formed NADH is also typically oxidized into $NAD^+$ in the matrix by Complex I in ETC. As is well known anaerobic carbohydrate metabolism, i.e. glycolysis, in cytosol also consumes $NAD^+$ and produces NADH.

Cell culture in NADH-tests was like in Example 1.1. The change of the medium with DGAcs was conducted at 0 h, 24 h and 48 h. NAD measurements were made at 48+3 h in all cases. For CDP also HPA was tested, and for DOO no new nutrition at 48 h was added, i.e. test was conducted in fasting conditions. Results are presented in table 1.2.1 below.

TABLE 1.2.1

Effect of DGAcs and HPA on NAD+/NADH-ratio at 48 h + 3 h

| | | Treatments | | |
|---|---|---|---|---|
| Donor/measurement | Control | DGAcs 1.4 | DGAcs 14 | HPA 14 |
| JGM (new nutrition at 48 h), N = 5 | | | | |
| $NAD_{tot}$ | 0.345 | 0.329 | 0.302 | |
| NADH | 0.280 | 0.289 | 0.294 | |
| NAD+ | 0.064 | 0.040 | 0.009 | |
| NAD+/NADH | 0.229 | 0.139 | 0.029 | |
| Change in NAD+/NADH vs. Control | | −39.3% | −87.2% | |
| P-value | | 4.3% | 0.27% | |
| DOO (no new nutrition at 48 h), N = 3 | | | | |
| $NAD_{tot}$ | 0.238 | 0.243 | 0.240 | |
| NADH | 0.227 | 0.239 | 0.232 | |
| NAD+ | 0.011 | 0.004 | 0.009 | |
| NAD+/NADH | 0.049 | 0.017 | 0.037 | |

TABLE 1.2.1-continued

Effect of DGAcs and HPA on NAD+/NADH-ratio at 48 h + 3 h

| | | Treatments | | |
|---|---|---|---|---|
| Donor/measurement | Control | DGAcs 1.4 | DGAcs 14 | HPA 14 |
| Change in NAD+/NADH vs. Control | | −64.6% | −24.0% | |
| P-value | | 2.7% | 24.5% | |
| CDP (new nutrition at 48 h), N = 5 | | | | |
| $NAD_{tot}$ | 0.235 | 0.231 | 0.232 | 0.232 |
| NADH | 0.217 | 0.222 | 0.225 | 0.222 |
| NAD+ | 0.018 | 0.009 | 0.007 | 0.010 |
| NAD+/NADH | 0.085 | 0.040 | 0.032 | 0.045 |
| Change in NAD+/NADH vs. Control | | −53% | −62% | −47% |
| P-value | | 0.25% | 0.15% | 0.12% |
| Donor/measurement | Control | DGAcs 1.4 | DGAcs 14 | HPA 14 |

P-values are presented in the table

As one can see from table 1.2.1, DGAcs administration clearly decreases NAD+/NADH-ratio at the cellular level as a whole. There is also a clear tendency for all donors that NADH levels increase with DGAcs compared to control. Increased NADH level is a sign that the aerobic ATP energy creating capacity of the hepatocytes is increased. We can indicatively also conclude that ATP production (and thus also its consumption) is increased. This is consistent with the observation of increased apoptosis (cell death) in starving diet compared to normal feeding in hepatocytes (clear result seen in Example 1.1). Cell death in starving diet is caused by increased energy consumption by the hepatocytes and this leads to increased cell death in starving diet conditions.

Cells have to produce ATP all the time for sustaining normal cell functions, but they increase ATP production only, if it is consumed to some task, e.g. physical exercise or thermogenesis. In cell culture at controlled 37° C. there is no need for increased thermogenesis. Neither is there any physical exercise. The probable use of formed extra ATP energy is very likely due to anabolic reactions, e.g. gluco-/glyceroneogenesis and protein synthesis that consume a lot of energy (see FIGS. 3a and 3b, and Example 4). Also increased control and correction of anabolic processes like protein synthesis and enzyme formation in the ER consume energy (e.g. ATP-dependent chaperones). Increased supply of substrates, increase in pyruvate and amino groups (=decrease in urea cycle), for anabolic reactions by the DGAcs administration (shown in Example 2.1-2.3) supports also the idea that excess ATP is consumed for enhanced renovation of enzymes and similar complex macromolecules. In general these processes that increase ATP consumption are beneficial to cells and promote long term health.

Interestingly the results in Table 1.2.1 also show that NADH+NAD+ levels altogether do not increase as much as NADH. Mathematically this means that the NAD+ level decreases in DGAcs groups. This is naturally mostly due to NAD+ reduction into NADH but also increased NAD+ consumption by sirtuins e.g. NAD+ dependent deacetylation of PGC-1a can be one consistent explanation. From other examples (see below) we can clearly see that the use of the DGAcs induces increase in aerobic metabolism and also mitochondrial biogenesis, and it is well known that deacetylation of PGC-1a activates a flow of genes that up regulate aerobic metabolism. (From human in vivo leukocyte gene expression we can see that PGC-1a and related energy metabolic genes are up regulated by DGAcs.)

Importantly, this is consistent with the notion that cytosolic NAD+ generating capacity of the cells increases by the DGAcs administration and that at the same time DGAcs decreases NAD+ levels as a whole in aerobic cells. In fact the use of DGAcs clearly increases cytosolic NAD+ generating capacity by increasing MA-shuttle intermediates (due to significant pyruvate increase, see Example 2.3) and also due to increase of GP-shuttle formation reflected by increased gene expression of GPD2, in Example 2.2. (GPD2 up regulation is also very likely due to increased substrate formation by mitochondrial beta oxidation. Liberating fatty acids for beta oxidation increases intracellular concentration of free glycerol, which is phosphorylated by kinase enzymes (located on the outer mitochondrial membrane) into G-3-P (see FIG. 1b and Example 4 below). Increased activity of MA- and GP-shuttles by the Invention increases cytosolic NAD+ levels when needed and clearly more rapidly compared to without using the DGAcs. Cytosolic NAD+ must be generated e.g. in order to keep the flow of glycolysis active. Otherwise there is a risk of generating AGEs (advances glycation end products). AGEs, are substances that can be a factor in the development or worsening of many degenerative diseases, such as diabetes, atherosclerosis, chronic renal failure and Alzheimer's disease Example 1.2.2

Gene Expression from Human Hepatocytes

For DOO, JGP and CDP also gene expression analyses was made. In the used technology (see Example 2.3.3 for details) the expression of so called housekeeping genes is measured as well as the expression of some selected genes. The expression of the housekeeping genes, by definition, is always high. The results from their measurements from hepatocyte lysates were volatile but statistically meaningful. Housekeeping gene expression indicated very similar changes in viability that also LDH studies had pointed out earlier.

TABLE 1.2.2

Indicative gene expression results from hepatocytes lysates

| | Gene expression deviation from control, % increase or decrease | | |
|---|---|---|---|
| Donor/Gene | DGAcs 1.4/ Control | DGAcs 14/ Control | HPA 14/ Control |
| JGM, N = 5 | | | |
| HO-1 | 54% | 50% | n.a. |
| CYP2B6 | 8% | 3% | n.a. |
| PGC-1a | 12% | 42% | n.a. |
| DOO, N = 5 | | | |
| HO-1 | 83% | 21% | 1% |
| CYP2B6 | 29% | 49% | 7% |
| PGC-1a | 45% | 1% | −2% |
| CDP, N = 5 | | | |
| HO-1 | n.a. | n.a. | n.a. |
| CYP2B6 | 38% | 45% | n.a. |
| PGC-1a | 5% | 20% | n.a. |

Combined p-value <0.05 for HO-1 and CYP2B6, for PGC-1a P-value was <0.10

For combined data in DGAcs 1.4 µM group vs. the control both HO-1 and CYP2B6 were statistically significantly different from control (P-value is approximately 1%, i.e. the result was statistically very significant). Combined test for PGC-1a yielded P-value of some 10%, which indicates that also PGC-1a was activated compared to control. Importantly the deviations from relevant controls were in line with in vivo results with leukocytes (table below and Example 2.3.3).

We can conclude that there is a clear tendency for e.g. inducible heme oxygenase (HO-1) to rise in hepatocytes after the use of the DGAcs (an indication of Nrf2/ARE activation), and that the expression of the master regulatory gene of energy metabolism, PGC-1a seems to rise in hepatocytes also (see FIG. 2 for the relevance of these genes). Even more convincing evidence on the ability of the use of DGAcs to activate these pathways and also e.g. on CYP2B6 is presented in the next example, the in vivo clinical experiment. Interestingly inducers of CYP2B6 are used in e.g. as anti-epilepsy drugs and mood stabilizers, e.g. management of Bipolar Disorder.

Example 2

In vivo Clinical Studies

Altogether three short 1-4 day in vivo clinical tests with varying doses were conducted, and additionally several longer term tests ranging from 11 day to 8 weeks (Example 2.1). Additionally, after received full proof of efficacy and safety, also higher and also acute doses were tested (Example 2.2). The doses used in these clinical tests are at maximum less than 10% of the safe doses with rats in the below described 3 week tests.

In the first set of experiments presented in Example 2.1 all the blood measurements were conducted next day after last administration of DGAcs. In the longer experiments doses (3-5 mg/kg) were typically taken once a day (preferably in the evening before going to bed). In shorter 1-4 day experiments doses were taken twice a day, in the morning and before going to bed. In all experiments in Example 2.2 the last DGAcs dose was double in size (some 8 mg/kg), and it was taken in the same morning as the collection of blood samples. Relatively high dose and short time to measurement was chosen in order to see clearer dose response in gene expression from peripheral leukocytes, and also from collected plasma samples.

Example 2.1

First Set of Clinical in vivo Experiments

Eight (8) persons completed controlled clinical testing with standard 10-12 hour fasting diet (f) blood test (sample analytics by United Medix Laboratories, Finland). There were four different types of clinical tests: first a 3 week test with low dose of DGA (N=3), secondly one 11 day test with bigger dose (N=1), and finally a 4 day test with high dose (N=4) and with low dose of DGA (N=2). Subjects 1 and 4 (in table 3) did the first three week test and then some months later also the separate 4 day test.

Daily doses varied from 3-4 mg/kg/day in 3 week test to 6 mg/kg twice a day in 4 day test. General rule in the studies was that the shorter the period the higher the dose. In three week clinical tests fasting blood standard lipid panel and other basic readings were measured at the beginning and at the end of the test period.

In the 4 day tests very wide fasting blood panel consisting of 25 different metrics was measured (see table 3 below), and additionally for some participants full blood count to measure more precise effect on erythrocytes and hemoglobin was carried out.

Unlike in hepatocytes study (Example 1) clinical experiments were conducted in a fasting diet situation. Challenges for obtaining meaningful health indications from DGAcs administration arises from the fact that the study persons (aged 41-73) were all healthy volunteers, i.e. the blood values were mostly at very good levels, and thus improvements from the control are hard to achieve. Nevertheless the results from clinical testing show clear signs on the efficacy of DGA in improving systemic redox state of especially the cardiovascular system and also clear indications of increased overall metabolic flux. Specific markers for functioning of liver, kidneys, pancreas and spleen show improvement in general (see Table 4). The results from 10-12 hour fasting blood test after 4 day administration for lean and healthy volunteers are presented in Table 3.

TABLE 3

Four day human trial with 5-6 mg/kg/twice a day. DGA calcium salt was mixed to 1 dl of water in advance. Healthy subjects with BMI <24.9, i.e. normal weight/lean. (N = 4) Measurements on Monday and Friday morning, standard fasting blood test.

| | 4 day changes from zero controls, % | | | |
|---|---|---|---|---|
| | S1 | S2 | S3 | S4 |
| S-Afos | −2.1% | 0.0% | −5.8% | −6.3% |
| S-alat | −13.6% | −13.3% | 57.8% | 11.1% |
| S-Alb | −2.2% | 0.0% | 0.0% | −2.2% |
| S-Amyl | 64.9% | 6.3% | −6.7% | −73.8% |
| S-Asat | −33.3% | −40.9% | −7.7% | −4.3% |
| S-Bil | −19.1% | −22.8% | −58.1% | −12.6% |
| S-Bil-Kj | −17.4% | −23.3% | −58.4% | −8.8% |
| S-Cal | −1.7% | 0.0% | −2.2% | −2.5% |
| S-CK | −21.7% | −24.7% | −65.9% | 3.8% |
| fS-Fe | −27.9% | −22.5% | −72.0% | −5.2% |
| fS-Gluk | 1.9% | −9.8% | −8.9% | 0.0% |
| S-GT | 11.1% | 22.2% | −9.5% | −6.7% |
| S-K | −2.3% | 10.8% | 7.0% | −4.7% |
| fS-Kol | −1.6% | −5.7% | −6.4% | −3.2% |
| HDL | −4.5% | −3.3% | −9.1% | −5.9% |
| LDL | 2.4% | −10.7% | −5.3% | −9.5% |
| fS-Krea | −4.4% | −11.1% | −5.0% | −8.5% |
| S-LD (LDH) | −3.7% | −4.2% | n.a. | −4.8% |
| S-Mg | −2.4% | 6.3% | −3.6% | 2.2% |
| S-Na | −1.4% | −2.1% | −2.1% | 0.7% |
| fS-Pi | 18.3% | 9.3% | −6.0% | −6.4% |
| fS-Transf | 10.0% | 0.0% | 0.0% | −4.2% |
| fS-Transferr.satur. | −32.3% | −23.3% | −72.4% | 0.0% |
| fS-Trigly | −4.6% | 39.7% | 35.4% | 50.4% |
| S-Uraat | −5.2% | −3.2% | −12.0% | −9.9% |
| fS-Urea | −7.1% | −15.9% | 12.8% | −7.3% |

Longer run 3 week tests with 3-4 mg/kg/day dose were conducted with subjects S1 and S4 (from Table 3), and additionally on subject S6. Similar 11 day test with 2×4 mg/kg/day dosing was carried out for S5. In these tests only fS-Kol, fS-Trigly, fS-Glucose, fS-Krea and fS-GT were measured (and blood pressure for S4 and S5, FIG. 12). Subjects S7 and S8 did also 4 day trial but with only 2×3 mg/kg/day dose and did not bring any significant changes in observed 25 blood metric (in Table 3) except possibly with slightly increased blood triglycerides (fS-Trigly) and lowered blood uric acid levels (S-Uraat).

Putting S1-S6 results together like in Table 3, one can observe clear tendency towards lower cholesterol (fS-Kol) for all subjects, and some tendency towards lower sodium (S-Na) and glucose (fS-Glucose) levels for all. Creatinine kinase (S-CK) was on average clearly lowered after the use of DGAcs.

Putting S1-S8 together one can observe some tendency for increase in blood triglycerides level. This was not the case for 2 out of 8 subjects but for 5 subjects the increase was in the range of 25-50% percent.

When interpreting the significance of the results from healthy volunteer testing, it should be noted that the study subjects S1-S4 in Table 3 had their blood counts at relatively optimal levels before DGA administration. As an example blood glucose for all subjects was in the recommended range of 4.2-6.0 mmol/l. Specifically subjects S1 (5.2 mmol/l) and S4 (4.7 mmol/l) in Table 3, whose blood glucose did not decline due to DGA administration, had no physiological need for reduction in fasting state blood glucose concentration. Also S-Asat, S-Bil, S-Bil-Kj, S-Fe, fS-Krea, S-Na and S-Uraat levels were at normal ranges for all subjects. For more information and interpretations of various metrics see table 4 below.

In a summary, already in 4 days surprisingly big changes in above described blood metrics can be observed, and they are basically always to a direction indicating improved health from the use of DGAcs. This is remarkable and proves the enhancements achieved with DGAcs administration in 1) the redox-state of the cells, i.e. by re-oxidizing $NADH+H^+$ to $NAD^+$, 2) in the velocity ATP production (and metabolic flux of sugars and fats), 3) antioxidative state of the cells, e.g. by hindering excessive radical oxygen species (ROS) formation from oxidative phosphorylation (OX-PHOS) and, 4) protein synthesis and enzyme assembly, especially seen (but not limited to) in assembly of heme (Fe) containing enzymes typically related to oxidative metabolism. (Increased Fe use for proteins is seen particularly in next example (2.2) in which HO-1 enzyme activity and related catabolism of heme into biliverdin and further to bilirubin+Fe+CO (see FIG. 4) has been increased by higher and more acute DGAcs dose, and despite this increase of free Fe output, the Fe concentration in blood decreases in healthy volunteers.)

Example 2.2

Extended Administration and Control Period for S4

For Subject 4 (S4) in Example 2.1, the 4 day test period was prolonged by 8 weeks with reduced, only once a day 5 mg/kg/day administration before going to bed. Additionally in order to have an understanding that the results in the 8 week test were due to the administration of the Innovation, an additional negative control measurement without DGAcs after 2 weeks and 2 days was made (+2 days due to alleviating doses see below). The idea was to see, if the beneficial effects seen in 4 day treatment prevailed in longer term (positive control).

One additional point of interest was to check that whether the elevated blood triglycerides come down from slightly elevated levels after first 4 days. Blood triglycerides seem to increase for most of the tested subjects in the short run compared to the controls. This increase is likely mostly due to the increased de novo biosynthesis of fatty acids and triglycerides by the liver for increased mitochondrial beta oxidation (see FIG. 3a and Example 3). De novo synthesis produces mostly medium chain fatty acids that are easily metabolized e.g. in beta oxidation and are considered to possess even health effects, and thus the observed increase in fS-Triglys can be health promoting.

TABLE 2.2.1

Follow up test, 8 week positive control, followed by 2 week negative control. DGAcs was mixed to water in advance.
(N = 1, healthy female, age 52 years)
Measurements in the mornings at 07:35-07:50,
standard fasting blood test, changes from previous observation, %

|  | S4 (4 day test) | | S4 (after 8 weeks) Positive Control | S4 (2 week follow up) Negative Control |
|---|---|---|---|---|
|  | 0 day | 4 day | +8 weeks | +2 weeks |
| S-alat, change |  | 11.1% | 85.0% | −35.1% |
| S-Asat, change |  | −4.3% | 31.8% | 24.1% |
| AST/ALT | 1.28 | 1.10 | 0.78 | 1.44 |
| S-Bil | 11.1 | 9.7 | 7.2 | 10.2 |
| S-Bil, change |  | −12.6% | −25.8% | 41.7% |
| fS-Fe | 21.3 | 20.2 | 15.6 | 15.1 |
| fS-Fe, change |  | −5.2% | −22.8% | −3.2% |
| fS-Trigly | 1.15 | 1.73 | 1.35 | 1.11 |
| fS-Trigly, change |  | 50.4% | −22.0% | −17.8% |
| S-Uraat | 273 | 246 | 247 | 295 |
| S-Uraat, change |  | −9.9% | 0.4% | 19.4% |

In Table 2.2.1 only some results from the blood samples are presented. AST/ALT: the tendency for all tested of an improvement in AST/ALT-ratio seems to prevail very clearly also in the longer term, and importantly AST/ALT returns back to starting levels 2 weeks after stopping the administration. Bilirubin: the tendency for all tested for a reduction in blood bilirubin seems to prevail very clearly also in the longer term, and importantly they return back to starting levels 2 weeks after stopping the DGAcs administration. These results with bilirubin (and HO-1) are very interesting because, as seen in next Example 2.3, HO-1 enzyme can be activated and increase bilirubin production, which is the final output from heme degradation to biliverdin. Blood iron (Fe): Fe continued to decline during the 8 week period and reached the same magnitude of decline as for other subjects in already 4 days (table 3). For some unknown reason Fe did not return to levels prevailing before the experiments. fS-Trigly: As seen from Table 2.2.1, triglycerides level drops significantly in 8 weeks from elevated level after 4 day administration. Interestingly the level of 1.35 seems to remain at slightly higher levels than without the use of DGAcs (=1.11-1.15). Slightly elevated blood triglycerides in humans are probably an indication on increased mitochondrial beta oxidation (like seen in example 3 with rats). S-Uraat: down with DGAcs in the short and longer run. Back to original levels after stopping the administration.

Withdrawal symptoms: Maybe the most important result from this 8 week follow up test with S4 was seen when stopping daily 5 mg/kg/day administration. After 36 hours without DGAcs dose, negative symptoms of the "withdrawal" started. They were very clear but not severe including bad feeling inside the head and overall dizziness and uneasiness. It was decided that S4 can receive some alleviating small doses of DGAcs, and that the 2 week test period without the use of the DGAcs is postponed by these days. First alleviating dose (3mg/kg) was received after 48 hours. The "balancing" effect was felt very fast. Already in 30 second to one minute general feeling of S4 returned more or less to normal. Fast alleviating physical effect was likely related to strong signaling to the body that the beneficial substance for energy metabolism and oxidant defense is still available (see FIG. 1.b description). Another alleviating dose of only 1.5 mg/kg was taken during the next day, and there after started the 2 week negative control period. No adverse symptoms of withdrawal were felt after these two alleviating doses. (Note: in 4 day test subjects S1-S3 had experienced slight headache in 24 hours after stopping the twice a day administration.)

Example 2.3

Clinical in vivo Follow up Test with Additional Gene Expression Analyses, Glucose Tolerance Test, and Plasma Metabolite Concentration Analyses In earlier in vivo experiments (Example 2.1 and 2.2) the last DGAcs was taken in previous night. In this Example the last dose was double in size (=some 10 mg/kg), and it was taken in the same morning as the collection of blood samples. Higher than "normal" therapeutic dose and short time to blood measurement was chosen in order to see a clearer dose response compared to zero control. On top of very wide blood panel, like in Examples 2.1 and 2.2, also gene expression analyses from peripheral leukocytes (Example 2.3.2 below), and concentration analyses from collected plasma samples (Example 2.3.3) was conducted. Also glucose tolerance test and related insulin measurements (Example 2.3.4 below) was conducted. By comparing results of subject 1 (S1) from Example 2.1 and in Example 2.3.1 (below), it is fairly straightforward to see that this "high dose and immediate response strategy" was efficient, and it produced even very important deviations in some parameters due to different administrations.

Example 2.3.1

Wide Blood Panel and Blood Count in Acute Test

In this Example the 4 day experiment in Example 2.1 was extended into 4.5 day experiment by additional DGAcs dose in the morning before blood measurement. Same wide fasting blood panel consisting of 25 different metrics and full blood count was measured for all participants (sample analytics by United Medix Laboratories, Finland).

Two healthy volunteers (S1 and S9) and two (otherwise healthy) volunteers using statin medication (S10 and S11) were chosen for the experiment. The test set up was double blinded. S1 had participated in the earlier 4 day experiment (see Table 3 above and also to a 3 week pilot testing) and served as an important positive control on the efficacy of the DGAcs. Statin group on the other hand was chosen as some kind of a negative control because statins to some extend can possibly counter act the positive effects of the DGAcs and on the other hand also have similar health effects. Statins suppress mevalonate pathway by inhibiting HMG Coa reductase activity and also disturb balancing of cellular $NADPH/NADP^+$ levels (FIGS. 3b and 4). On the positive side, statins have been shown to increase expression of inducible heme oxygenase (HO-1) like the DGAcs can also do, and also to increase LDL-receptor synthesis like the DGAcs can also do through Nrf2 pathway activation. Statin treatment group was not expected to yield positive results but possibly vice versa. For S10 the statin dose was halved two weeks before the test from 20 mg to 10 mg (Simvastatin). For S11 statin treatment was kept at 20 mg per day (also Simvastatin).

TABLE 5

4.5 day human trial with 5 mg/kg/twice a day, and last dose 10 mg/kg in the morning. DGAcs was mixed to water in advance. Two healthy male subjects with good physical condition and lean, age 47 and 50. (N = 2)
Measurements 2.5 hours after last dose
Standard fasting blood test.

|  | S1 (4 day) | S1 (4.5 day) | S9 (4.5 day) | |
|---|---|---|---|---|
| S-Afos | −2% | 8% | 12% | |
| S-alat | −14% | 18% | −36% | |
| S-Alb | −2% | 5% | 10% | Ratio AST/ALT declines |
| S-Amyl | 65% | −5% | −3% | significantly for most of the |
| S-Asat | −33% | −14% | −43% | tested. |
| S-Bil | −19% | 4% | 41% | Important deviation from |
| S-Bil-Kj | −17% | 7% | 40% | earlier. |
| S-Cal | −2% | 4% | 3% | Important deviation from |
| S-CK | −22% | −14% | −36% | earlier. |
| fS-Fe | −28% | −2% | −20% | Deviation in S-Cal prob. due to |
| fS-Gluk | 2% | −2% | 4% | admin. |
| S-GT | 11% | 20% | −9% | Ck down for basically all |
| S-K | −2% | −2% | −13% | tested. |
| fS-Kol | −2% | 4% | −8% | Fe down despite bilirubin |
| HDL | −5% | 1% | −1% | and HO-1 up. |
| LDL | 2% | 5% | −9% | Increase is a deviation from |
| fS-Krea | −4% | 3% | 9% | general pattern. |
| S-LDH | −4% | −4% | −7% | Indicates decreased cell death. |
| S-Mg | −2% | 5% | 0% | |
| S-Na | −1% | 1% | 1% | |
| fS-Pi | 18% | 13% | −15% | |
| fS-Transf | 10% | 5% | 8% | |
| fS-Transferr.satur. | −32% | −6% | −23% | |
| fS-Trigly | −5% | −3% | −5% | |
| S-Uraat | −5% | 4% | −1% | Blood urea declines for 8 out |
| fS-Urea | −7% | −8% | −39% | of 9 subjects. |

Similarities compared to 4 day non-acute dose test: In Table 5 the percent changes compared to 0-control from 4.5 day administration are presented for healthy volunteers S1 and S9. As a comparison also the results from 4 day treatment for S1 are presented in the first column. For S1 all the values in all zero control measurements and in measurements after DGAcs treatment were in the recommended ranges indicating good general health. Nevertheless there were again some clear indications towards even better general health: 1) AST/ALT (ratio) declined from 1.32 to 0.96 (earlier in 4 day test the decline was 1.36 to 1.05) indicating improved function of the liver, 2) creatine kinase (S-CK) declined 14% (−22% earlier) indicating improved heart and muscle function, 3) blood LDH declined 4% (−4%), and 4) finally blood urea decline 7% (−8%) indicating improved renal function.

Deviations compared to 4 day non-acute dose test: There are also some important deviations in S1 results compared to the earlier results from different administration before the blood sample. Importantly these deviations, in this high dose experiment, were to the same direction for also S9 (in table 5), S10 (data not shown) and S11 (data not shown). Deviations from 4 day test: 1) bilirubin and bilirubin conjugate were both up this time indicating increased HO-1 activity, 2) calcium level in the blood (S-Cal) was now up slightly compared to clear tendency to decline in earlier studies, which is very likely due to relatively high dose of calcium salt containing 15% of calcium, and finally 3) blood creatine was now up for all 4 subjects tested, earlier creatine (fS-Krea) levels tended to decline for all tested (see table 3).

For statin group (S10 and S11) there was very little internal or external consistency (except for above mentioned measurements), which was rather expected. The DGAcs does not work well, at least in short term and in high dosing, with statins because some natural pathways are inhibited; secondly because in high dosing HO-1 expression is clearly activated by the DGAcs. Statins have been reported to elevate HO-1 expression as well, and thus even the zero controls of the statin group already contain this important therapeutic element from high dosing of the DGAcs, which makes it more difficult to reveal any differences between the treatment and the control groups.

In statin group nevertheless, increased level of blood triglycerides (+83.5% for S10 and +25.6% for S11) is an additional element in line with results of S2, S3 and S4 in Table 3. Increased blood triglycerides (TGA) likely indicate increased synthesis of TGA by the liver and their transportation for use in beta oxidation for other tissues e.g. muscles and heart (see also Example 3). For S1 and S9, with relatively high aerobic capacity and good physical conditions, it is hypothesized that muscle cells have developed their own glyceroneogenesis and fatty acid synthesizing capacity, and thus the need to transport them from the liver is reduced.

It can be deduced from above clinical examples 2.2 and 2.3.1: The DGAcs can reduce oxidative stress of the cardiovascular system also in the long term low dose administration. This reduction is likely due to daily stimulation of Nrf2/ARE systems as well as several other factors like reduction in blood pressure (FIG. 12). In higher dose and immediate response test the internal oxidative defense mechanisms, like increase of bilirubin/HO-1, are acutely activated indicating some oxidative stress. After analyzing the gene expression results in the next Example 2.3.2, we will give the therapeutic interpretation on these seemingly conflicting results from the use of the DGAcs.

Example 2.3.2

Gene Expression from in vivo Blood Samples

In the above 4.5 day experiment samples of peripheral leukocytes were collected from S1 and S9 in fasting condition (0 h), and also 1 hour (1 h) after taking 75 grams of glucose (Glutole, Biofile Pharma, 330 ml) for glucose tolerance test. Additional gene expression measurement was done from a separate 12 hour treatment for S1 and S9. In the 12 h test only two last doses of DGAcs were administered, first dose 12 h earlier than the blood sample, and the last/second dose 2.5 h earlier in the same morning (like in 4.5 day experiment). For the statin group, S10 and S11, only one gene expression measurement was done in two hours after the fasting blood sample. Leukocytes were immediately separated from blood samples, and after separation immediately lysed by stop solution and stored in freezer according to instructions by the service provider.

Use of peripheral leukocytes as biomarkers of diseases: it is generally known that peripheral leukocytes and platelets can act as biomarkers of mitochondrial dysfunction associated with several diseases including diabetes, neurodegenerative diseases, atherosclerosis and cancer. For example, in a study of mononuclear cells in type2 diabetes showed that the mitochondrial mass was decreased and that the mitochondria were hyperpolarized. Mitochondrial complex I activity was found to be decreased in aged platelets and those obtained from patients with Alzheimer's disease had higher mitochondrial membrane potential than controls. Furthermore, platelets derived from normal individuals with a maternal history of Alzheimer's had lower cytochrome c oxidase (=MT-CO1. see below) activity.

For S1 and S9 there were altogether 4 measurement points for gene expression, and only 3 repeats for each measurement. Results are presented in Table 6 below; changes of gene expressions compared to the control from peripheral leukocytes are presented. The Gene Expression analyses was conducted using TracTechnology by PlexPress Ltd in Helsinki. The TRAC data presented in Table 6 has been generated according to process instructions with quality tested instruments and reagents. PlexPress Quality Management System is set up according to the ISO 9001 standard. P-values are from t-distribution of a one sided test of deviation from control average, and are presented only when below 10%.

TABLE 6

Results from gene expression study for S1 and S9 (combined data)
S1 and S9, Combined Data

| Gene | 12 hour + 0 h test | | 12 hour + 1 h test | | 4.5 day + 0 h test | | 4.5 day + 1 h test | |
|---|---|---|---|---|---|---|---|---|
| | Change % | P-value | Change % | P-value | Change % | P-value | Change % | P-value |
| HO-1 | −31% | 4.0% | −54% | 4.7% | 82% | 0.1% | 110% | 0.4% |
| CYP1A2 | 100% | 5.0% | n.m. | | 62% | 0.3% | 14% | |
| CYP3A4 | −17% | | −45% | | 67% | 1.1% | 69% | |
| CYP2C9 | 8% | | 18% | | 0% | | 46% | |
| CYP2B6 | −14% | | 8% | | 73% | 0.3% | 147% | 0.1% |

TABLE 6-continued

Results from gene expression study for S1 and S9 (combined data)
S1 and S9, Combined Data

| Gene | 12 hour + 0 h test Change % | P-value | 12 hour + 1 h test Change % | P-value | 4.5 day + 0 h test Change % | P-value | 4.5 day + 1 h test Change % | P-value |
|---|---|---|---|---|---|---|---|---|
| PGC-1a | −3% | | −21% | | 102% | 0.4% | 30% | |
| MT-CO1 | −10% | 3.3% | 4% | | 24% | 0.6% | 23% | 1% |
| GPD2 | 24% | 1.4% | 23% | 3.2% | 31% | 0.2% | 0% | |
| MT-CYB | −2% | | 2% | | 22% | 0.5% | 21% | 1% |
| G6PD | 3% | | 18% | 0.1% | 9% | 4.1% | −13% | |
| GRHPR | −26% | 0.5% | 6% | | 70% | 0.4% | 100% | 0.1% |
| AOX1 | −6% | 9.4% | 8% | 3.2% | n.a. | n.a. | n.a. | n.a. | n.m. = data missing or not meaningful, n.a. = measurements not available (not conducted), P-values < 0.10 are presented in the table CYP1A2 is statistically significantly up regulated in 12 h and also after 4.5 days before glucose intake, i.e. in fasting diet compared to control. CYP3A4 and CYP2B6 are clearly up regulated after 4.5 days in fasting condition and also after glucose intake. Inducers of the latter genes/enzymes are used as anticonvulsants and mood stabilizers, thus the CYP3A4 and CYP2B6 data indicates potential therapeutic effect for the DGAcs (see indication areas). CYP3A4 was statistically significantly up regulated also for S10. Statistically significantly up regulated CYPs are located in the ER indicating increased ER activity from the use of the DGAcs.

Next important observation from Table 6 is the sharp increase in HO-1 expression after 4.5 day administration. The increases in both fasting condition (0 h) and 1 hour after glucose intake (1 h) were both statistically very significant. Furthermore Similar statistically very significant 160% increase in HO-1 was observed also for S10 in statin group. (S10 was the test subject with halved dose of Simvastatin.) Earlier presented results in Table 5 of increased blood bilirubin levels confirm that the increased HO-1 gene expression has lead also to increased enzyme activity. (This is just the opposite as in Table 3 administration.)

Importantly HO-1 gene expression was clearly down regulated in the short test of 12 hours/2 doses of DGAcs. This same phenomenon happened in 4 day test earlier, as indicated clearly by the decrease in blood bilirubin levels in Table 3 (and also in Table 4).

Interpretation: One can conclude that HO-1 expression is not highly activated immediately after starting the use of the DGAcs or in fact that its expression was even down regulated. The same down regulation seems to be the case when there is longer time from the administration even in high dose case Table 3) and also in the case of lower once a day dose (Table 4). At the same time immediate dose response for DGAcs can clearly increase HO-1 expression very significantly. Interpretation of these apparently but not in reality conflicting results: HO-1 is activated by the use of DGAcs de facto always but only temporarily. Oxidative stress induced by the increase in aerobic ATP production (OXPHOS) can also be efficiently ameliorated due to up regulation of Nrf2/ARE genes; both are due to the use of DGAcs (see FIG. 2).

Therapeutic strategy for the DGAcs administration with HO-1/Nrf2/ARE genes: extremely many diseases (see therapeutic areas) can be ameliorated by controlled up and down regulation of HO-1 and other Nrf2/ARE genes. With right dosing the DGAcs can be used for diseases that need e.g. activated inducible heme oxygenase (HO-1) system or other Nrf2/ARE enzymes. The DGAcs can work like a vaccine that activates (sometime permanently) the immune system against certain diseases, i.e. the use of the DGAcs can keep HO-1 and other Nrf2/ARE genes in active state by daily temporary stimulation. In case of a successful mild daily stimulation, Nrf2/ARE genes are down regulated for most of the time and also ROS levels are lowered. For some disease states high doses temporarily might be needed in order to stop harmful (e.g. inflammatory) processes by strong activation of Nrf2/ARE response. Simultaneous increase in aerobic energy metabolism and pyruvate production enhance therapeutic effect significantly.

G6PD and AOX-1 (aldehyde oxidase) genes belong also to Nrf2 genes that often use NADPH-enzymes as co-substrates in reactions (see FIG. 4). NADPH is also the favorite co-substrate for GRHPR gene and thus it probably can be classified as an Nrf2 gene. Thus we could conclude that 3-4 Nrf2 genes are up regulated by the DGAcs. (Unfortunately AOX1 was not yet included in the 4.5 day panel for S1 and S9. In the case of S10 in 4.5 day panel that was conducted later, AOX1 gene expression was increased by 56% with P-value=0.1%)

Important additional support to the notion that the DGAcs can stimulate endogenous antioxidant defenses (Nrf2/ARE) comes from consistently and statistically significantly declining ROS levels in human hepatocytes experiments (see Examples 1.1-1.6).

Interestingly GRHPR enzyme is first slightly down regulated even statistically significantly and up regulated strongly only after 4.5 day administration. Both are consistent observations. For the use of DGA the clear activation of GRHPR and its repeatable DGA-HPA loop and dimension towards peroxisomes is important.

Genes related to enhanced aerobic energy metabolism: GPD2, MT-CO1 (NRF1), and MT-CYB relate directly to electron transport chain that derives energy from NADH molecules (see definitions from FIG. 3b). PGC-1a is a SIRT1 dependent master regulator of energy metabolism, e.g. of mitochondria biogenesis, and related multiple tasks. (PGC-1a is activated or deactivated also via multiple other ways than NAD+ dependent deacetylation by SIRT1.)

As can be seen from Table 6 MT-CO1 and MT-CYB are clearly and statistically very significantly up regulated after 4.5 day use of the DGAcs. Importantly increased coding of MT-CO1, mitochondrially encoded cytochrome c oxidase I, can be directly link to NRF1, which is nuclear respiratory factor 1. NRF1 functions e.g. as a transcription factor, that activates the expression of some key metabolic genes regulating cellular growth and nuclear genes required for mitochondrial respiration. Also PGC-1a is up regulated by over 100% and statistically significantly in 4.5 day in fasting conditions. Its expression is increased by 30% also 1 h after glucose intake, but due to poor data quality in some observations this increase is not statistically significant. Furthermore mitochondrial glycerol phosphate dehydrogenase (GPD2) is up regulated already in 12 h and continues to be that also in fasting conditions after 4.5 day administration.

Gene expression data points very clearly to the direction that the DGAcs can activate aerobic metabolism and mitochondrial biogenesis. Many of the up regulated genes (also CYPs) encode heme proteins containing iron (Fe). This is nicely in line with decrease of free Fe in blood sample (see Examples 2.1, 2.2 and 2.3.1). Additionally in rat experiments mitochondrial up regulation by increased calcium release was observed (Example 2.2). The data as a whole, point clearly to the direction that the DGAcs can reduce mitochondrial dysfunction by activating biogenesis of new properly functioning mitochondria. Thus we postulate that the DGAcs can prevent diabetes, neurodegenerative diseases, atherosclerosis and cancer by decreasing mitochondrial dysfunction. One example: according to literature decreased MT-CO1 activity in leukocytes has been associated to increased risk in developing Alzheimer's disease.

Immediate response of the use of the DGAcs seems to be the activation of mitochondrial glycerol phosphate shuttle gene (GPD2). This phenomenon may be useful in fast exercise performance and recovery from exercise (Example 6). GPD2 can temporarily generate ATP energy much faster from NADH than traditional Malate-Aspartate-shuttle. Also acidosis and lactate production is decreased.

Example 2.3.3

Plasma Sample Analyses on PYR, ALA, LAC and NO

As mentioned above also plasma samples were collected from S1 and S9, at 0 h and 1 h both in 12 h and 4.5 day test, i.e. 16 observations were gathered with either DGAcs or zero control situations. Additionally in statin group (S10 and S11) 2×2 measurements were done. Altogether there were 20 observations and, thus 10 differences between control and DGAcs administration can be calculated. Pyruvate concentrations were measured using Pyruvate Assay Kit from Sigma (MAK071 Sigma). Alanine concentrations were measured using Sigma Alanine Assay Kit (MAK001). Lactate concentrations were measured using Sigma Lactate Assay Kit (MAK064). And finally nitric oxide (NO) concentrations were measured using OxiSelect™ In Vitro Nitric Oxide (Nitrite/Nitrate) Assay Kit from Nordic Biosite Oy.

TABLE 7.1

Deviation in Plasma Pyruvate, Alanine and Lactate Concentrations from Zero Control

| Measurement | Change in Pyruvate | Change in Alanine | Change in Lactate | Correlation between the levels of plasma PYR & ALA | PYR & LAC |
|---|---|---|---|---|---|
| 1 | 13% | 1% | −30% | | |
| 2 | 59% | 5% | −63% | | |
| 3 | 23% | 4% | n.a. | | |
| 4 | 39% | 21% | −48% | | |
| 5 | 35% | 33% | −75% | | |
| 6 | −22% | −8% | −28% | | |
| 7 | 32% | −21% | −70% | | |
| 8 | 32% | 3% | 46% | | |
| 9 (S11) | 11% | 3% | −1% | | |
| 10 (S10) | 38% | −6% | −18% | | |
| Average Change of the Concentration | 25.9% | 3.5% | −31.9% | | |
| P-value compared to the control | 0.22%**) | 24.0% | 1.8%*) | +0.827**) | −0.794**) |

*)P-value <0.05,
**)P-value <0.01

As can be seen from Table 7.1 plasma pyruvate amount increases on average by 25.9% compared to control measurement. This increase happened in all tested, i.e. also in statin group, and is statistically very significant. In healthy volunteer group only, i.e. S1 and S9, the increase was also approximately 25%, but more importantly it remained roughly at 20% also 1 hour after administering 75 000 mg of glucose. The DGAcs administration increases intracellular pyruvate production both in fasting conditions and also after glucose administration. This indicates that the pyruvate comes from multiple sources like presented in FIGS. 1b, 3a and 3b. Lactate seems to be clearly one very natural source seen from the results.

Plasma lactate amount decreases on average by 31.9% compared to control measurement. This increase happened in all tested, i.e. also in statin group, and is statistically very significant. In healthy volunteer group only, i.e. S1 and S9, the decrease was even bigger some 38%. As expected the correlation between the levels of plasma pyruvate and lactate was negative and roughly −80%. In the plasma there is roughly ten times more of lactate than pyruvate. Almost perfectly in line with that the multiple in regression analyses was −012 when the level of observed pyruvate in plasma was explained by observed level of lactate. Furthermore these results seem to be also very well in line with so called lactate cycle in which lactate is transported to the liver in fasting state from gluconeogenesis. In fasting situation the lactate transport was on average 84% higher compared to situation after 75 000 mg glucose intake, and the difference was statistically significant (P=1.1%).

Extra cellular pyruvate is extremely good source of aerobic energy for active cells and tissues containing multiple mitochondria, e.g. neurons, inner organs, and aerobic muscle cells. Pyruvate is also a very suitable intracellular (starting) building block in anabolic reactions, see FIG. 3a. Plasma Alanine levels did not change compared to control. This is also interesting because normally alanine increases as a consequence of increased pyruvate. Possibly peroxisomal transaminase reactions from HPA and ALA into PYR and L-Serine (FIG. 1b) counteract the increase in ALA (and aKG) from PYR (and glutamate).

Decrease in lactate cycle is very good because it e.g. is a clear indication that cells are able to use bigger part of the nutrition that they are provided themselves. Very significant decrease in blood lactate compared to control is also a clear indication that mitochondrial $NAD^+$ providing shuttles work better in the DGAcs group. We also see this very strong result as a sign that likely RBCs have increased their lactate intake somewhat. Ntf2/ARE mechanism and DGA-HPA-loop can work also in RBCs, even without mitochondria, and thus the DGAcs can enhance metabolism even in the RBCs.

There is also a surprising additional follow up on increased blood pyruvate concentrations: a decline in blood urea (like seen in Examples 2.1 and 2.3.1). An increase in pyruvate increases the flux of TCA e.g. in renal cortex mitochondria. In literature it has been shown and it is also theoretically obvious that pyruvate increase in turn increases aKG concentration in the matrix and decreases intramitochondrial $NAD^+/NADH$-ratio. Both processes decrease the activity of glutamate dehydrogenase (GLDH) activity. As is well known, GLDH reaction provides majority of amino groups ($NH_3$) into the urea cycle. I.e. on top of activation of mitochondria and aerobic metabolism, the use of DGAcs can also save amino groups for protein synthesis e.g. in muscles. Additional note: pyruvate increases and intramitochondrial $NAD^+/NADH$-ratio declines also due to increased beta oxidation induced by the DGAcs. The follow up is the same but causes slightly different. In both cases ATP production capacity for e.g. anabolic reactions is enhanced.

Related to the decrease in urea cycle the NO level decrease among healthy volunteers whose BMI<25 (see Table 7.2). In the literature this phenomenon is well known. Decrease in urea cycle decreases amount of L-arginine. NO is synthesized from the reaction from L-arginine to cirtulline.

TABLE 7.2

Deviation in Plasma Nitric Oxide Concentrations from Zero Control

| Measurement | Change in Nitric Oxide | Change in Nitric Oxide (BMI <25) | |
|---|---|---|---|
| 1 | −8% | −8% | |
| 2 | −9% | −9% | |
| 3 | −32% | −32% | |
| 4 | −25% | −25% | |
| 5 | −10% | −10% | |
| 6 | −1% | −1% | |
| 7 | −19% | −19% | |
| 8 | +8% | +8% | |
| 9 (S11) | +22%*) | — | |
| 10 (S10) | −25% | −25% | |
| Average Change of the Concentration | −9.9% | −13.4% | Changes in NO are in line with seen decline in urea cycle. Possible clear deviation in BMI >>25 group in NO vs. urea can be observed but needs more studies. |
| P-value compared to the control | 4.25%*) | 0.63%**) | |

*)P-value <0.05,
**)P-value <0.01

It is very interesting and also consistent to notice that observed decline in NO (approximately 10%) is roughly the same as average decline in blood urea after 4 and 4.5 day administrations (approximately 9%).

Even more interesting is the observation that in S11, belonging to high statin group and BMI>>25 (measurement 9), NO production was increased. All plasma samples were divided into 4 wells to get more accurate average readings. We can use these 4 independent measurements (from the same sample) to test that is the deviation in NO of S11 statistically significant. The increase of NO from control turns out to be statistically significant (P=1.4%).

Example 2.3.4

Glucose Tolerance Test, Plasma Glucose and Insulin Compared to Zero Control

In the 4.5 day experiment also standard, fasting glucose tolerance test was conducted for S1 and S9 starting after 2.5 hours of last administration of DGAcs. Blood glucose levels were measured at 0 h, 60 min and 120 minutes.

In all 120 minutes measurements (with S1 and S9, altogether 4 comparisons) blood glucose was lower compared 0 h level in DGAcs groups. For S9, who had slightly elevated fasting blood glucose level of 6.0 mmol/L the drop in glucose level was more significant, i.e. some 0.6 mmol/L lower at 120 min compared to the control. For S1 the drop was seen but marginal, probably due to relatively low starting level of 5.0 mmol/L. Blood insulin levels were measured at 60 min. For S9 higher insulin level with the DGAcs was seen at 60 minutes, and that likely lead blood glucose rapidly down from elevated levels. For S1 blood glucose levels did not rise significantly at 60 minutes, and thus insulin levels at 60 minutes did not show any pattern.

All in all the DGAcs seems to have a positive decreasing effect on blood glucose level after 75 grams glucose intake. This is likely mostly due to increased ATP production capacity of the cells that facilitates glucose intake and conversion into glycogen, and G6P to be used in pentose phosphate pathway and glycolysis (see FIG. 3b). Also insulin production by pancreatic beta cells (that uses e.g. GP-shuttles in their energy production) probably rise, and that also enhances the process towards faster glucose homeostasis in blood stream.

Example 3

NMDA-Induced Excitotoxity in Rat Cortical Neurons

Two separate studies were conducted. First study conducted with University CRO and second confirmatory study with Private CRO.

Cell culture. Cortical neurons were dissected from P1 rats and cultured in 96-well plates up to 7 days in the medium containing: neurobasal medium, 1.5% B27 supplement, 1 mM L-glutamine, penicillin/streptomycin.

Treatment of cells with DGAcs was done in two different ways. In all studies the total cultivation time was 7 days (7th day in vitro=7 DIV). In the first study a clear element of calorie restriction (CR) was built in to the standard model provided by the CRO. The other 24 hour pretreatment was without CR (more info in examples 2.1 and 2.2 below). Separately also exceptionally high doses of DGAcs were administered to neurons. No toxicity was observed even with 40-200 times the effective treatment dose of DGAcs. (Effective dose was 10-50 µg/m).

Cell viability/cytotoxicity. Cell viability was detected by LDH tests like in examples 1.1-1.2.

Fluorescent imaging. Imaging experiments were performed at 7 DIV. The cells were loaded with fluorescent dyes (fura4F, fura-ff and rhodamine 123,) in cell culture medium at 37° C. 1h, 5 µM for each dye. Then cells were washed with $Mg^{2+}$-free Locke's buffer containing 1.3 mM $Ca^{2+}$, moved to the microscope stage, and imaging was performed at room temperature. For NMDA-induced $Ca^{2+}$-peak measurement a higher affinity $Ca^{2+}$-indicator Fura4F (Kd 0.77

μM) was used. For delayed calcium deregulation experiments a lower affinity $Ca^{2+}$-indicator FuraFF (Kd 5.5 μM) was used to avoid a saturation of the signal.

Example 3.1

Protection Against NMDA-Induced Excitotoxity

Cell treatment: concentration of DGAcs (10, 50 and 100 μg/ml) was added into cell culture medium at 4 DIV. After 24h (at 5 DIV) 25% of medium was changed to fresh containing 1.5× concentration of DGAcs. Same treatment (change 25% with 1.5× concentration) was repeated at 6 DIV. The cells were transferred into $Mg^{2+}$-free Locke's buffer containing the same concentrations of DGAcs immediately before imaging experiments (at 7 DIV). For controls the same amount of medium was changed without addition of DGAcs.

Measurement of LDH Viability, Effect of Calorie Restriction (CR)

Cell treatment according to the protocol renewed only 25% of the medium during 5 DIV and 6 DIV, meaning that neurons received only very small amounts of new nutrition, i.e. experienced calorie restrictions (CR). Again CR caused dose dependent viability loss DGAcs groups, this time in neurons (see FIG. 13). This same phenomenon of increased cell death in CR was already seen with human hepatocytes in previous examples. Likely explanation is the same: DGAcs administration increases metabolic activity in neurons and/or their (aerobic) ATP production and consumption, which leads to enhanced cell cycle control and programmed cell death (apoptosis) in nutritional scarcity. As can be seen from FIG. 13, this effect is very small but on the other hand consistently dose dependent and statistically significant. Viability loss compared to zero control was highest and statistically significant in 10 μg/ml group but also all other groups experienced loss of viability.

Measurement of LDH Viability, Protection Against Excitotoxity Induced by NMDA Stimulation In analyzing the results from the test set up starting at 7 DIV with 1 h NMDA stimulation (and 23 h follow up period), separate viability loss caused by CR can be taken into account by indexing 25 μM NMDA and 50 μM NMDA groups with the results of 0 NMDA control (see FIG. 14a). As can be seen from the figure, DGAcs treatment induces very clear and significant protection against NMDA-induced excitotoxity in both 25 μM NMDA and 50 μM NMDA group. Even without correction for CR induced viability loss, DGAcs treatment induces very clear protection against NMDA-induced excitotoxity in 50 μM NMDA group (see FIG. 14b: "Viability after 24 hours with 1 h NMDA stimulation, indexed to 0 NMDA")

In literature it is described that excitotoxity may be involved in spinal cord injury, stroke, traumatic brain injury, hearing loss (through noise overexposure or ototoxicity) and in neurodegenerative diseases of the central nervous system (CNS) such as multiple sclerosis, Alzheimer's disease, amyotrophic lateral sclerosis (ALS), Parkinson's disease, and also Huntington's disease. The use of DGA can effectively protect neurons against excitotoxic injury and thus likely also to prevent the onset of and/or alleviate mentioned diseases related to it.

Study set up in example 2.1 with primary rat cortical neurons was repeated with Private CRO in two similar experiments. In the first confirmatory study the viability loss due to CR was confirmed statistically significantly at 6 DIV. This demonstrates that DGAcs causes loss of viability when calories are restricted in vitro, and this effect must be taken into account in the model. As already explained above, observed small loss of viability is likely due to two factors:

1) increased aerobic ATP production (PGC-1a/NRF1) and related increase in energy and nutrition consuming anabolic, and anaplerotic reactions, and 2) enhanced cell cycle control (e.g. Nrf2/ARE).

Despite the success in repeating energy metabolic part of this experiment with neurons, the NMDA protection part was not as successful. Results from excitotoxity repetition by the private CRO were in line with above results but they were not statistically significant. The instability of the results may be due to the fact that e.g. Nrf2/ARE activating mechanisms are mostly missing from neurons. Nrf2-mediated neuroprotection is primarily conferred by astrocytes both in vitro and in vivo. Neuronal cultures would need astrocytes and other glial cells for full protection by the use of DGA. i.e. important Nrf2 activation by the use of DGA cannot be at full play in neuronal cell culture. In pure neuronal cell culture model provided by the CROs with minimum amount of glial cells only the enhancement of mitochondrial energy metabolism by the use of DGA can functions at full strength. Worth noticing is that the increase in energy metabolism gives also alone protection against excitotoxic insult like indicated also by the next Example 2.2.

Example 3.2

Mitochondrial $Ca^{2+}$-Uptake in Rat Cortical Neurons

In this study azero control and one DGAcs group of primary rat cortical neurons was cultivated normally without DGAcs until 6 DIV, and then the DGAcs group was treated with 50 μg/ml DGAcs for 24 hours. After that culture medium was replaced by $Mg^{2+}$-free Locke's buffer containing 50 μg/ml DGAcs and imaging experiments were performed at room temperature at 7 DIV.

50 μM NMDA in the presence of 10 μM glycin in $Mg^{2+}$-free buffer was used to stimulate the cells. For NMDA-induced $Ca^{2+}$-peak a higher affinity $Ca^{2+}$ indicator Fura4F (Kd=0.77 μM) was used.

For complete mitochondrial depolarization and release of $Ca^{2+}$ accumulated in mitochondria 2 μM protonophore FCCP was used in the presence of NMDA-receptors inhibitor MK801 (2 μM). Results of calcium release for zero control and DGAcs group in various treatments are presented in Table 8.

TABLE 8

Results from Study testing Calcium uptake by Mitochondria of Primary Rat Cortical Neurons

| | baseline Ca | peak NMDA | FCCP |
|---|---|---|---|
| Zero Control | | | |
| Average Ca release | 0.073 | 0.213 | 0.402 |
| N | 5 | 5 | 5 |
| Standard error of the mean (SEM) | 0.00198 | 0.0127 | 0.0295 |
| 50 ug/ml DGAcs for 24 h: | | | |
| Average Ca release | 0.070 | 0.219 | 0.475 *) |
| N | 3 | 3 | 3 |
| Standard error of the mean (SEM) | 0.00346 | 0.00395 | 0.00667 |

*) Statistically significant deviation from the control (p = 3.4%)

As seen from complete mitochondrial depolarization treatment (FCCP) in table 8, calcium uptake by the mitochondria is increased by 24 hour of DGAcs administration. It indicates that the activity of mitochondria and/or their mass has increased, e.g. due to mitochondrial biogenesis. This result is in line with similar activity increase in gene expression experienced in peripheral leukocytes after DGAcs treatment in humans in vivo (see Example 2.3.2).

Clear enhancement of energy metabolism of CNS tissues is also in line with indirect results from clinical in vivo experiments, e.g. head ache and other withdrawal symptoms after stopping administration (see Example 2.1 and 2.2).

Example 4

Weight Loss and Change in the Body Composition, a 3 Week in vivo Study on Rats

In this in vivo experiment 45 rats (24 males and 21 females) were tested in Finnish National Institute of Health. Used DGAcs doses were high compared to human trials ranging between 100-1000 mg/kg/day, but on the other hand the metabolism of rats is much faster than in humans and thus the effective doses for rats can be clearly higher than for humans. In some experiments even 20-50 times higher compared to humans in vivo have been reported in literature. Thus this experiment can give indication also for human use. The animals were kept under controlled conditions, with the temperature set from 20° C. to 21° C., the humidity at 47.6%, and a 12-hour light-dark cycle (lights on at 6:00 am). In this ad libitum feeding study the DGAcs was mixed in the diet for the whole experimental period (3 weeks). The animals were divided into 4 groups, which received 0 (zero control), 2, 10, and 20 g glycerate per kilogram of diet. The average DGAcs consumption was 0.1, 0.5, and 1.0 g/kg per day, respectively, as calculated based on weekly food consumption. The animals experimented were 3 to 5 months old AA rats. The animals were given water and a standard laboratory feed (SDS RM1) ad libitum for 3 weeks. In the experiment the development of weights of rats receiving DGAcs, and the control were measured, as well as the food consumption during the experiment and change in the body weight. Males and females were separated resulting altogether to 8 groups with 5-6 animals in each.

In male groups combined, the average daily food intake was roughly 50 g/kg/day, i.e. 5% of the total body weight (bwt). In female groups it was slightly higher some 56 g/kg/day. As a cumulative sum the rats ate roughly their own bwt of feed during the 21 day test period.

Both in male and female groups the food intake was higher in DGAcs groups compared to the control, 3.7% in males and 2.5% in females. Interestingly in male DGAcs groups combined this increase in food consumption was even statistically significantly different from the control group. This is very remarkable because at the same time the average body weight in male rats decreased 4 grams or 1.1% of bwt compared to the control. Further to stress the point, also in females food intake was elevated by 2.5% and the average weight remained practically stable, increasing only 0.6 grams or +0.2% compared to control. (In female DGAcs groups there was clearly more deviations in the first week after starting the test, and that is one reason why the increase in food intake was not statistically significant.)

Otherwise everything in this experiment has been equal between different groups. Daily energy consumption into physical activities was similar in groups and there were no running wheels or any other equipment that could cause significant differences in the amount of daily exercise. The temperatures were kept stable and at neutral levels, and circadian rhythm was stable. Thus it is unlikely that differences in exercise or thermogenesis could explain observed clear increase in food consumption and simultaneous average drop in bwt in DGAcs groups.

Moderate, but statistically significant, 2.5-4% increase in food intake paradoxically leads to a decrease in weight (or stable weight in the case of female rats) in DGAcs groups. Energy consumption has to be increased by the use of DGA. This phenomenon was observed already in cell culture experiment with human hepatocytes and rat cortical neurons. Now this odd phenomenon of increased energy consumption has been demonstrated also in vivo in rats. The amount of unexplained energy consumption is roughly 5% in males. Furthermore in section "ATP production per gram of nutrition and change in body composition" we concluded that, ATP energy production per gram of nutrition increases by the use of DGA. This means that unexplained energy consumption is even wider in this in vivo experiment, maybe even 5-9%.

The use of produced extra ATP energy is very likely to anabolic reactions, e.g. gluco-/glyceroneogenesis and protein synthesis that consume a lot of energy (see FIGS. 3a and 3b, and starving diet and CR in example 1 and Example 3.1). Energy is consumed also to increased control and correction of anabolic processes in the ER, e.g. ATP-dependent chaperones. Increased supply of substrates, pyruvate and amino groups, for anabolic reactions by the use of DGA (shown in example 2.1-2.3) supports also the idea that excess ATP is consumed for enhanced renovation of proteins (enzymes) and similar complex macromolecules. In general these processes increase ATP consumption and they are beneficial to cells and promote long term health.

From the above and Examples 5 and 2 follows the next important finding: by increasing ATP production and beta oxidation of fatty acids (FA), the use of DGA can have an effect on body composition of humans and also on animals, like livestock, poultry and fish. Energy stored in fats is indirectly converted into protein and thus increasing the muscle content of the body in the expense of fat.

Example 5

Enhancement of Mitochondrial Beta Oxidation in Longer Term, in vivo in Rats

From the above experiment altogether 12 rats were chosen from 0.1 g/kg/day DGAcs group (N=6) and zero control (N=6) for a measurement of free glycerol from liver samples. Liver samples contained also blood entering the liver from other tissues, thus on top of hepatic tissues the samples reflect also the metabolic situation in other tissues of the body than just the liver.

In this experiment nutrition intake, except of course for DGAcs, was controlled to be exactly the same during the experimental day, and three day before the experiment. For AA rats, that are used to alcohol but didn't receive any alcohol in 3 day before the experiment, catabolic redoxactivity in the cytosol was controlled by giving rats ethanol (equaling 1.2 per mille blood alcohol concentration, which represents only mild alcohol intoxication to the AA rats). The rate of ethanol oxidation remained the same in all groups. The maximum increase was only some 3.6% acceleration compared to control, i.e. in practice the same, and naturally this deviation was not statistically significant.

Experimental session started at 8:00 to 9:00 am. To diminish possible pain during the experiments, all animals were injected subcutaneously with buprenorphine (0.01 mg/kg) a few minutes before the blood samples. During the experimental session no difference in other metabolic activity, e.g. rate of ethanol oxidation, between the control and treatment group was detected from blood samples. Immediately after the last blood sample, the animals were anesthetized with pentobarbital (40 mg/kg IP, 1% [wt/vol] in saline). Thereafter (5-10 minutes), liver pieces were quickly (within 2-4 seconds) excised and freeze-clamped. Liver samples were stored at _718 C. until glycerol determination. For the liver free glycerol measurements, the freeze clamped livers were thoroughly homogenized and diluted 1:6 with mQ water, assuming the liver tissue density of 1 g/mL. The homogenates were incubated in a boiling water bath for 5 minutes and centrifuged at 14000 rpm for 15 minutes. The resulting supernatants were used for free glycerol measurement with an enzymatic end point commercial assay kit (Boehringer-Mannheim, R-Biopharm, Darmstadt, Germany) according to the manufacturer's protocol except that the assays were modified for use with small volumes of supernatant using a 96-well microplate reader (Labsystems Multiskan RS, Helsinki, Finland). Samples were assayed in duplicate.

TABLE 9

Effect of DGAcs on hepatic free glycerol levels, including also extracellular matrix

| Treatment | Free glycerol concentration |
| --- | --- |
| Control (no DGAcs) | 3.06 +/− 0.55 (6) |
| DGAcs (0.1 g/kg per day) | 4.88 +/− 1.21 (6)* |

*P < 0.05 compared with the control group
Glycerol levels are expressed as micromoles per gram wet weight tissue In 0.1 g/kg DGAcs group glycerol levels were increased by 59% compared to the control. This result is very remarkable. The observed increase in the concentration of free glycerol compared to the control samples was roughly 0.17 g/kg, i.e. even clearly bigger than the average daily dose in DGAcs group.

It should be noted that in this experiment there was no acute administration of DGA before the experiment, and there is no reason to expect that DGA would accumulate in the liver during the 3 week experiment, because the liver is very efficient in all metabolisms (especially towards glycolysis and gluco-/glyceroneogenesis via GLYCTK1 or GLYCTK2 enzymes, FIG. 1b). Also the fact that ethanol oxidation didn't change compared to the control clearly indicates that the amount of DGA in the liver was approximately the same as in control group at the start of the experiment, i.e. very small in both.

Furthermore from other conducted experiments (see Example 2) we know that DGA seems to be evenly distributed into various tissues after administration in vivo. Also in all other tissues DGA should be relatively easily metabolized. Thus also in other tissues the concentration of DGA, at the onset of this non-acute dose experiment has been clearly less than 0.1 g/kg, maybe at maximum some 0.01 g/kg. This means that direct or indirect acute conversion of DGA to free glycerol cannot explain the result in Table 9, not even any significant part of the result.

First and probably the main source of the difference in free glycerol in this experiment is from triglyceride lipase activity that liberates fatty acids from trigys for mitochondrial beta oxidation in the liver. In the liver it is also possible that free glycerol arises from D-glyceraldehyde (D-GALD) with alcohol oxidation, but that happens in the same amounts in both groups and thus cannot explain observed difference in free glycerol. Additionally there can't be any tendency for building of large quantities of D-GALD molecules into the liver by 3 week DGA treatment that could explain large difference in free glycerate observed in this study. (Liver manages most of fructose metabolism in the body and it produces D-GALD. The natural metabolic direction for D-GALD is towards glycolysis by triokinase enzyme (see FIG. 1b).)

Supporting the increase in beta oxidation as a source of the huge difference in free glycerol is the fact that in muscle tissues only the FAs of circulating trigys are taken in to the myocytes and the free glycerol part is liberated to the blood circulation to be taken back to the liver. Thus increased beta oxidation in muscle cells is also very much in line with glycerol increase in the liver sample in the DGA group.

Ruling out other possible sources for the difference in free glycerol: Glycerol kinase catalyzes the reaction from free glycerol+ATP to G-P-3+ADP (see FIG. 1b). This enzyme works also to the other reaction direction, but in practice ADP has been found very unappealing substrate for this kinase enzyme. Thus observed huge difference in free glycerol cannot be directly from increased G-3-P formation from glyceroneogenesis in DGA group. DGA does not easily convert towards D-GALD because aldehyde dehydrogenase (ALDH) enzymes favor clearly the opposite direction (FIG. 1b) and in any case are ALDHs are often located and active mainly in the mitochondrial matrix. AOX1 enzyme (see Example 2.3) could be a possible enzyme for mentioned reaction (direction) but it is very unlikely that it could facilitate the volumes needed for extraordinarily high 59% increase in free glycerol. (Furthermore in conducted one hepatocyte study the expression of AOX1 did not increase like it did with leukocytes.) All in all the acute conversion towards D-GALD and thereafter towards glycerol can represent only a very minor part of the total even in "highest" cases. Thus DGAcs administration does not directly cause the observed increase in glycerol via that route. Second favorite direction for DGA is towards HPA. According to gene expression analyses this direction is activated at least in the longer term (see Example 2.3). This direction does not provide glycerol. Finally very likely the long 3 week DGA administration with the food has increased the rate of glyceroneogenesis compared to the control (independently of an increase in aerobic metabolism). That of course can indirectly increase the amount of free glycerol in the hepatic tissues through an increase in beta oxidation and required lipase reactions that liberate free glycerol inside the liver and in other tissues (to be transported back to the liver). Increase in this pathway is in fact something that we want to prove here.

Because the difference in free glycerol in this non-acute dose study is so huge 59%, it is very likely due to a more structural increase in mitochondrial beta oxidation. We postulate that 3 week administration of the DGA has increased the use of FAs as a source of energy and thus mitochondrial beta oxidation has increased in the liver and other aerobic tissues. Increase in beta oxidation is supported also e.g. by increases in blood trigys levels in clinical Examples 2.1, 2.2, and 2.3 in DGA groups compared to zero controls.

We can now summarize that the use of the DGA increases metabolic use of fats for mitochondrial beta oxidation. Fatty acid oxidation yields a lot of ATP energy for ATP consuming activities e.g. cell cycle control and protein synthesis. In experiment 2 we have shown that amino acid removal from the body is decreased by the use of DGA. In Example 2.3.3 we show that lactate cycling from the cells to the liver is also decreased. In Example 4 we noticed some 2-5% imbalance in unexplained energy supply vs. consumption. This imbalance grows even higher, even to some 5-9%, when we can now assume that ATP generation per gram of nutrition is likely enhanced by e.g. the increase in aerobic energy production (beta oxidation and decreased lactate cycling) by the use of the DGA.

Higher energy level without increase in body weight is the best possible outcome that any pharmaceutical and/or health promoting substance can yield. The extra energy produced (supply) is used in 1) protein syntheses and other anabolic and anaplerotic reactions, and 2) in enhanced metabolic and cell cycle control. Energy stored in fat is in small but meaningful scale converted into muscle tissue. Total body weight can decrease without losing muscle mass.

Example 6

Effect on Physical Performance and Recovery

Acidosis produces lactate that is an indication of restrain to fast ATP production. As seen in Example 2.3.3 the use of DGAcs can reduce plasma lactate levels on average by 30 percent. This very strong result has been obtained in non-exercise state but nevertheless it shows that the use of DGAcs can prevent acidosis formation by reducing lactate amount in blood.

Two healthy male volunteers S1 and S3 from Example 2.1 participated in 400 m running experiment with 4 day administration of DGAcs and without it. The experiments were done at 2-3 pm in the afternoon. In DGA experiment additional dose of DGAcs (5 mg/kg) was taken before lunch at 11 am, and lunch was eaten at 12 am. Both volunteers possessed good physical condition but were not trained in 400 meter running. The length of the 400 m exercise at full speed was too much especially for S1. For S3 no significant differences between control and DGA times were observed. Nevertheless, in qualitative terms, both S1 and S3 were much more ready to resume other physical exercise with the DGA than without it. This difference was striking especially for S3 and can be as a result in decreased acidosis.

Additionally based on results from practical other Examples 1-5 it is obvious, that DGA can enhance energy metabolism and energy production thus contributing also to enhancing physical training, performance and recovery from exercise.

TABLE 4

Non-exhaustive summary table of the results from first set of clinical studies, i.e. with non-acute dose/Examples 2.1 and 2.2

| No. | Test | Results |
|---|---|---|
| 1 | fS-Alat | All study subjects had fS-Alat levels in the recommended range. Tendency for improvement was observed, when values were higher in the range. (S3 is an exception due to extremely hard physical training session before 4 day treatment.) N = 8. |
| 2 | fS-Asat | On average 15-20% reduction in values. N = 6. |
| 3 | Bilirubin | On average some 20% reduction in values. N = 6. |
| 4 | Bilirubin conj. | On average 20% reduction in values. N = 6 |
| 5 | CK, creatinine kinase | On average 25% reduction in values (N = 4). Lower also for subjects S5 and S6. |
| 6 | fS-Fe | On average 15% reduction in values. N = 6 |
| 7 | fS-Glucose | Down or unchanged (=change less than 2%) for all healthy volunteers (N = 8) in all periods and doses; average decline only some 6%. |
| 8 | fS-Cholesterol | Tendency for all healthy volunteers (N = 8) is down but the average decline is very small (only some 3-5%). |
| 9 | fS-Chol.-HDL | Down for all healthy volunteers (N = 8) and in all periods and doses. Average decline some 6%. |
| 10 | fS-Chol-LDL | Down or unchanged (=change less than 2%) for all healthy volunteers (N = 8) in all periods and doses; average decline only some 5%. |
| 11 | fS-Lactate dehydrogenase (LDH) | Down for all healthy volunteers (N = 3) in 4 day test; average decline some 4%. (Subject 3 gave no meaningful result, see above fS-Alat for explanation.) |
| 12 | fS-Na (Sodium) | Down or unchanged for all healthy volunteers (N = 4) in 4 day test; average decline some 1.5%. |
| 13 | fS-Trigly | Blood triglycerides seem to increase relatively significantly for most of the study subjects, although observed levels are still below recommended 2 mmol/l after the increases for all healthy volunteers. |
| 14 | fS-Urate (uric acid) | Down for all healthy volunteers (N = 6) in 4 day test; average decline some 6%. |
| 15 | fS-Urea | Clear tendency for decline. Average decline some 7-8%. |
| 16 | Headache after stopping | All participants that stopped 2 × 6 mg/kg administration at once (N = 3) experienced some symptoms of headache after 20-48 hours after last DGA administration |

TABLE 4-continued

Non-exhaustive summary table of the results from first set of clinical studies, i.e. with non-acute dose/Examples 2.1 and 2.2

| 17 | Lowering of blood pressure | Effect on blood pressure has been tested in scientific manner only on two healthy volunteers (FIG. 12). Only one person had clearly elevated blood pressure: systolic 180 and diastolic 104 before 2 × 6 mg/kg of DGA twice a day. After 10 day treatment blood pressure declined to some 160 and 90. |
| --- | --- | --- |
| 18 | Diuretic effects | Sodium decline in most of the study subjects. |

| No. | Indication | Link to other results |
| --- | --- | --- |
| 1 | Functioning of liver. Reduction of fS-Ala is an indication of an improvement in liver functions. | AST/ALT -ratio declines due to use of DGA indicating improved function of the liver. |
| 2 | Functioning of pancreas, skeletal muscles and heart. Reduction is indication of an improvement. | See also AST/ALT -ratio (see above). |
| 3 | Lower bilirubin level is an indication of increased viability of erythrocytes and/or lower degradation of heme proteins. Antioxidant HO-1 enzyme activity is lowered indicating that the oxidative stress is reduced, i.e. in this lower dose regime HO-1 is only temporarily activated and on average it is down regulated. | See also result bilirubin conjugate and fS-Uraat, i.e. lowered systemic oxidative stress. DGA use can also activate HO-1 gene and increase bilirubin production (see example 2.3), which is a therapy option for some acute diseases and conditions. |
| 4 | Increased viability of erythrocytes and/or lower degradation of heme proteins including. Improved status of the liver. Lower heme protein degradation is also an indication of decreased oxidative stress in these healthy volunteers. | See bilirubin above. |
| 5 | This is a clear indication of improved status of skeletal muscles and heart. | CK also down in higher/acute regime. This strong finding is due to clear increase in energy metabolism by DGA. |
| 6 | Indicates increased use of Fe to the assembly of aerobic heme proteins in e.g. ETS/oxidative phosphorylation. May be also an indication of increased oxygen transporting ability to tissues by erythrocytes. (Nrf2) | See also results bilirubin, bilirubin conjugate and decrease in LDH, and take into account head ache "hangover" when stopping double administration (16). Absolute amount of observed decline in Fe represents on average 0.13% of total Fe bind to blood heme proteins (2.5 g). Thus observed 4 day decline could easily be explained by increased Fe binding to heme proteins due to health effects of DGA. |
| 7 | An indication of increased metabolic flux. Diabetes, insulin resistance and pancreas. | This result is in line with later results that glucose uptake is stimulated by DGA (Example 2.3.4/glucose tolerance test). |
| 8 | Lower risk for cardiovascular disease. The combination of lower oxidative stress and stable or reduced cholesterol in cardiovascular system may reduce the risk of cardiovascular diseases efficiently. | Increased metabolic flux. The use of DGA can also in fact increase the intracellular cholesterol production (see FIG. 4), but on the other hand plasma membrane LDL-receptors are probably also activated thus balancing the effects for fS-Cholesterol into small reduction. |
| 9 | The decline is in line with the decreased amount of LDL and total cholesterol. It seems to be a natural reaction on lower cholesterol. | Decline is in line with the decreased amount of LDL and total cholesterol. |
| 10 | Reduced risk of cardiovascular diseases. See also fS-Cholesterol. | see cholesterol (above) |
| 11 | Indicates increased viability (smaller mortality) of erythrocytes. Possibly also an indication of improved systemic redox state i.e. reduced activity of reactions from pyruvate to lactate by lactate dehydrogenase (LDH). | Improved systemic redox state has been later proven in Example 2.3.3. Pyruvate conversion into lactate reduces significantly with the use of DGA, which is very remarkable proof on the efficacy of DGA. |
| 12 | Lowering of blood pressure. This small decline could also be an indication of increased metabolic flux/ | The decline is in line with the increase on metabolic flux. See |

TABLE 4-continued

Non-exhaustive summary table of the results from first set of clinical studies,
i.e. with non-acute dose/Examples 2.1 and 2.2

| | | |
|---|---|---|
| | diuretic effect of DGA. It may also be an indication of improved renal activity. | also the result that uric acid (fS-Uraat) declined unlike with many other drugs with diuretic effects. |
| 13 | Observed 25-50% increases in blood triglycerides for 5 subjects are likely due to two simultaneous and complementing factors, 1) due to increased demand of triglycerides by the beta-oxidation, and 2) because D-glycerate group molecules are phosphorylated and then reduced towards G-3-P. Note: the increase in endogenous triglycerides consists mostly of medium chain triglycerides that can be even health promoting. | Increase in aerobic ATP production by the use of DGA requires the transportation of energy rich fatty acids from adipose tissues into the liver and further to be transported as triglycerides in to e.g. skeletal muscles, See also examples 4 and 5. |
| 14 | Decline indicates declined oxidative stress of whole cardiovascular system. Also risk of developing gout decreases by declining uric acid. On the other hand elevated uric acid levels have been clearly associated with cardiovascular diseases, type II diabetes and metabolic syndrome. | This decline is in line with observed strong antioxidant properties of DGA in example 1. Combination of increased metabolic flux (Examples 1.1, 2.3.3, 3 and 4) and reduction in oxidative stress is the "sweet spot" for preventing cardio-vascular diseases. |
| 15 | Decline in urea is e.g. an indication of improved renal functions. It is also an indication of increased protein synthesis. The combination of increased ATP production from beta oxidation and clear decline in nitrogen extraction from the body, provides the conversion of fat into muscles by the use of DGA. | Decline in urea production is in line with 10% decline in plasma NO (Example 2.3.3). Blood urea declined also in 4.5 day test with acute dosing. |
| 16 | This is likely an indication that either the oxygen (ATP) or nutrition (ATP) supply to the brain cells has deteriorated after positive effects from DGA ceased to materialize or both. | ATP related explanation is clearly more convincing when related to all other received results. |
| 17 | Lower blood pressure indicates an enhancement on the aerobic activity of skeletal muscles and heart. Possibly also the Nrf2/ARE enhanced redox state of erythrocytes enhance oxygen transport to the tissues in need (pH related increase in 2.3-bisphosphoglycerate). | This result is also in line with decrease in plasma lactate that has been also associated with lowered blood pressure. Likely enhanced aerobic ATP production capacity by the use of DGA and increased flow of oxygen into peripheral tissues allow the blood pressure to be lowered. |
| 18 | Overall, i.e. mitochondrial, cytosolic, ER and peroxisomal, metabolic flux is increased by the use of DGA. This likely causes diuretic effects when starting the use of DGA. | |

REFERENCES CITED

Eriksson C J P, Saarenmaa T, Bykoc I L, Heino P U. Acceleration of Ethanol and Acetaldehyde Oxidation by D-glycerate in Rats. Metabolism 56, 895-898 (2007).

Habe H, Sato S, Fukuoka T, Kitamoto D, Sakaki K. Effect of Glyceric Acid Calcium Salt on the Viability of Ethanol-Dosed Gastric Cells. Journal of Oleo Science 60 (11), 585-590 (2011).

Hoffmann G F et al. Physiology and pathophysiology of organic acids in cerebrospinal fluid. J Inherit Metab Dis. 16(4), 648-69 (1993).

Robergs R A. Exercise-Induced Metabolic Acidosis: Where do the Protons come from? (2001) Sportscience 5(2), sportsci.org/jour/0102/rar.htm, 2001.

The invention claimed is:

1. A method of treating a non-communicable disease or disorder the method comprising administering a composition comprising one or more compounds selected from the group consisting of D-glyceric acid, DL-glyceric acid, L-glyceric acid, a salt of D-glyceric acid, a salt of DL-glyceric acid, an ester of D-glyceric acid, and an ester of DL-glyceric acid, as the only active substance or substances, to a subject in need thereof, wherein the composition enhances mitochondrial ATP production and simultaneously reduces excessive radical oxygen species formation from oxidative phosphorylation (OXPHOS), and wherein the non-communicable disease or disorder is selected from the group consisting of: a cardiovascular disease or disorder, mitochondrial DNA depletion, mitochondrial diseases, cerebrovascular accident, damage from acute head injury, acute or chronic renal failure, acute or chronic liver failure, splenomegaly, acute or chronic pancreatic failure, hemorrhagic shock, pre-eclampsia, thyroid disease, chronic fatigue, fibromyalgia, multi-organ dysfunction syndrome, epilepsy, bipolar disorder, psychiatric and mood disorders, obesity, high blood pressure, an age-related degeneration disease or disorder, rheumatoid arthritis, gout, and chronic obstructive pulmonary disease.

2. The method according to claim 1, wherein the composition regulates an inducible heme oxygenase pathway to enhance endogenous antioxidant and anti-inflammatory activity in the subject.

3. The method according to claim 1, wherein the composition increases endogenous pyruvate concentration to provide substrates for aerobic ATP production and anabolic reactions, and enhances endogenous antioxidant and anti-inflammatory activity in the subject.

4. The method according to claim 1, wherein the cardiovascular disease or disorder is selected from the group consisting of: atherosclerosis, myocardial infarction, cardiomyopathy or congestive heart failure, and vascular thrombosis and embolism, or wherein the age-related degeneration disease or disorder is selected from the group consisting of: age related hearing loss, age related macular degeneration, glaucoma, optic neuropathy, retinitis pigmentosa, sarcopenia, osteoporosis, chronic neurodegeneration, amyotrophic lateral sclerosis, Alzheimer's disease, Parkinson's disease, and multiple sclerosis.

5. The method according to claim 1, wherein the composition further comprises a pharmaceutically acceptable excipient.

6. The method according to claim 1, wherein the composition is in a form of a solution, syrup, powder, ointment, mixture, capsule, tablet, or an inhalable preparation.

7. The method according to claim 1, wherein the composition is in a form suitable for parenteral, oral, topical or inhalable administration.

8. The method according to claim 1, wherein the composition is part of a beverage, a food product, a functional food, a dietary supplement, or a nutritive substance.

9. The method according to claim 1, wherein the composition is a pharmaceutical composition.

10. The method of claim 1, wherein the composition comprises one or more of D-glyceric acid, DL-glyceric acid, a salt of D-glyceric acid, a salt of DL-glyceric acid, an ester of D-glyceric acid, and an ester of DL-glyceric acid.

11. The method of claim 10, wherein the composition comprises one or more of D-glyceric acid, a salt of D-glyceric acid, and an ester of D-glyceric acid.

12. A method of treating a non-communicable disease or disorder the method comprising administering a composition comprising one or more compounds selected from the group consisting of D-glyceric acid, DL-glyceric acid, L-glyceric acid, a salt of D-glyceric acid, a salt of DL-glyceric acid, an ester of D-glyceric acid, and an ester of DL-glyceric acid, wherein the salts of D-glyceric acid and DL-glyceric acid are calcium salts, as the only active substance or substances, to a subject in need thereof, wherein the composition enhances mitochondrial ATP production and simultaneously reduces excessive radical oxygen species formation from oxidative phosphorylation (OXPHOS), and wherein the non-communicable disease or disorder is selected from the group consisting of: a cardiovascular disease or disorder, mitochondrial DNA depletion, mitochondrial diseases, cerebrovascular accident, damage from acute head injury, acute or chronic renal failure, acute or chronic liver failure, splenomegaly, acute or chronic pancreatic failure, hemorrhagic shock, pre-eclampsia, thyroid disease, chronic fatigue, fibromyalgia, multi-organ dysfunction syndrome, epilepsy, bipolar disorder, psychiatric and mood disorders, cancer, obesity, high blood pressure, an age-related degeneration disease or disorder, rheumatoid arthritis, gout, and chronic obstructive pulmonary disease.

13. A method of treating a non-communicable disease or disorder the method comprising administering a composition comprising one or more compounds selected from the group consisting of D-glyceric acid, DL-glyceric acid, L-glyceric acid, and salts and esters thereof, as the only active substance or substances, to a subject in need thereof, wherein the composition enhances mitochondrial ATP production and simultaneously reduces excessive radical oxygen species formation from oxidative phosphorylation (OXPHOS), and wherein the non-communicable disease or disorder is selected from the group consisting of: a cardiovascular disease or disorder, mitochondrial DNA depletion, mitochondrial diseases, cerebrovascular accident, damage from acute head injury, acute or chronic renal failure, acute or chronic liver failure, splenomegaly, acute or chronic pancreatic failure, hemorrhagic shock, pre-eclampsia, thyroid disease, chronic fatigue, fibromyalgia, multi-organ dysfunction syndrome, bipolar disorder, psychiatric and mood disorders, obesity, high blood pressure, an age-related degeneration disease or disorder, rheumatoid arthritis, gout, and chronic obstructive pulmonary disease.

* * * * *